US009925261B2

(12) United States Patent
Karumanchi et al.

(10) Patent No.: US 9,925,261 B2
(45) Date of Patent: *Mar. 27, 2018

(54) METHODS OF TREATING PRE-ECLAMPSIA OR ECLAMPSIA

(71) Applicant: Beth Israel Deaconess Medical Center, Inc., Boston, MA (US)

(72) Inventors: S. Ananth Karumanchi, Chestnut Hill, MA (US); Sharon Maynard, Emmaus, PA (US); Vikas P. Sukhatme, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/605,649

(22) Filed: Jan. 26, 2015

(65) Prior Publication Data
US 2016/0175434 A1 Jun. 23, 2016

Related U.S. Application Data

(60) Continuation of application No. 12/892,652, filed on Sep. 28, 2010, now abandoned, which is a division of application No. 12/069,757, filed on Feb. 12, 2008, now Pat. No. 7,846,433, which is a division of application No. 10/771,518, filed on Feb. 4, 2004, now Pat. No. 7,335,362, which is a continuation-in-part of application No. 10/624,809, filed on Jul. 21, 2003, now Pat. No. 7,407,659.

(60) Provisional application No. 60/467,390, filed on May 2, 2003, provisional application No. 60/451,796, filed on Mar. 3, 2003, provisional application No. 60/397,481, filed on Jul. 19, 2002.

(51) Int. Cl.
| | |
|---|---|
| *A61K 39/395* | (2006.01) |
| *A61K 38/18* | (2006.01) |
| *G01N 33/74* | (2006.01) |
| *C07K 16/28* | (2006.01) |
| *G01N 33/68* | (2006.01) |
| *C12Q 1/48* | (2006.01) |
| *A61K 31/522* | (2006.01) |
| *C07K 16/12* | (2006.01) |
| *C07K 16/18* | (2006.01) |
| *C07K 16/40* | (2006.01) |
| *C12N 15/113* | (2010.01) |
| *A61K 45/06* | (2006.01) |
| *A61K 39/00* | (2006.01) |

(52) U.S. Cl.
CPC ........ *A61K 39/3955* (2013.01); *A61K 31/522* (2013.01); *A61K 38/1866* (2013.01); *A61K 38/1891* (2013.01); *A61K 45/06* (2013.01); *C07K 16/1217* (2013.01); *C07K 16/18* (2013.01); *C07K 16/2863* (2013.01); *C07K 16/40* (2013.01); *C12N 15/1138* (2013.01); *C12Q 1/485* (2013.01); *G01N 33/689* (2013.01); *G01N 33/6893* (2013.01); *G01N 33/74* (2013.01); *A61K 2039/505* (2013.01); *C07K 2317/76* (2013.01); *C12N 2310/11* (2013.01); *C12N 2310/14* (2013.01); *G01N 2500/00* (2013.01); *G01N 2800/368* (2013.01)

(58) Field of Classification Search
CPC .......... A61K 39/3955; A61K 38/1866; G01N 33/74; G01N 33/689; G01N 2800/368; C07K 16/2863; C12Q 1/485
See application file for complete search history.

(56) References Cited

U.S. PATENT DOCUMENTS

| | | | |
|---|---|---|---|
| 5,194,596 | A | 3/1993 | Tischer et al. |
| 5,219,739 | A | 6/1993 | Tischer et al. |
| 5,238,819 | A | 8/1993 | Roberts et al. |
| 5,240,848 | A | 8/1993 | Keck et al. |
| 5,332,671 | A | 7/1994 | Ferrara et al. |
| 5,543,138 | A | 8/1996 | Keith |
| 5,712,395 | A | 1/1998 | App et al. |
| 5,763,441 | A | 6/1998 | App et al. |
| 5,830,879 | A | 11/1998 | Isner |
| 5,895,783 | A | 4/1999 | Garfield et al. |
| 5,958,715 | A | 9/1999 | Muller |
| 6,100,071 | A | 8/2000 | Davis-Smyth et al. |
| 6,258,787 | B1 | 7/2001 | Isner |
| 6,365,157 | B2 | 4/2002 | Rockwell et al. |
| 6,399,585 | B1 | 6/2002 | Larson et al. |
| 6,410,322 | B1 | 6/2002 | Robinson |
| 6,447,768 | B1 | 9/2002 | van Zonneveld et al. |

(Continued)

FOREIGN PATENT DOCUMENTS

| | | |
|---|---|---|
| EP | 1417971 A2 | 5/2004 |
| WO | WO-98/28006 A1 | 7/1998 |

(Continued)

OTHER PUBLICATIONS

Aali et al., "Nifedipine or hydralazine as a first-line agent to control hypertension in severe preeclampsia," Acta Obstet Cynecol Scand. 81(1):25-30 (2002) (abstract).
Australian Examination Report for Application No. 2009202176, dated Feb. 21, 2011.
Brockelsby et al., "VEGF via VEGF receptor-1 (Flt-1) mimics preeclamptic plasma in inhibiting uterine blood vessel relaxation in pregnancy: implications in the pathogenesis of preeclampsia, " Lab Invest. 79(9):1101-11 (1999).
Canadian Office Action for Application No. 2,469,253, dated Aug. 30, 2010.
Canadian Office Action for Application No. 2,496,253, dated Oct. 4, 2011.
Canadian Office Action for Application No. 2,554,971, dated Aug. 10, 2011.
Dombrowski et al.,"Incidence of preeclampsia among asthmatic patients lower with theophylline," Am J Obstet Gynecol. 155(2):265-7 (1986) (abstract).
European Examination Report for EP 03765913.3, dated May 31, 2011.
European Examination Report for EP 09014672.1, dated Nov. 3, 2010.

(Continued)

*Primary Examiner* — Ruixiang Li
(74) *Attorney, Agent, or Firm* — Clark & Elbing LLP

(57) ABSTRACT

Disclosed herein are methods for treating pre-eclampsia and eclampsia using compounds that increase VEGF or PlGF levels or compounds that decrease sFlt-1 levels. Compounds that inhibit the binding of VEGF or PlGF to sFlt1- are also disclosed herein for the treatment of pre-eclampsia or eclampsia.

34 Claims, 13 Drawing Sheets

(56) References Cited

U.S. PATENT DOCUMENTS

| | | | |
|---|---|---|---|
| 6,528,676 | B1 | 3/2003 | D'Amato et al. |
| 6,613,757 | B1 | 9/2003 | Garfield et al. |
| 6,660,534 | B2 | 12/2003 | McVicker et al. |
| 6,677,300 | B1 | 1/2004 | Schreiner et al. |
| 7,030,083 | B2 | 4/2006 | Schreiner et al. |
| 7,323,346 | B2 | 1/2008 | Thadhani et al. |
| 7,335,362 | B2 | 2/2008 | Karumanchi et al. |
| 7,344,892 | B2 | 3/2008 | Thadhani et al. |
| 7,407,659 | B2 | 8/2008 | Karumanchi et al. |
| 7,435,419 | B2 | 10/2008 | Karumanchi et al. |
| 7,727,733 | B2 | 6/2010 | Buhimschi et al. |
| 7,740,849 | B2 * | 6/2010 | Karumanchi ...... A61K 31/4439 424/139.1 |
| 2001/0056068 | A1 | 12/2001 | Chwalisz et al. |
| 2003/0114412 | A1 | 6/2003 | Ward et al. |
| 2003/0144298 | A1 | 7/2003 | Curwen et al. |
| 2003/0220262 | A1 | 11/2003 | Schreiner et al. |
| 2004/0038305 | A1 | 2/2004 | Poston et al. |
| 2004/0126828 | A1 | 7/2004 | Karumanchi et al. |
| 2005/0025762 | A1 | 2/2005 | Karumanchi et al. |
| 2005/0148023 | A1 | 7/2005 | Thadhani et al. |
| 2005/0148040 | A1 | 7/2005 | Thadhani et al. |
| 2005/0170444 | A1 | 8/2005 | Karumanchi et al. |
| 2006/0183175 | A1 | 8/2006 | Buhimschi et al. |

FOREIGN PATENT DOCUMENTS

| | | |
|---|---|---|
| WO | WO-0013702 A2 | 3/2000 |
| WO | WO-02/37120 A2 | 5/2002 |
| WO | WO-2004/008946 A2 | 1/2004 |
| WO | WO-2005/031364 A1 | 4/2005 |
| WO | WO-2006/069373 A2 | 6/2006 |
| WO | WO-08/28006 A2 | 3/2008 |
| WO | WO-2010/075475 A1 | 7/2010 |

OTHER PUBLICATIONS

Extended European Search Report for EP 10180382.3, dated May 20, 2011, dated Jun. 20, 2011.
Extended European Search Report for EP 10180400.3, dated May 20, 2011, dated Jun. 20, 2011.
Indonesian Office Action for Applicatio No. W-00200500421, dated Nov. 15, 2010.
Japanese Office Action for Application No. 2005-505542 (English Translation).
Japanese Office Action for Application No. 2006-552339, dated Dec. 17, 2010 (English Translation).
Koos, "Management of uncorrected, palliated, and repaired cyanotic congenital heart disease in pregnancy," Prog Pediatr Cardiol. 19(1):25-45 (2004).
Korean Office Action for Application No. 10-2005-7001052, dated Sep. 16, 2010 (English Translation).
Kyle et al., "A comparison of the inactive urinary kallikrein: creatine ration and the angiotensin sensitivity test for the prediction of pre-eclampsia," Chem Abstracts. 126:474, Abstract No. 4166b (1997).
Lindqvist et al., "Moderate smoking during pregnancy is associated with a reduced risk of preeclampsia," Acta Obstet Gynecol Scand. 78(8):693-7 (1999) (abstract).
Mordel et al., "Successful full-term pregnancy in familial Mediterranean fever complicated with amyloidosis: case report and review of the literature," Fetal Diagn Ther. 8(2):129-34 (1993).
Phillipine Office Action for Application No. 1-2005-500130, dated Jun. 13, 2011.
Phillipine Office Action for Application No. 1-2005-500130, dated Oct. 13, 2010.
Powers, et al. "Maternal serum soluble fms-like tyrosine kinase 1 concentrations are not increased in early pregnancy and decrease more slowly postpartum in women who develop preeclampsia" Am J Obstet Gynecol. 193(1):185-91(2005).
Stumpf, "Drug therapy of hypertensive crises," Clin Pharm. 7(8):582-91 (1988) (abstract).
Wu et al., "Monoclonal antibody against VEGFR-1 directly inhibits flt1-positive breast tumor growth, " Eur J Cancer. 38:S152 Poster #508 (2002).
Wu et al., "Monoclonal antibody against VEGFR1 inhibits flt1-postive breast tumor growth by a dual mechanism involving anti-endothelial and anti-tumor cell growth activities, " Proceedings of the Annual Meeting of the American Association for Cancer Research 43:527 (2002).
Yoneyama et al., "Plasma adenosine levels and P-selectin expression on platelets in preeclampsia," Obstet Gynecol. 97(3):366-70 (2001) (abstract).
Korean Office Action for Application No. 2006-7017827, dated Aug. 30, 2011 (English Translation).
Japanese Office Action for Application No. 2014-119588, dated Jul. 2, 2015 (9 pages).
Vuorela et al., "Amniotic fluid—soluble vascular endothelial growth factor receptor-1 in preeclampsia," Obstet Gynecol. 95(3):353-7 (2000).
Aggarwal et al., "Low urinary placental growth factor is a marker of preeclampsia," Kidney Int. 69(3):621-4 (2006).
Ahmad et al., "Elevated placental soluble vascular endothelial growth factor receptor-1 inhibits angiogenesis in preeclampsia," Circ. Res. 95(9):884-91 (2004).
Ahmed et al., "Regulation of Placental Vascular Endothelial Growth Factor (VEGF) and Placenta Growth Factor (PIGF) and Soluble Flt-1 by Oxygen—A Review," Placenta 21 :S16-S24 (2000).
Associate Correspondence and English Translation of Unfavourable Opinion issued in Brazilian Patent Application No. PI0312818-0, dated Dec. 19, 2016 (10 pages).
Australian Examination Report for AU 2009202176 dated Mar. 16, 2011, dated Feb. 21, 2011 (3 pages).
Baek et al., "Hypoxia-Induced VEGF Enhances Tumor Survivability Via Suppression of Serum Deprivation-Induced Apoptosis," Oncogene 19:4621-4631 (2000).
Baker et al., "Elevated serum levels of vascular endothelial growth factor in patients with preeclampsia," Obstet. Gynocol. 86:815-21 (1995).
Barleon et al., "Soluble VEGFR-1 Secreted by Endothelial Cells and Monocytes is Present in Human Serum and Plasma from Healthy Donors," Angiogenesis 4:143-154 (2001).
Baumgartner et al., "Constitutive Expression of phVEGF165 After Intramuscular Gene Transfer Promotes Collateral Vessel Development in Patients with Critical Limb lschemia," Circulation 97:1114-1123 (1998).
Baumwell et al., "Preeclampsia: clinical manifestations and molecular mechanisms," Nephron. Clin. Pract. 106(2):c72-81 (2007).
Bdolah et al., "Angiogenic imbalance in the pathophysiology of preeclamsia: newer insights," Semin. Nephrol. 24(6):548-56 (2004).
Bdolah et al., "Recent advances in understanding of preeclampsia," Croat. Med. J. 46(5):728-36 (2005).
Belgore et al., "Measurement of Free and Complexed Soluble Vascular Endothelial Growth Factor Receptor, Flt-1, in Fluid Samples: Development and Application of Two New Immunoassays," Clin. Sci. 100:567-575 (2001).
Belgore et al., Plasma Levels of Vascular Endothelial Growth Factor and Its Soluble Receptor (SFlt-1) in Essential Hypertension,• Am. J. Cardiol. 87:805-807 (2001).
Belgore et al., "sFlt-1, a Potential Antagonist for Exogenous VEGF," Circulation 102:E108-E109 (2000).
Belgore et al., "Successful Therapy Reduces Levels of Vascular Endothelial Growth Factor (VEGF) in Patients with Hypertension and Patients with Hypercholesterolemia," Atherosclerosis 151 :599 (2000).
Belgore et al., "Vascular Endothelial Growth Factor and its Receptor, Flt-1, in Smokers and Non-Smokers," Br. J. Biomed. Sci. 57:207-213 (2000).

(56) References Cited

OTHER PUBLICATIONS

Blann et al., "Plasma Vascular Endothelial Growth Factor and Its Receptor Flt-1 in Patients with Hyperlipidemia and Atherosclerosis and the Effects of Fluvastatin or Fenofibrate," Am. J. Cardiol. 87:1160-1163 (2001).
Bolte et al., "Management and monitoring of severe preeclampsia," Eur J Obstet Gynecol Reprod Biol. 96:8-20 (2001).
Bouletreau et al., "Hypoxia and VEGF Up-Regulate BMP-2 mRNA and Protein Expression in Microvascular Endothelial Cells: Implications for Fracture Healing," Plast. Raconstr. Surg. 109:2384-2397 (2002).
Brown et al., "Vascular permeability factor mRNA and protein expression in human kidney," Kidney Int. 42:1457-61 (1992).
Canadian Office Action for Application No. 2,922,031, dated Sep. 8, 2016 (3 pages).
Carmeliet et al., "Synergism between vascular endothelial growth factor and placental growth factor contributes to angiogenesis and plasma extravasation in pathological conditions," Nat. Med. 5: 575-583 (2001).
Celletti et al., "Effect of Human Recombinant Vascular Endothelial Growth Factor165 on Progression of Atherosclerotic Plaque," J. Am. Coll. Cardiol. 37:2126-2130 (2001).
Charnock-Jones et al., "Determination of the Circulating Levels of the Soluble Form of the VEGF-R1 (sFlt-1) in Women at High Risk of Developing Pre-Eclampsia," J. Soc. Gynecol. Investig.10:166A Abstract No. 230 (2003).
Charnock-Jones et al., "Identification and Localization of Alternately Spliced mRNAs for Vascular Endothelial Growth Factor in Human Uterus and Estrogen Regulation in Endometrial Carcinoma Cell Lines," Biol. Reprod. 48: 1120-1128 (1993).
Clark et al., "A vascular endothelial growth factor antagonist is produced by the human placenta and released into the maternal circulation," Biol Reprod. 59(6):1540-8 (1998).
Cockell et al., "Human Placental Syncytiotrophoblast Microvillous Membranes Impair Maternal Vascular Endothelial Function," Br. J. Obstet. Gynaecol. 104:235-240 (1997).
Cohen et al., "Amelioration of Diabetic Nephropathy by Treatment with Monoclonal Antibodies Against Glycated Albumin," Kidney Int. 45:1673-1679 (1994).
Communication Pursuant to Article 94(3) EPC for EP 03765913.3, dated Sep. 15, 2009 (6 pages).
Cooper et al., "VEGF mRNA levels in placentae from pregnancies complicated by pre-eclampsia," B.J. Obstet. Gynacol. 103:1191-6 (1996).
Davis-Smyth et al., "Mapping the charged residues in the second immunoglobulin-like domain of the vascular endothelial growth factor/placenta growth factor receptor Flt-1 required for binding and structural stability," J. Biol. Chem. 273:3216-22 (1998).
Davis-Smyth et al., "The second immunoglobulin-like domain of the VEGF tyrosine kinase receptor Flt-1 determines ligand binding and may initiate a signal transduction cascade," EMBO J. 15:4919-27 (1996).
Davison et al., "New Aspects in the Pathophysiology of Preeclampsia," J. Am. Soc. Nephrol. 15: 2440-2448 (2004).
Del-Sorbo et al., "The synthesis of platelet-activating factor modulates chemotaxis of monocytes induced by HIV-1 Tat," Eur. J. Immunol. 29:1513-1521 (1999).
Deodato et al., "Recombinant AAV Vector Encoding Human VEGF165 Enhances Wound Healing," Gene Ther. 9:777-785 (2002).
Eddahibi et al., "Imbalance Between Platelet Vascular Endothelial Growth Factor and Platelet-Derived Growth Factor in Pulmonary Hypertension," Am. J. Respir. Grit. Care Med. 162:1493-1499 (2000).
Eremina et al., "Glomerular-Specific Alterations of VEGF-A Expression Lead to Distinct Congenital and Acquired Renal Diseases," J. Clin. Invest. 111 :707-716 (2003).
Errico et al., "Identification of placenta growth factor determinants for binding and activation of Flt-1 receptor," J. Biol. Chem. 279:43929-39 (2004).

Eskild et al., "Levels of Angiogenic Factors in Pregnancy and Post-Partum Bleeding," Acta. Obstet. Gynecol. Scand. 87(10): 1081-1083 (2008).
European Search Report dated May 23, 2007 (PCT/US0322892).
European Search Report for EP application No. EP 03765913.3 dated May 10, 2007.
Extended European Search Report for EP application No. EP 09014672.1, dated Mar. 3, 2010 (8 pages).
Ferguson, "Meeting Highlights: Highlights of the 48th Scientific Sessions of the American College of Cardiology," Circulation 100:570-575 (1999).
Ferrara et al., "Role of vascular endothelial growth factor in regulation of physiological angiogenesis," Am. J. Physiol. Cell Physiol. 280:C1358-66 (2001).
Ferrara et al., "The biology of VEGF and its receptors," Nat. Med. 9:669-76 (2003).
Ferrara et al., "The Role of Vascular Endothelial Growth Factor in Angiogenesis," Acta Haematol. 106:148-156 (2001).
Ferrara, "Role of vascular endothelial growth factor in the regulation of angiogenesis," Kidney International, 56:794-814. (1999.).
Foreign Search Report for Application No. SG 200500265-4 dated Jan. 11, 2007.
Freedman et al., "Therapeutic Angiogenesis for Coronary Artery Disease," Ann. Intern. Med. 136:54-71 (2002).
Germain et al., "Endothelial Dysfunction: A Link Among Preeclampsia, Recurrent Pregnancy Loss, and Future Cardiovascular Events?" Hypertension 49(1): 90-95 (2006).
Gille et al., "Analysis of Biological Effects and Signaling Properties of Flt-1 (VEGFR-1) and KDR (VEGFR-2)," J. Biol. Chem. 276:3222-3230 (2001 ).
Gordon et al., "Phase I safety and pharmacokinetic study of recombinant human anti-vascular endothelial growth factor in patients with advanced cancer," J. Clin. Oncol. 19:843-850 (2001).
Graubert et al., "Vascular Repair After Menstruation Involves Regulation of Vascular Endothelial Growth Factor-Receptor Phosphorylation by sFLT-1," Am. J. Pathol. 158:1399-1410 (2001).
Hayashi et al., "Changes in Urinary Excretion of Six Biochemical Parameters in Normotensive Pregnancy and Preeclampsia," Am. J. Kidney Dis. 39:392-400 (2002).
He et al., "Alternative Splicing of Vascular Endothelial Growth Factor (VEGF)-R1 (FLT-1) Pre-mRNA is Important for the Regulation of VEGF Activity," Mol Endocrinol. 13:537-45 (1999).
He et al., "Vascular Endothelial Growth Factor Signals Endothelial Cell Production of Nitric Oxide and Prostacyclin through Flk-1/KDR Activation of c-Src," J. Biol. Chem. 274:25130-25135 (1999).
Heeschen et al., "Nicotine Stimulates Angiogenesis and Promotes Tumor Growth and Atherosclerosis," Nat.Med. 7:833-839 (2001).
Helske et al., "Expression of vascular endothelial growth factor receptors 1, 2 and 3 in placentas from normal and complicated pregnancies," Mol Hum Reprod. 7(2):205-10. (2001).
Henry et al., "Intracoronary Administration of Recombinant Human Vascular Endothelial Growth Factor to Patients with Coronary Artery Disease," Am. Heart J. 142:872-880 (2001).
Holzgreve et al., "Disturbed Feto-Maternal Cell Traffic in Preeclampsia," Obstet. Gynecol. 91 :669-672 (1998).
Hornig et al.,"Release and Complex Formation of Soluble VEGFR-1 from Endothelial Cells and Biological Fluids," Lab. Invest. 80:443-454 (2000).
Hsieh, Tsang-Tang, "Maternal serum placenta growth factor and vascular endothelial growth factor in pregnancies complicated by preeclampsia," Am. J. Obstet. Gynecol. 184:S70 (2001). (Abstract).
Hunter et al., "Serum levels of vascular endothelial growth factor in preeclamptic and normotensive pregnancy," Hypertension 36:965-969 (2000).
Indonesian Office Action for Application No. W-00200500421, dated Oct. 6, 2016 (1 page).
International Search Report and Written Opinion for International Application No. PCT/US05/03884, dated Feb. 3, 2006. (10 pages).
International Search Report for International Application No. PCT/US03/22892, dated Nov. 16, 2005. (8 pages).
Isner et al., "VEGF Gene Transfer for Diabetic Neuropathy," Hum. Gene Ther. 12:1593-1594 (2001).

(56) References Cited

OTHER PUBLICATIONS

Isner, "Myocardial Gene Therapy," *Nature* 415:234-239 (2002).
Iyer et al., "The crystal structure of the human placenta growth factor-1 (PIGF-1), an angiogenic protein, at 2.0 A resolution," J. Biol. Chem. 276:12153-61 (2001).
Jelkmann, "Pitfalls in the measurement of circulating vascular endothelial growth factor," Clin Chem. 47(4):617-23. (2001).
Kabbinavar et al., "Phase II, Randomized Trial Comparing Bevacizumab Plus Fluorouracil (FU)/Leucovorin (LV) with FU/LV Alone in Patients with Metastatic Randomized Colorectal Cancer," *J. Clin. Oncol.* 21:60-65 (2003).
Kaku et al., "Effects of Vascular Endothelial Growth Factor on Osteoclast Induction During Tooth Movement in Mice," *J. Dent. Res.* 80:1880-1883 (2001).
Karumanchi et al., "Advances in the Understanding of Eclampsia," *Curr. Hypertens. Rep.* 10(4): 305-312 (2008).
Karumanchi et al., "Hypoxia and Sflt-1 in Preeclampsia: The "Chicken-and-Egg" Question," *Endocrinology* 145(11): 4835-4837 (2004).
Karumanchi et al., "In vivo rat model of preeclampsia," Methods Mol Med. 122(2):393-9 (2006).
Karumanchi et al., "Placental lschemia and Soluble Fms-Like Tyrosine Kinase 1: Cause or Consequence of Preeclampsia?" *Kidney Int.* 71(10): 959-961 (2007).
Karumanchi et al., "Preeclampsia and the Kidney: Footprints in the Urine," *Am. J. Obstet. Gynecol.* 196(4): 287-288 (2007).
Karumanchi et al., "Preeclampsia Pathogenesis: "Triple a Rating"—Autoantibodies and Antiangiogenic Factors," *Hypertension* 51(4): 991-992 (2008).
Karumanchi et al., "Preeclampsia: A Renal Prespective," *Kidney Int.* 67(6): 2101-2113 (2005).
Kendall et al., "Identification of a Natural Soluble Form of the Vascular Endothelial Growth Factor Receptor, FLT-1, and Its Heterodimerization with KOR," *Biochem. Biophys. Res. Commun.* 226:324-328 (1996).
Kendall et al., "Inhibition of Vascular Endothelial Cell Growth Factor Activity by an Endogenously Encoded Soluble Receptor," *Proc. Natl. Acad. Sci.* 90:10705-10709 (1993).
Keyt et al., "Identification of vascular endothelial growth factor determinants for binding KDR and Flt-1 receptor," J. Biol. Chem. 271:5638-5646 (1996).
Kincaid-Smith, "The Renal Lesion of Preeclampsia Revisited," *Am. J. Kidney Dis.* 17:144-148 (1991 ).
Knebelmann et al., "Transforming Growth Factor alpha Is a Target for the Von Hippel-Lindau Tumor Suppressor," *Cancer Res.* 58:226-231 (1998).
Koga et al., "Elevated Serum Soluble Vascular Endothelial Growth Factor Receptor 1 (sVEGFR-1) Levels in Women with Preeclampsia," *J. Clin. Endocrinol. Metab.* 88:2348-2351 (2003).
Koransky, "VEGF Gene Delivery for Treatment of Ischemic Cardiovascular Disease," *Trends Cardiovasc. Med.* 12: 108-114 (2002).
Krussel et al., "Expression of mRNA for Vascular Endothelial Growth Factor Transmembraneous Receptors Flt1 and KDR, and the Soluable Receptor sflt in Cycling Human Endometrium," Mol. Hum. Reprod. 5: 452-458 (1999).
Kuo et al., "Comparative Evaluation of the Antitumor Activity of Antiangiogenic Proteins Delivered by Gene Transfer," *Proc. Natl. Acad. Sci. U.S.A.* 98:4605-4610 (2001 ).
Lai et al., "Inhibition of Angiogenesis by Adenovirus-Mediated sFlt-1 Expression in a Rat Model of Corneal Neovascularization," *Hum. Gene Ther.* 12:1299-1310 (2001).
Lai et al., "Potential Long-Term Inhibition of Ocular Neovascularisation by Recombinant Adeno-Associated Virus-Mediated Secretion Gene Therapy," Gene Ther. 9:804-813 (2002).
Lain et al., "Contemporary Concepts of the Pathogenesis and Management of Preeclampsia," *JAMA* 287: 3183-3186 (2002).
Lam et al., "Circulating Angiogenic Factors in the Pathogenesis and Prediction of Preeclampsia," *J. Hypertension* 46(5): 1077-1085 (2005).

Lash et al., "Vascular endothelial growth factor and placental growth factor release in cultured trophoblast cells under different oxygen tensions," Growth Factors 20(4):189-96 (2002).
LeCouter et al., "Identification of an Angiogenic Mitogen Selective for Endocrine Gland Endothelium," Nature 412:868-9 (2001).
Levine et al., "Circulating angiogenic factors and the risk of preeclampsia," N. Engl. J. Med. 350:672- 683 (2004).
Levine et al., "Serum Sflt1 Concentration During Preeclampsia and Mid Trimester Blood Pressure in Healthy Nulliparous Women," Am. J. Obstet. Gynecol. 194(4): 1034-1041 (2006).
Levine et al., "Trial of Calcium for Preeclampsia Prevention (CPEP): Rationale, Design, and Methods," *Control Clin. Trials* 17:442-469 (1996).
Levine et al., "Trial of Calcium to Prevent Preeclampsia," *N. Engl. J. Med.* 337:69-76 (1997).
Levine et al., "Two-Stage Elevation of Cell-Free Fetal DNA in Maternal Sera Before Onset of Preeclampsia," Am. J. Obstet. Gynecol. 190: 707-713 (2004).
Levine et al., "Urinary placental growth factor and risk of preeclampsia," JAMA 293:77-85 (2005).
Li et al., "Recombinant Vascular Endothelial Growth Factor 121 Attenuates Hypertension and Improves Kidney Damage in a Rat Model of Preeclampsia," Hypertension 50(4): 686-692 (2007).
Li et al., "Recombinant VEGF121 Attenuates Hypertension and Improves Kidney Damage in a Rat Model of Preeciampsia," Hypertension 092098 (2007).
Lip et al., "Plasma VEGF and Soluble VEGF Receptor FLT-1 in Proliferative Retinopathy: Relationship to Endothelial Dysfunction and Laser Treatment," *Invest. Ophthalmol. Vis. Sci.* 41 :2115-2119 (2000).
Livingston et al., "Placenta growth factor is not an early marker for the development of severe preeclampsia," Am. J. Obstet. Gynecol. 184:1218-1220 (2001).
Livingston et al., "Reductions of vascular endothelial growth factor and placental growth factor concentrations in severe preeclampsia," Am. J. Obstet. Gynecol. 183:1554-1557 (2000).
Lutton et al., "Revascularization of ischemic tissues by PIGF treatment, and inhibition of tumor angiogenesis, arthritis and artherosclerosis by anti-Flt1," Nat. Med. 8:831-40 (2002).
Luttun et al., "Soluble VEGF Receptor Flt1: The Elusive Preclampsia Factor Discovered?" *J. Clin. Invest.* 111 :600-602 (2003).
Lyall et al., "Suppression of serum vascular endothelial growth factor immunoreactivity in normal pregnancy and in pre-eclamsia," BJOG 104:223-8 (1997).
Margolin et al., "Phase lb trial of intravenous recombinant humanized monoclonal antibody to vascular endothelial growth factor in combination with chemotherapy in patients with advanced cancer: pharmacologic and long-term safety data," J. Clin. Oncol. 19:851-856 (2001).
Masuda et al., "Vascular Endothelial Growth Factor Enhances Glomerular Capillary Repair and Accelerates Resolution of Experimentally Induced Glomerulonephritis," *Am. J. Pathol.* 159:599-608 (2001 ).
Maynard et al., "Excess Placental Soluble fms-Like Tyrosine Kinase 1 (sFlt1) May Contribute to Endothelial Dysfunction, Hypertension, and Proteinuria in Preeclampsia," *J. Clinical Invest.* 111 :649-658 (2003).
Maynard et al., "Preeclampsia and Angiogenic Imbalance," *Annu. Rev. Med.* 59: 61-78 (2008).
Maynard et al., "Sflt-1, a circulating VEGF antagonist, is upregulated in preeciampsia and contributes to endothelial dysfunction." J. Am. Soc. Nephrol. 13: SU-FC280 (2002).
Maynard et al., "Soluble Fms-like Tyrosine Kinase 1 (sFlt1) and Endothelial Dysfunction in the Pathogenesis of Preeclampsia," *Pediatr. Res.* 57: 1R-7R (2005).
Mills et al., "Prostacyclin and Thromboxane Changes Predating Clinical Onset of Preeclampsia," *JAMA* 281 :356-362 (1999).
Moran et al., "Glomerular Ultrafiltration in Normal and Preeclamptic Pregnancy," J. Am. Soc. Nephrol. 14: 648-52 (2003).
Morbidelli et al., "Nitric Oxide Mediates Mitogenic Effect of VEGF on Coronary Venular Endothelium," *Am. J. Physiol.* 270:H411-H415 (1996).

(56) References Cited

OTHER PUBLICATIONS

Mortensen et al., "Smoking, Sex of the Offspring, and Risk of Placental Abruption, Placenta Previa, and Preeclampsia: A Population-Based Cohort Study," *Acta Obstet. Gynecol. Scand* 80:894-898 (2001).
Muller et al., "The crystal structure of vascular endothelial growth factor (VEGF) refined to 1.93 A resolution: multiple copy flexibility and receptor binding," Structure 5:1325-1338 (1997).
Muller et al., "Vascular endothelial growth factor: crystal structure and functional mapping of the kinase domain receptor binding site," Proc. Natl. Acad. Sci. USA 94: 7192-7197 (1997).
Myers et al., "Hypertensive Diseases and Eclampsia," *Curr. Opin. Obstet. Gynecol.* 14:119-125 (2002).
Nagamatsu et al., "Cytotrophoblasts Up-Regulate Soluble Fms-Like Tyrosine Kinase-1 Expression Under Reduced Oxygen: An Implication for the Placental Vascular Development and the Pathophysiology of Preeclampsia," Endocrinology. 145(11):4838-45 (2004).
Neufeld et al., "Similarities and Differences Between the Vascular Endothelial Growth Factor (VEGF) Splice Variants," *Cancer Metastasis Rev.* 15:153-158 (1996).
Newman et al., "Cigarette Smoking and Pre-Eclampsia: Their Association and Effects on Clinical Outcomes," *J Matern. Fetal. Med.* 10:166-170 (2001).
Nishimoto et al., "Glomerular Hypertrophy in Preeclamptic Patients with Focal Segmental Glomerulosclerosis: A Morphometric Analysis," *Clin. Nephrol.* 51 :209-219 (1999).
Office Action for U.S. Appl. No. 10/624,809, dated Jun. 30, 2006. (13 pages).
Office Action for U.S. Appl. No. 10/624,809, dated May 1, 2007 (16 pages).
Office Action for U.S. Appl. No. 11/019,559, dated Jun. 6, 2006. (13 pages).
Office Action for U.S. Appl. No. 11/019,559, dated Mar. 22, 2007. (18 pages).
Office Action for U.S. Appl. No. 12/069,757, dated Nov. 12, 2009 (10 pages).
Office Action for U.S. Appl. No. 12/221,623, dated Dec. 14, 2009 (16 pages).
Office Action for U.S. Appl. No. 12/892,652, dated May 12, 2011 (87 pages).
Office Action for U.S. Appl. No. 10/624,809 dated Dec. 31, 2007.
Office Action for U.S. Appl. No. 10/771,518 dated Jun. 23, 2006.
Office Action for U.S. Appl. No. 10/771,518 dated Mar. 8, 2007.
Office Action for U.S. Appl. No. 11/019,559 dated Dec. 13, 2007.
Olofsson et al., "Vascular endothelial growth factor B (VEGF-8) binds to VEGF receptor-1 and regulates plasminogen activator activity in endothelial cells," Proc. Natl. Acad. Sci. USA 95: 11709-14 (1998).
Ong et al., "First-Trimester Maternal Serum Levels of Placental Growth Factor as Predictor of Preeclampsia and Fetal Growth Restriction," Obstet. Gynecol. 98:608-611 (2001).
Ostendorf et al., "VEGF (165) Mediates Glomerular Endothelial Repair," J. Clin. Invest. 104:913-23 (1999).
Page et al., "Excessive Placental Secretion of Neurokinin B During the Third Trimester Causes Pre-Eclampsia," *Nature* 405:797-800 (2000).
Parikh et al., "Putting Pressure on Pre-Eclampsia," Nat. Med. 14(8): 810-12 (2008).
Park et al., "An elevated maternal plasma, but not amniotic fluid, soluble fms-like tyrosine kinase-1 (sFlt-1) at the time of mid-trimester genetic amniocentesis is a risk factor for preeclampsia," Am. J. Obstet. Gynecol. 193: 984-9 (2005).
Park et al., "Placenta Growth Factor Potentiation of Vascular Endothelial Growth Factor Bioactivity, in Vitro and in Vivo, and High Affinity Binding to Flt-1 but not to Flk-1/KDR," J. Biol. Chem. 269: 25646-25654 (1994).
Parry et al., "Dinucleotide Repeat Polymorphisms within the Flt-1 Gene in Minimal Change Nephropathy," *Eur. J. Immunogenet.* 26:321-323 (1999).
Paternoster et al., "Markers of Tubular Damage in Pre-Eclampsia," *Minerva Ginecol.* 51 :373-377 (1999).
Polliotti et al., "Second-Trimester Maternal Serum Placental Growth Factor and Vascular Endothelial Growth Factor for Predicting Severe, Early-Onset Preeclampsia," *Obstet. Gynecol.* 101 :1266-1274 (2003).
Powers et al., "Maternal serum soluble fms-like tyrosine kinase 1 concentrations are not increased in early pregnancy and decrease more slowly postpartum in women who develop preeclampsia," Am. J. Obstet. Gynecol. 193: 185-191 (2005).
Qazi et al., "Soluble Fms-like Tyrosine Kinase Associated with Preeclampsia in Pregnancy in Systemic Lupus Erythematosus," J. Rheumatol. 35: 1-4 (2008).
Quirici et al., "Differentiation and Expansion of Endothelial Cells from Human Bone Marrow CD 133+ Cells," *Br. J. Haematol.* 115:186-194 (2001).
Rajakumar et al., "Extra-Placental Expression of Vascular Endothelial Growth Factor Receptor-1, (Flt-1) and Soluble Flt-1 (Sflt-1), by Peripheral Blood Mononuclear Cells (Pbmcs) in Normotensive and Preeclamptic Pregnant Women," Placenta 26(7): 563-573 (2004).
Rana et al., "Sequential Changes in Antiagiogenic Factors in Early Pregnancy and Risk of Developing Preeclampsia," Hypertension 50(1): 137-142 (2007).
Regnault et al., "Placental Expression of VEGF, PIGF and their Receptors in a Model of Placental Insufficiency-Intrauterine Growth Restriction (PI-IUGR)," *Placenta* 23:132-144 (2002).
Reply to Office Action for U.S. Appl. No. 12/069,757, dated Feb. 11, 2010 (17 pages).
Reply to Office Action for U.S. Appl. No. 10/624,809, filed Dec. 7, 2006.
Reply to Office Action for U.S. Appl. No. 10/624,809, filed Feb. 14, 2008.
Reply to Office Action for U.S. Appl. No. 10/624,809, filed Oct. 24, 2007.
Reply to Office Action for U.S. Appl. No. 10/771,518, filed Dec. 13, 2006.
Reply to Office Action for U.S. Appl. No. 10/771,518, filed Sep. 10, 2007.
Reply to Office Action for U.S. Appl. No. 11/019,559, filed Feb. 4, 2008.
Reply to Office Action for U.S. Appl. No. 11/019,559, filed Dec. 5, 2006.
Reply to Office Action for U.S. Appl. No. 11/019,559, filed Sep. 24, 2007.
Reuvekamp et al., "Selective deficit of angiogenic growth factors characterises pregnancies complicated by preeclampsia," BJOG 106: 1019-1022 (1999).
Roberts et al., "Pathogenesis and Genetics of Pre-Eclampsia," *Lancet* 357:53-56 (2001).
Roberts, "Endothelial dysfunction in preeclampsia," Semin. Reprod. Endocrinol. 16:5-15 (1998).
Roes et al., "High Levels of Urinary Vascular Endothelial Growth Factor in Women with Severe Preeclampsia," *Int. J. Biol. Markers* 19: 72-75 (2004).
Romero et al., "A Longitudinal Study of Angiogenic (Placental Growth Factor) and Anti-Angiogenic (Soluble Endoglin and Soluble Vascular Endothelial Growth Factor Receptor-1) Factors in Normal Pregnancy and Patients Destined to Develop Preeclampsia and Deliver a Small for Gestational Age Neonate," *J. Matern. Fetal Neonatal Med.* 21(1): 9-23 (2008).
Salahuddin et al., "Diagnostic Utility of Soluble Fms-Like Tyrosine Kinase 1 and Soluble Endoglin in Hypertensive Diseases of Pregnancy," *Am. J. Obstet. Gynecol.* 197(1):28.e1-6 (2007).
Sato et al., "Increased Pulmonary Vascular Contraction to Serotonin after Cardiopulmonary Bypass: Role of Cyclooxygenase," *J. Surg. Res.* 90:138-143 (2000).
Sawano et al., "Flt-1 but not KDR/Flk-1 tyrosine kinase is a receptor for placenta growth factor, which is related to vascular endothelial growth factor," Cell Growth Differ. 7: 213-221 (1996).

(56) References Cited

OTHER PUBLICATIONS

Shan et al., "Use of Circulating Antiangiogenic Factors to Differentiate Other Hypertensive Disorders From Preeclampsia in a Pregnant Woman on Dialysis," Am. J. Kidney Dis. 51(6): 1029-1032 (2008).
Sibai et al., "What we have learned about preeclampsia," Semin. Perinatol. 27:239-46 (2003).
Sibai, "Diagnosis and management of gestational hypertension and preeclampsia," Obstet. Gynecol. 102:181-92 (2003).
Signore et al., "Circulating Soluble Endoglin and Placental Abruption," *Prenat. Diagn.* 28(9): 852-858 (2008).
Simon et al., "Expression of vascular endothelial growth factor and its receptors in human renal ontogenesis and in adult kidney," Am J Physiol. 268:F240-50 (1995).
Steinberg et al., "Angiogenic Factors and Preeclampsia," *Thromb Res.* 123 Suppl. 2: S93-99 (2009).
Stillman et al., "The Glomerular Injury of Preeclampsia," *J. Am. Soc. Nephrol.* 18(8): 2281-2284 (2007).
Strevens et al., "Glomerular Endotheliosis in Normal Pregnancy and Pre-Eclampsia," *Br. J. Obstet. Gynaecol.* 110:831-836 (2003).
Su et al., "Decreased Maternal Serum Placenta Growth Factor in Early Second Trimester and Preeclampsia," *Obstet. Gynecol.* 97:898-904 (2001).
Sugimoto et al., "Neutralization of circulating vascular endothelial growth factor (VEGF) by anti-VEGF antibodies and soluble VEGF receptor 1(sFlt-1) induces proteinuria," J. Biol. Chem. 278:12605-12608 (2003).
Taylor et al., "Longitudinal Serum Concentrations of Placental Growth Factor: Evidence for Abnormal Placental Angiogenesis in Pathologic Pregnancies," *Am. J. Obstet. Gynecol.* 188:177-182 (2003).
Thadhani et al., "First trimester placental growth factor and soluble fms-like tyrosine kinase 1 and risk for preeclampsia," J. Clin. Endocrinol. Metab. 89:770-775 (2004).
Thadhani et al., "Hypertension During Pregnancy: A Disorder Begging for Pathophysiological Support," Hypertension 46(6): 1250-1251 (2005).
Thatcher et al., "Pregnancy induced hypertension: development of a model in the pregnant sheep," Am. J. Obstet. Gynecol. 155:201-7 (1986).
Tidwell et al., "Low Maternal Serum Levels of Placenta Growth Factor as an Antecedent of Clinical Preeclampsia," *Am. J. Obstet. Gynecol.* 184:1267-72 (2001).
Tischer et al., "The Human Gene for Vascular Endothelial Growth Factor," *J. Biol. Chem.* 266:11947-11954 (1991).
Tjoa et al., "Angiogenic Factors and Preeclampsia," *Front Biosci.* 12: 2395-2402 (2007).
Tjoa et al., "Plasma Placenta Growth Factor Levels in Midtrimester Pregnancies," *Obstet. Gynecol.* 98:600-607 (2001).
Torry et al., "Expression and Function of Placenta Growth Factor: Implications for Abnormal Placentation," *J. Soc. Gynecol. Investig.* 10:178-88 (2003).
Torry et al., "Preeclampsia is Associated with Reduced Serum Levels of Placenta Growth Factor," *Am. J. Obstet. Gynecol.* 179: 1539-1544 (1998).
Traver et al., "Walking the Walk: Migration and other Common Themes in Blood and Vascular Development," Cell 108:731-734 (2002).
Tsatsaris et al., "Overexpression of the Soluble Vascular Endothelial Growth Factor Receptor in Preeclamptic Patients: Pathophysiological Consequences," *J Clin. Endocrinol. Metab.* 88:5555-5563 (2003).
Tucci et al., "rhVEGF and Experimental Rat Skin Flaps: Systemic or Local Administration and Morphological Characteristics," *Int. J. Artif. Organs* 24:743-751 (2001).
Vuorela, "Vascular Endothelial Growth Factor, Its Receptors, and the Tie Receptor in Normal and Complicated Pregnancy," Department of Obstetrics and Gynecology, Helsinki University Central Hospital, University of Helsinki, Finland (2000).
Walker, "Pre-Eclampsia," *Lancet* 356:1260-1265 (2000).
Walsh et al., "Computer modeling of the receptor-binding domains of VEGF and PlGF," Protein Eng. 10: 389-98 (1997).
Wang et al., "Preeclampsia: The Role of Angiogenic Factors in Its Pathogenesis," *Physiology* 24: 147-158 (2009).
Widmer et al., "Mapping the Theories of Preeclampsia and the Role of Angiogenic Factors: A Systematic Review," *Obstet. Gynecol.* 109(1): 168-180 (2007).
Wiesmann et al., "Crystal structure at 1.7 A resolution of VEGF in complex with domain 2 of the Flt-1 receptor," Cell. 91:695-704 (1997).
Wolf et al., "Circulating Levels of the Antiangiogenic Marker Sflt-1 are Increased in First Versus Second Pregnancies," Am. J. Obstet. Gynecol. 193(1): 16-22 (2005).
Yang et al., "A Randomized Trial of Bevacizumab, an Anti-Vascular Endothelial Growth Factor Antibody, for Metastatic Renal Cancer," *N. Engl. J. Med.* 349:427-434 (2003).
Yang et al., "sFlt-1 Gene-Transfected Fibroblasts: A Wound-Specific Gene Therapy Inhibits Local Cancer Recurrence," *Cancer Res.* 61:7840-7845 (2001).
Zhang et al., "Birth-Weight-for-Gestational-Age-Patterns by Race, Sex, and Parity in the United States Population," *Obstet. Gynecol.* 86:200-208 (1995).
Zhou et al., "Preeclampsia is Associated with Failure of Human Cytotrophoblasts to Mimic a Vascular Adhesion Phenotype. One Cause of Defective Endovascular Invasion in this Syndrome?" *J. Clin. Invest* 99:2152-2164 (1997).
Zhou et al., "Vascular Endothelial Growth Factor Ligands and Receptors That Regulate Human Cytotrophoblast Survival are Dysregulated in Severe Preeclampsia and Hemolysis, Elevated Liver Enzymes, and Low Platelets Syndrome," Am. J. Pathol. 160: 1405-1423 (2002).
Carr et al., "Hemodynamically-directed atenolol therapy is associated with a blunted rise in maternal sFLT-1 levels during pregnancy," Hypertens Pregnancy. 28(1):42-55 (2009).
Cohen et al., "Circulating levels of the antiangiogenic marker soluble Fms-like tyrosine kinase 1 are elevated in women with pregestational diabetes and preeclampsia: angiogenic markers in preeclampsia and preexisting diabetes," Diabetes Care. 30(2):375-7 (2007).
Hladunewich et al., "Pathophysiology of the clinical manifestations of preeclampsia," Clin J Am Soc Nephrol. 2(3):543-9 (2007).
Holston et al., "Circulating angiogenic factors in gestational proteinuria without hypertension," Am J Obstet Gynecol. 392(4):e1-10 (2009).
Mutter et al., "Molecular mechanisms of preeclampsia," Microvasc Res. 75(1):1-8 (2008).
Foreign Search Report for Application No. SG 200500265-4 dated Oct. 7, 2005.

\* cited by examiner

N t=0: 158497± 11929

N t=48: 160946± 26892

N t=0 + sFlt-1: 68215± 3019

P t=0: 87505± 13007

P t=48: 237708± 15722.75

P t=0+VEGF+PlGF:185088±33647

METHODS OF TREATING PRE-ECLAMPSIA OR ECLAMPSIA

CROSS REFERENCE TO RELATED APPLICATIONS

This application is a divisional of and claims priority from U.S. patent application Ser. No. 12/069,757, filed Feb. 12, 2008, which is a divisional of Ser. No. 10/771,518, filed Feb. 4, 2004, now U.S. Pat. No. 7,335,362, which is a continuation-in-part of U.S. patent application Ser. No. 10/624,809, filed Jul. 21, 2003, now U.S. Pat. No. 7,407,659, which claims the benefit of U.S. Provisional Application Nos. 60/397,481, filed on Jul. 19, 2002; 60/451,796, filed on Mar. 3, 2003; and 60/467,390 filed on May 2, 2003, each of which is herein incorporated by reference.

FIELD OF THE INVENTION

In general, this invention relates to the detection and treatment of subjects having pre-eclampsia or eclampsia.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the $20^{th}$ week of pregnancy and are usually detected by routine ing of the woman's blood pressure and urine. However, these monitoring methods are ineffective for diagnosis of the syndrome at an early stage, which could reduce the risk to the subject or developing fetus, if an effective treatment were available.

Currently there are no known cures for pre-eclampsia. Pre-eclampsia can vary in severity from mild to life threatening. A mild form of pre-eclampsia can be treated with bed rest and frequent monitoring. For moderate to severe cases, hospitalization is recommended and blood pressure medication or anticonvulsant medications to prevent seizures are prescribed. If the condition becomes life threatening to the mother or the baby the pregnancy is terminated and the baby is delivered pre-term.

The proper development of the fetus and the placenta is mediated by several growth factors. One of these growth factors is vascular endothelial growth factor (VEGF). VEGF is an endothelial cell-specific mitogen, an angiogenic inducer, and a mediator of vascular permeability. VEGF has also been shown to be important for glomerular capillary repair. VEGF binds as a homodimer to one of two homologous membrane-spanning tyrosine kinase receptors, the fms-like tyrosine kinase (Flt-1) and the kinase domain receptor (KDR), which are differentially expressed in endothelial cells obtained from many different tissues. Flt-1, but not KDR, is highly expressed by trophoblast cells which contribute to placental formation. Placental growth factor (PlGF) is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not the KDR receptor. Both PlGF and VEGF contribute to the mitogenic activity and angiogenesis that are critical for the developing placenta.

A soluble form of the Flt-1 receptor (sFlt-1) was recently identified in a cultured medium of human umbilical vein endothelial cells and in vivo expression was subsequently demonstrated in placental tissue. sFlt-1 is a splice variant of the Flt-1 receptor which lacks the transmembrane and cytoplasmic domains. sFlt-1 binds to VEGF with a high affinity but does not stimulate mitogenesis of endothelial cells. sFlt-1 is believed to act as a "physiologic sink" to down-regulate VEGF signaling pathways. Regulation of sFlt-1 levels therefore works to modulate VEGF and VEGF signaling pathways. Careful regulation of VEGF and PlGF signaling pathways is critical for maintaining appropriate proliferation, migration, and angiogenesis by trophoblast cells in the developing placenta. There is a need for methods of accurately diagnosing subjects at risk for or having pre-eclampsia, particularly before the onset of the most severe symptoms. A treatment is also needed.

SUMMARY OF THE INVENTION

We have discovered a means for diagnosing and effectively treating pre-eclampsia and eclampsia prior to the development of symptoms.

Using gene expression analysis, we have discovered that levels of sFlt-1 are markedly elevated in placental tissue samples from pregnant women suffering from pre-eclampsia. sFlt-1 is known to antagonize VEGF and PlGF by acting as a "physiologic sink" and, in pre-eclamptic or eclamptic women, sFlt-1 may be depleting the placenta of necessary amounts of these essential angiogenic and mitogenic factors. Excess sFlt-1 may also lead to eclampsia by disrupting the endothelial cells that maintain the blood-brain barrier and/or endothelial cells lining the choroids plexus of the brain thus leading to cerebral edema and the seizures seen in eclampsia. In the present invention, compounds that increase VEGF and PlGF levels are administered to a subject to treat or prevent pre-eclampsia or eclampsia by countering the effects of elevated sFlt-1. In addition, antibodies directed to sFlt-1 are used to competitively inhibit binding of VEGF or PlGF to sFlt-1, thereby increasing the levels of free VEGF and PlGF. RNA interference and antisense nucleobase oligomers are also used to decrease the levels of sFlt-1. Finally, the present invention provides for the use and monitoring of sFlt-1, VEGF, and PlGF as detection tools for early diagnosis and management of pre-eclampsia or eclampsia, or a predisposition thereto, or a cardiovascular condition, or a predisposition thereto.

Accordingly, in one aspect, the invention provides a method of treating or preventing pre-eclampsia or eclampsia in a subject by administering to the subject a compound capable of binding to sFlt-1, where the administering is for a time and in an amount sufficient to treat or prevent pre-eclampsia or eclampsia in a subject. In a preferred embodiment, the compound is a purified sFlt-1 antibody or antigen-binding fragment thereof.

In a related aspect, the invention provides a method of treating or preventing pre-eclampsia or eclampsia in a subject by administering to the subject a compound (e.g., nicotine, theophylline, adenosine, nifedipine, minoxidil, or magnesium sulfate) that increases the level of a growth factor capable of binding to sFlt-1, where the administering is for a time and in an amount sufficient to treat or prevent pre-eclampsia or eclampsia in a subject.

In yet another related aspect, the invention provides a method of treating or preventing pre-eclampsia or eclampsia in a subject by administering to the subject an antisense nucleobase oligomer complementary to at least a portion of an sFlt-1 nucleic acid sequence, where the administering is sufficient to treat or prevent pre-eclampsia or eclampsia in a subject. In one embodiment, the antisense nucleobase oligomer is 8 to 30 nucleotides in length.

In another related aspect, the invention provides a method of treating or preventing pre-eclampsia or eclampsia in a subject. The method involves the step of administering to the subject a double stranded RNA (dsRNA) that contains at least a portion of an sFlt-1 nucleic acid sequence, where the administering is sufficient to treat or prevent pre-eclampsia or eclampsia in the subject. In one embodiment, the double stranded RNA is processed into small interfering RNAs (siRNAs) 19 to 25 nucleotides in length.

In various embodiments of the above aspects, the candidate compound is a growth factor such as vascular endothelial growth factor (VEGF), including all isoforms such as VEGF189, VEGF121, or VEGF165; placental growth factor (PlGF), including all isoforms; or fragments thereof. In preferred embodiments, the candidate compound is an antibody that binds sFlt-1. In other embodiments of the above aspects, the method further involves administering to a subject an anti-hypertensive compound. In still other embodiments of the above aspects, the subject is a pregnant human, a post-partum human, or a non-human (e.g., a cow, a horse, a sheep, a pig, a goat, a dog, or a cat).

In another aspect, the invention provides a method of treating or preventing pre-eclampsia or eclampsia. The method involves administering to a subject in need of such treatment an effective amount of a pharmaceutical composition comprising a VEGF or PlGF polypeptide. In one embodiment, the composition contains a VEGF polypeptide. In another embodiment, the composition contains a PlGF polypeptide.

In a related aspect, the invention provides a method of treating or preventing pre-eclampsia or eclampsia. This method involves administering to a subject in need of such treatment an effective amount of a pharmaceutical composition comprising a nucleic acid molecule encoding VEGF or PlGF. In one embodiment, the composition contains a VEGF nucleic acid molecule. In another embodiment, the composition contains a PlGF nucleic acid molecule.

In another related aspect, the invention provides a method of treating or preventing pre-eclampsia or eclampsia in a subject. The method involves the step of administering to the subject a compound (e.g., chemical compound, polypeptide, peptide, antibody, or a fragment thereof) that inhibits growth factor binding to an sFlt-1 polypeptide, where the administering is sufficient to treat or prevent pre-eclampsia or eclampsia in a subject. In one embodiment, the compound binds to sFlt-1 and blocks growth factor binding.

In various embodiments of the above aspects, the method further involves the step of administering to a subject an anti-hypertensive compound (e.g., adenosine, nifedipine, minoxidil, and magnesium sulfate). In other embodiments of the above aspects, the subject is a pregnant human, a post-partum human, or a non-human (e.g., a cow, a horse, a sheep, a pig, a goat, a dog, or a cat).

In another aspect, the invention provides a method of diagnosing a subject as having, or having a propensity to develop, pre-eclampsia or eclampsia, the method involves measuring the level of sFlt-1, VEGF, or PlGF polypeptide in a sample from the subject.

In a related aspect, the invention provides a method of diagnosing a subject as having, or having a propensity to develop, pre-eclampsia or eclampsia, by determining the levels of at least two of sFlt-1, VEGF, or PlGF polypeptide in a sample from a subject and calculating the relationship between the levels of sFlt-1 VEGF, or PlGF using a metric, where an alteration in the subject sample relative to a reference diagnoses pre-eclampsia or eclampsia in a subject. In preferred embodiments, the method also includes determining the body mass index (BMI), the gestational age (GA) of the fetus, or both and including the BMI or GA or both in the metric. In one embodiment, the metric is a pre-eclampsia anti-angiogenic index (PAAI): [sFlt-1/VEGF+ PlGF], where the PAAI is used as an indicator of anti-angiogenic activity. In one embodiment, a PAAI greater than 10, more preferably greater than 20, is indicative of pre-eclampsia or eclampsia. In another embodiment, the levels of sFlt-1, VEGF, or PlGF polypeptide is determined by an immunological assay, such as an ELISA.

In various embodiments of the above aspects, the sample is a bodily fluid, such as serum or urine. In one embodiment, a level of sFlt-1 greater than 2 ng/ml is indicative of pre-eclampsia or eclampsia. In preferred embodiments of the above aspects, the level of sFlt-1 polypeptide measured is the level of free, bound, or total sFlt-1 polypeptide. In additional embodiments, the sFlt-1 polypeptide can also include sFlt-1 fragments, degradation products, or enzymatic cleavage products. In other preferred embodiments of the above aspects, the level of VEGF or PlGF is the level of free VEGF or PlGF.

In another aspect, the invention provides a method of diagnosing a subject as having, or having a propensity to develop, pre-eclampsia or eclampsia. This method involves measuring the level of sFlt-1, VEGF, or PlGF nucleic acid molecule in a sample from the subject and comparing it to a reference sample, where an alteration in the levels diagnoses pre-eclampsia or eclampsia in the subject, or diagnoses a propensity to develop pre-eclampsia or eclampsia.

In another aspect, the invention provides a method of diagnosing a subject as having, or having a propensity to develop, pre-eclampsia or eclampsia. This method involves determining the nucleic acid sequence of a sFlt-1, VEGF, or PlGF gene in a subject and comparing it to a reference sequence, where an alteration in the subject's nucleic acid sequence that changes the level or the biological activity of the gene product in the subject diagnoses the subject with pre-eclampsia or eclampsia, or a propensity to develop pre-eclampsia or eclampsia. In one embodiment, the alteration is a polymorphism in the nucleic acid sequence.

In various embodiments of the above aspects, the sample is a bodily fluid (e.g., urine, amniotic fluid, serum, plasma, or cerebrospinal fluid) of the subject in which the sFlt-1, VEGF, or PlGF is normally detectable. In additional embodiments, the sample is a tissue or a cell. Non-limiting examples include placental tissue or placental cells, endothelial cells, leukocytes, and monocytes. In other embodiments of the above aspects, the subject is a non-pregnant human, a pregnant human, or a post-partum human. In other embodiments of the above aspects, the subject is a non-human (e.g., a cow, a horse, a sheep, a pig, a goat, a dog, or a cat). In one embodiment, the subject is a non-pregnant human and the method is used to diagnose a propensity to develop pre-eclampsia or eclampsia. In other embodiments of the above aspects, at least one of the levels measured is the level of sFlt-1 (free, bound, or total). In additional embodiments, the level of sFlt-1 measured includes the level of sFlt-1 degradation products or enzymatic cleavage products. In other embodiments of the above aspects, when the level of VEGF is measured then the level of sFlt-1 or PlGF is also measured. In additional embodiments, the BMI or GA or both is also measured. In various embodiments of the above aspects, an increase in the level of sFlt-1 nucleic acid or polypeptide relative to a reference is a diagnostic indicator of pre-eclampsia or eclampsia. In other embodiments of the above aspects, a decrease in the level of free VEGF polypeptide or VEGF nucleic acid relative to a reference is a diagnostic indicator of pre-eclampsia or eclampsia. In other embodiments of the above aspects, a decrease in the level of free PlGF polypeptide or PlGF nucleic acid relative to a reference is a diagnostic indicator of pre-eclampsia or eclampsia.

In additional embodiments of the above aspects, the levels are measured on two or more occasions and a change in the levels between the measurements is a diagnostic indicator of pre-eclampsia or eclampsia. In one preferred embodiment, the level of sFlt-1 increases from the first measurement to the next measurement. In another preferred embodiment, the level of VEGF or PlGF decreases from the first measurement to the next measurement.

In another aspect, the invention provides a diagnostic kit for the diagnosis of pre-eclampsia or eclampsia in a subject comprising a nucleic acid sequence, or fragment thereof, selected from the group consisting of sFlt-1, VEGF, and PlGF nucleic acid molecule, or a sequence complementary thereto, or any combination thereof. In a preferred embodiment, the kit comprises at least two probes for the detection of an sFlt-1, VEGF, or PlGF nucleic acid molecule.

Any of the diagnostic methods described herein can also be used to monitor the pre-eclampsia or eclampsia in the subject. In preferred embodiments, the diagnostic methods are used to monitor the subject during therapy or to determine effective therapeutic dosages. In one embodiment, a decrease in the level of sFlt-1 polypeptide or nucleic acid measured during or after administering therapy relative to the value before therapy indicates an improvement in the pre-eclampsia or eclampsia. In a preferred embodiment, a level of sFlt-1 polypeptide less than 2 ng/ml indicates an improvement in the pre-eclampsia or eclampsia. In another embodiment, a therapeutic compound is administered in a dose such that the level of sFlt-1 polypeptide is less than 2 ng/ml. In another embodiment, an increase in the level of VEGF or PlGF polypeptide or nucleic acid measured during or after administering therapy relative to the value before therapy indicates an improvement in the pre-eclampsia or eclampsia. In yet another embodiment, a decrease in the PAAI value of a subject indicates an improvement in the pre-eclampsia or eclampsia. In preferred embodiments, the PAAI is less than 20, more preferably less than 10. A decrease in the PAAI can also indicates an effective dosage of a therapeutic compound. In one example, a therapeutic compound is administered in a dose such that the PAAI is less than 20. In another example, a therapeutic compound is administered in a dose such that the PAAI is less than 10. In preferred embodiments, the measuring of the levels of sFlt-1, PlGF, or VEGF is done on two or more occasions and a change in the levels between measurements is used to monitor therapy or to determine therapeutic dosages of a compound.

In a related aspect, the invention provides a kit for the diagnosis of pre-eclampsia or eclampsia in a subject comprising a means of detecting a sFlt-1, VEGF, or PlGF polypeptide, and any combination thereof. In one embodiment, the means of detecting is selected from the group consisting of an immunological assay, an enzymatic assay, and a colorimetric assay. In other embodiments of the above aspects, the kit diagnoses a propensity to develop pre-eclampsia or eclampsia in a pregnant or a non-pregnant subject. In preferred embodiments of the above aspects, the kit detects sFlt-1 or PlGF. In other preferred embodiments of the above aspects, when the kit detects VEGF then sFlt-1 or PlGF is also detected. In additional preferred embodiments, the kit is used to detect VEGF, sFlt-1 and PlGF and to determine the PAAI of the sample.

In preferred embodiments, the diagnostic kits include a label or instructions for the intended use of the kit components. In one embodiment, the diagnostic kit is labeled or includes instructions for use in the diagnosis of pre-eclampsia or eclampsia, or a propensity to develop pre-eclampsia or eclampsia in a subject. In another embodiment, the diagnostic kit is labeled or includes instructions for use in the diagnosis of a cardiovascular condition or a propensity to develop a cardiovascular condition. In yet another embodiment, the diagnostic kit is labeled or includes instructions for use in therapeutic monitoring or therapeutic dosage determination. In a preferred embodiment, the diagnostic kit includes a label or instructions for the use of the kit to determine the PAAI of the subject sample and to compare the PAAI to a reference sample value. It will be understood that the reference sample values will depend on the intended use of the kit. For example, the sample can be compared to a normal PAAI reference value, wherein an increase in the PAAI is indicative of pre-eclampsia or eclampsia, or a propensity to develop pre-eclampsia or eclampsia. In another example, a kit used for therapeutic monitoring can have a reference PAAI value that is indicative of pre-eclampsia or eclampsia, wherein a decrease in the PAAI value of the subject sample relative to the reference sample can be used to indicate therapeutic efficacy or effective dosages of therapeutic compounds.

In a related aspect, the invention features a device for diagnosing a subject as having or having a propensity to develop pre-eclampsia or eclampsia. The device includes a means for comparing the levels of at least two of sFlt-1, VEGF, and PlGF polypeptides in a sample from a subject relative to a reference sample, wherein an alteration in the levels of at least two of sFlt-1, VEGF, and PlGF diagnoses pre-eclampsia or eclampsia or a propensity to develop pre-eclampsia or eclampsia in the subject. In a preferred embodiment the device includes a means for using a metric to compare the levels as at least two of sFlt-1, VEGF, and PlGF polypeptides.

In a related aspect, the invention features a device for diagnosing a subject as having or having a propensity to develop pre-eclampsia or eclampsia. The device includes a means for comparing the levels of at least two of sFlt-1, VEGF, and PlGF nucleic acid molecules in a sample from a subject relative to a reference sample, wherein an alteration in the levels of at least two of sFlt-1, VEGF, and PlGF diagnoses pre-eclampsia or eclampsia or a propensity to develop pre-eclampsia or eclampsia in the subject. In a preferred embodiment the device includes a means for using a metric to compare the levels as at least two of sFlt-1, VEGF, and PlGF nucleic acid molecules.

In another aspect, the invention provides a method of identifying a compound that ameliorates pre-eclampsia or eclampsia. The method involves contacting a cell that expresses a sFlt-1, VEGF, or PlGF nucleic acid molecule with a candidate compound, and comparing the level of expression of the nucleic acid molecule in the cell contacted by the candidate compound with the level of expression in a control cell not contacted by the candidate compound, where an alteration in expression of the sFlt-1, VEGF, or PlGF nucleic acid molecule identifies the candidate compound as a compound that ameliorates pre-eclampsia or eclampsia.

In one embodiment, the alteration is a decrease in the level of sFlt-1. In other embodiments, the alteration is an increase in the level of VEGF or PlGF. In other embodiments, the alteration is in transcription or in translation. In another embodiment, when the method identifies a candidate compound that increases the expression of VEGF, the candidate compound also increases the expression of PlGF or decreases the expression of sFlt-1.

In another aspect, the invention provides a pharmaceutical composition including a VEGF or PlGF polypeptide or portion thereof, formulated in a pharmaceutically acceptable carrier.

In a related aspect, the invention provides a pharmaceutical composition comprising a PlGF nucleic acid molecule, or portion thereof, formulated in a pharmaceutically acceptable carrier. In one embodiment, the composition further contains a VEGF nucleic acid molecule, or portion thereof.

In another aspect, the invention provides a composition comprising a purified antibody or antigen-binding fragment thereof that specifically binds sFlt-1. In one preferred embodiment, the antibody prevents binding of a growth factor to sFlt-1. In another embodiment, the antibody is a monoclonal antibody. In other preferred embodiments, the antibody or antigen-binding fragment thereof is a human or humanized antibody. In other embodiments, the antibody lacks an Fc portion. In still other embodiments, the antibody is an F(ab')$_2$, an Fab, or an Fv structure. In other embodiments, the antibody or antigen-binding fragment thereof is present in a pharmaceutically acceptable carrier.

In another aspect, the invention provides a method of identifying a compound that ameliorates pre-eclampsia or eclampsia. This method involves contacting a cell that expresses an sFlt-1, VEGF, or PlGF polypeptide with a candidate compound, and comparing the level of expression of the polypeptide in the cell contacted by the candidate compound with the level of polypeptide expression in a control cell not contacted by the candidate compound, where an alteration in the expression of the sFlt-1, VEGF, or PlGF polypeptide identifies the candidate compound as a compound that ameliorates pre-eclampsia or eclampsia.

In one embodiment, the alteration in expression is assayed using an immunological assay, an enzymatic assay, or an immunoassay. In one embodiment, the alteration in expression is a decrease in the level of sFlt-1. In another embodiment, the alteration in expression is an increase in the level of VEGF or PlGF.

In another aspect, the invention provides a method of identifying a compound that ameliorates pre-eclampsia or eclampsia. The method involves contacting a cell that expresses an sFlt-1, VEGF, or PlGF polypeptide with a candidate compound, and comparing the biological activity of the polypeptide in the cell contacted by the candidate compound with the level of biological activity in a control cell not contacted by the candidate compound, where an increase in the biological activity of the sFlt-1, VEGF, or PlGF polypeptide identifies the candidate compound as a compound that ameliorates pre-eclampsia or eclampsia. In one embodiment, the increase in biological activity is assayed using an immunological assay, an enzymatic assay, or an immunoassay. In one embodiment, the alteration in expression is a decrease in the activity of sFlt-1. In another embodiment, the alteration in expression is an increase in the activity of VEGF or PlGF.

In another aspect, the invention provides a method of identifying a compound that ameliorates pre-eclampsia or eclampsia. The method involves detecting binding between an sFlt-1 polypeptide and a growth factor in the presence of a candidate compound, where a decrease in the binding, relative to binding between the sFlt-1 polypeptide and the growth factor in the absence of the candidate compound identifies the candidate compound as a compound that ameliorates pre-eclampsia or eclampsia. In one embodiment, the growth factor is VEGF. In another embodiment, the growth factor is PlGF.

In another aspect, the invention provides a method of identifying a polypeptide, or fragment thereof, that prevents binding between an sFlt-1 polypeptide and a growth factor. The method involves detecting binding between an sFlt-1 polypeptide and a growth factor in the presence of the candidate polypeptide, where a decrease in the binding, relative to binding between the sFlt-1 polypeptide and the growth factor in the absence of the candidate polypeptide identifies the candidate polypeptide as a polypeptide that prevents binding between an sFlt-1 polypeptide and a growth factor. In one embodiment, the growth factor is VEGF. In another embodiment, the growth factor is PlGF.

In another aspect, the invention provides a method of identifying a compound that ameliorates pre-eclampsia or eclampsia, comprising detecting binding of an sFlt-1 polypeptide and a candidate compound, where a compound that binds the sFlt-1 polypeptide ameliorates pre-eclampsia or eclampsia.

In a related aspect, the invention provides a compound identified according to the previous aspect, where the compound is a polypeptide that specifically binds an sFlt-1 polypeptide and prevents the sFlt-1 polypeptide from binding VEGF or PlGF. In one preferred embodiment, the polypeptide is an antibody. In another preferred embodiment, the polypeptide is a fragment of sFlt-1, VEGF, or PlGF.

In preferred embodiments of the above aspects, the compound that ameliorates pre-eclampsia or eclampsia decreases the expression levels or biological activity of sFlt-1. In preferred embodiments of the above aspects, the compound that ameliorates pre-eclampsia or eclampsia increases the expression levels or biological activity of VEGF or PlGF.

In yet another aspect, the invention features a method of diagnosing a subject as having or having a propensity to develop a cardiovascular condition. This method involves measuring the level of sFlt-1 polypeptide in a sample from the subject and comparing it to a reference sample, wherein an alteration in the subject sample level diagnoses a cardiovascular condition or a propensity to develop a cardiovascular condition in the subject. In preferred embodiments, the measuring is done using an immunological assay such as an ELISA.

In a related aspect, the invention features a method of diagnosing a subject as having or having a propensity to develop a cardiovascular condition. This method includes measuring the level of sFlt-1 nucleic acid molecule in a sample from the subject and comparing it to a reference sample, wherein an alteration in the level diagnoses a cardiovascular condition or a propensity to develop a cardiovascular condition in the subject.

In preferred embodiments of the above aspects, the subject is a female that is or has been pregnant. In additional preferred embodiments, the female subject has a history of pre-eclampsia or eclampsia. In additional preferred embodiments, the reference sample is taken from a female that does not have a history of pre-eclampsia or eclampsia.

In a related aspect, the invention features a method of diagnosing a subject as having or having a propensity to develop a cardiovascular condition. This method includes determining the nucleic acid sequence of a sFlt-1, VEGF, or PlGF gene in a sample from the subject and comparing it to a reference sequence, wherein an alteration in the subject's nucleic acid sequence that is an alteration that changes the expression level or biological activity of the gene product in the subject diagnoses a cardiovascular condition or a propensity to develop a cardiovascular condition in the subject.

In preferred embodiments of the above aspects, the sample is a cell, a tissue, or a bodily fluid in which sFlt-1 is normally detectable. Preferred samples include urine, amniotic fluid, serum, plasma, cerebrospinal fluid, and placental cells or tissue. In preferred embodiments of the above aspects, the cardiovascular condition is selected from the group consisting of atherosclerosis, primary myocardial infarction, secondary myocardial infarction, angina pectoris, congestive heart failure, sudden cardiac death, cerebral infarction, restenosis, syncope, ischemia, reperfusion injury, vascular occlusion, carotid obstructive disease, and transient ischemic attack For the purpose of the present invention, the following abbreviations and terms are defined below.

By "alteration" is meant a change (increase or decrease) in the expression levels of a gene or polypeptide as detected by standard art known methods such as those described above. As used herein, an alteration includes a 10% change in expression levels, preferably a 25% change, more preferably a 40% change, and most preferably a 50% or greater change in expression levels. "Alteration" can also indicate a change (increase or decrease) in the biological activity of any of the polypeptides of the invention (e.g., sFlt-1, VEGF, or PlGF). Examples of biological activity for PlGF or VEGF include binding to receptors as measured by immunoassays, ligand binding assays or Scatchard plot analysis, and induction of cell proliferation or migration as measured by BrdU labeling, cell counting experiments, or quantitative assays for DNA synthesis such as $^3$H-thymidine incorporation. Examples of biological activity for sFlt-1 include binding to PlGF and VEGF as measured by immunoassays, ligand binding assays, or Scatchard plot analysis. Additional examples of assays for biological activity for each of the polypeptides are described herein. As used herein, an alteration includes a 10% change in biological activity, preferably a 25% change, more preferably a 40% change, and most preferably a 50% or greater change in biological activity.

By "antisense nucleobase oligomer" is meant a nucleobase oligomer, regardless of length, that is complementary to the coding strand or mRNA of an sFlt-1 gene. By a "nucleobase oligomer" is meant a compound that includes a chain of at least eight nucleobases, preferably at least twelve, and most preferably at least sixteen bases, joined together by linkage groups. Included in this definition are natural and non-natural oligonucleotides, both modified and unmodified, as well as oligonucleotide mimetics such as Protein Nucleic Acids, locked nucleic acids, and arabinonucleic acids. Numerous nucleobases and linkage groups may be employed in the nucleobase oligomers of the invention, including those described in U.S. Patent Application Nos. 20030114412 and 20030114407, incorporated herein by reference. The nucleobase oligomer can also be targeted to the translational start and stop sites. Preferably the antisense nucleobase oligomer comprises from about 8 to 30 nucleotides. The antisense nucleobase oligomer can also contain at least 40, 60, 85, 120, or more consecutive nucleotides that are complementary to sFlt-1 mRNA or DNA, and may be as long as the full-length mRNA or gene.

By "body mass index" is meant a number, derived by using height and weight measurements, that gives a general indication of whether or not weight falls within a healthy range. The formula generally used to determine the body mass index is a person's weight in kilograms divided by a person's height in meters squared or weight (kg)/(height (m))$^2$.

By "cardiovascular condition" is meant an event or disorder of the cardiovascular system. Non-limiting examples of cardiovascular conditions include atherosclerosis, primary myocardial infarction, secondary myocardial infarction, angina pectoris (including both stable and unstable angina), congestive heart failure, sudden cardiac death, cerebral infarction, restenosis, syncope, ischemia, reperfusion injury, vascular occlusion, carotid obstructive disease, transient ischemic attack, and the like.

By "compound" is meant any small molecule chemical compound, antibody, nucleic acid molecule, or polypeptide, or fragments thereof.

By "chimeric antibody" is meant a polypeptide comprising at least the antigen-binding portion of an antibody molecule linked to at least part of another protein (typically an immunoglobulin constant domain).

By "double-stranded RNA (dsRNA)" is meant a ribonucleic acid molecule comprised of both a sense and an anti-sense strand. dsRNAs are typically used to mediate RNA interference.

By "expression" is meant the detection of a gene or polypeptide by standard art known methods. For example, polypeptide expression is often detected by western blotting, DNA expression is often detected by Southern blotting or polymerase chain reaction (PCR), and RNA expression is often detected by northern blotting, PCR, or RNAse protection assays.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "gestational age" is meant a reference to the age of the fetus, counting from the first day of the mother's last menstrual period usually referred to in weeks.

By a "history of pre-eclampsia or eclampsia" is meant a previous diagnosis of pre-eclampsia or eclampsia or pregnancy induced hypertension in the subject themselves or in a related family member.

By "homologous" is meant any gene or protein sequence that bears at least 30% homology, more preferably 40%, 50%, 60%, 70%, 80%, and most preferably 90% or more homology to a known gene or protein sequence over the length of the comparison sequence. A "homologous" protein can also have at least one biological activity of the comparison protein. For polypeptides, the length of comparison sequences will generally be at least 16 amino acids, preferably at least 20 amino acids, more preferably at least 25 amino acids, and most preferably 35 amino acids or more. For nucleic acids, the length of comparison sequences will generally be at least 50 nucleotides, preferably at least 60 nucleotides, more preferably at least 75 nucleotides, and most preferably at least 110 nucleotides. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein at issue.

By "humanized antibody" is meant an immunoglobulin amino acid sequence variant or fragment thereof that is capable of binding to a predetermined antigen. Ordinarily, the antibody will contain both the light chain as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin (the "import" sequences).

Generally, a humanized antibody has one or more amino acid residues introduced into it from a source that is non-human. In general, the humanized antibody will comprise substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally will comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains.

The FR and CDR regions of the humanized antibody need not correspond precisely to the parental sequences, e.g., the import CDR or the consensus FR may be mutagenized by substitution, insertion or deletion of at least one residue so that the CDR or FR residue at that site does not correspond to either the consensus or the import antibody. Such mutations, however, will not be extensive. Usually, at least 75%, preferably 90%, and most preferably at least 95% of the humanized antibody residues will correspond to those of the parental FR and CDR sequences. By "hybridize" is meant pair to form a double-stranded molecule between complementary polynucleotide sequences, or portions thereof, under various conditions of stringency. (See, e.g., Wahl and Berger (1987) *Methods Enzymol.* 152:399; Kimmel, *Methods Enzymol.* 152:507, 1987.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196: 180, 1977); Grunstein and Hogness (*Proc. Natl. Acad. Sci., USA* 72:3961, 1975); Ausubel et al. (*Current Protocols in Molecular Biology*, Wiley Interscience, New York, 2001); Berger and Kimmel (*Guide to Molecular Cloning Techniques*, 1987, Academic Press, New York); and Sambrook et al., *Molecular Cloning: A Laboratory Manual*, Cold Spring Harbor Laboratory Press, New York.

By "intrauterine growth retardation (IUGR)" is meant a syndrome resulting in a birth weight which is less that 10 percent of the predicted fetal weight for the gestational age of the fetus. The current World Health Organization criterion for low birth weight is a weight less than 2,500 gm (5 lbs. 8 oz.) or below the $10^{th}$ percentile for gestational age according to U.S. tables of birth weight for gestational age by race, parity, and infant sex (Zhang and Bowes, Obstet. Gynecol. 86:200-208, 1995). These low birth weight babies are also referred to as "small for gestational age (SGA)". Pre-eclampsia is a condition known to be associated with IUGR or SGA.

By "metric" is meant a measure. A metric may be used, for example, to compare the levels of a polypeptide or nucleic acid molecule of interest. Exemplary metrics include, but are not limited to, mathematical formulas or algorithms, such as ratios. The metric to be used is that which best discriminates between levels of sFlt-1, VEGF, or PlGF in a subject having pre-eclampsia or eclampsia and a normal control subject. Depending on the metric that is used, the diagnostic indicator of eclampsia or pre-eclampsia may be significantly above or below a reference value (e.g., from a control subject not having pre-eclampsia or eclampsia).

sFlt-1 level is measured by measuring the amount of free, bound (i.e., bound to growth factor), or total sFlt-1 (bound+free). VEGF or PlGF levels are determined by measuring the amount of free PlGF or free VEGF (i.e., not bound to sFlt-1). One exemplary metric is [sFlt-1/(VEGF+PlGF)], also referred to as the pre-eclampsia anti-angiogenic index (PAAI).

By "pre-eclampsia anti-angiogenesis index (PAAI)" is meant the ratio of sFlt-1/VEGF+PlGF used as an indicator of anti-angiogenic activity. A PAAI greater than 10, more preferably greater than 20, is considered to be indicative of pre-eclampsia or risk of pre-eclampsia.

By "operably linked" is meant that a gene and a regulatory sequence(s) are connected in such a way as to permit gene expression when the appropriate molecules (e.g., transcriptional activator proteins) are bound to the regulatory sequence(s).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, (20$^{th}$ edition), ed. A. Gennaro, 2000, Lippincott, Williams & Wilkins, Philadelphia, Pa.

By "placental growth factor (PlGF)" is meant a mammalian growth factor that is homologous to the protein defined by GenBank accession number P49763 and that has PlGF biological activity. PlGF is a glycosylated homodimer belonging to the VEGF family and can be found in two distinct isoforms through alternative splicing mechanisms. PlGF is expressed by cyto- and syncytiotrophoblasts in the placenta and PlGF biological activities include induction of proliferation, migration, and activation of endothelial cells, particularly trophoblast cells.

By "polymorphism" is meant a genetic variation, mutation, deletion or addition in an sFlt-1, PlGF, or VEGF nucleic acid molecule that is indicative of a predisposition to develop the conditions. Such polymorphisms are known to the skilled artisan and are described by Parry et al. (*Eur. J Immunogenet.* 26:321-3, 1999). A polymorphism may be present in the promoter sequence, an open reading frame, intronic sequence, or untranslated 3' region of an sFlt-1 gene.

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. Pre-eclampsia generally occurs after the 20$^{th}$ week of gestation. Pre-eclampsia is generally defined as some combination of the following symptoms: (1) a systolic blood pressure (BP)>140 mmHg and a diastolic BP>90 mmHg after 20 weeks gestation (generally measured on two occasions, 4-168 hours apart), (2) new onset proteinuria (1+ by dipstik on urinanaysis, >300 mg of protein in a 24-hour urine collection, or a single random urine sample having a protein/creatinine ratio>0.3), and (3) resolution of hypertension and proteinuria by 12 weeks postpartum. Severe pre-eclampsia is generally defined as (1) a diastolic BP>110 mmHg (generally measured on two occasions, 4-168 hours apart) or (2) proteinuria characterized by a measurement of 3.5 g or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "protein" or "polypeptide" or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "reduce or inhibit" is meant the ability to cause an overall decrease preferably of 20% or greater, more preferably of 50% or greater, and most preferably of 75% or greater, in the level of protein or nucleic acid, detected by the aforementioned assays (see "expression"), as compared to samples not treated with antisense nucleobase oligomers or dsRNA used for RNA interference.

By "small interfering RNAs (siRNAs)" is meant an isolated dsRNA molecule, preferably greater than 10 nucleotides in length, more preferably greater than 15 nucleotides in length, and most preferably greater than 19 nucleotides in length that is used to identify the target gene or mRNA to be degraded. A range of 19-25 nucleotides is the most preferred size for siRNAs. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 21 to 23 nt RNA or internally (at one or more nucleotides of the RNA). In a preferred embodiment, the RNA molecules contain a 3'hydroxyl group. Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNA interference (RNAi). As used herein, RNAi refers to the ATP-dependent targeted cleavage and degradation of a specific mRNA molecule through the introduction of small interfering RNAs or dsRNAs into a cell or an organism. As used herein "mediate RNAi" refers to the ability to distinguish or identify which RNAs are to be degraded.

By "soluble Flt-1 (sFlt-1)" (also known as sVEGF-R1) is meant the soluble form of the Flt-1 receptor, that is homologous to the protein defined by GenBank accession number U01134, and that has sFlt-1 biological activity. The biological activity of an sFlt-1 polypeptide may be assayed using any standard method, for example, by assaying sFlt-1 binding to VEGF. sFlt-1 lacks the transmembrane domain and the cytoplasmic tyrosine kinase domain of the Flt-1 receptor. sFlt-1 can bind to VEGF and PlGF with high affinity, but it cannot induce proliferation or angiogenesis and is therefore functionally different from the Flt-1 and KDR receptors. sFlt-1 was initially purified from human umbilical endothelial cells and later shown to be produced by trophoblast cells in vivo. As used herein, sFlt-1 includes any sFlt-1 family member or isoform. In additional embodiments, sFlt-1 can also mean degradation products or fragments that result from enzymatic cleavage of the Flt-1 receptor and that maintain sFlt-1 biological activity. In one example, specific metalloproteinases released from the placenta may cleave the extracellular domain of Flt-1 receptor to release the N-terminal portion of Flt-1 into circulation.

By "specifically binds" is meant a compound or antibody which recognizes and binds a polypeptide of the invention but that does not substantially recognize and bind other molecules in a sample, for example, a biological sample, which naturally includes a polypeptide of the invention. In one example, an antibody that specifically binds sFlt-1 does not bind Flt-1.

By "subject" is meant a mammal, including, but not limited to, a human or non-human mammal, such as a bovine, equine, canine, ovine, or feline. Included in this definition are pregnant, post-partum, and non-pregnant mammals.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein. Preferably, the amino acid sequence is at least 70%, more preferably at least about 80%, and most preferably at least about 90% homologous to another amino acid sequence. Methods to determine identity are available in publicly available computer programs. Computer program methods to determine identity between two sequences include, but are not limited to, the GCG program package (Devereux et al., *Nucleic Acids Research* 12: 387, 1984), BLASTP, BLASTN, and FASTA (Altschul et al., *J. Mol. Biol.* 215:403 (1990). The well-known Smith Waterman algorithm may also be used to determine identity. The BLAST program is publicly available from NCBI and other sources (*BLAST Manual*, Altschul, et al., NCBI NLM NIH, Bethesda, Md. 20894; BLAST 2.0 at http://www.ncbi.nlm.nih.gov/blast/). These software programs match similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "symptoms of pre-eclampsia" is meant any of the following: (1) a systolic blood pressure (BP)>140 mmHg and a diastolic BP>90 mmHg after 20 weeks gestation, (2) new onset proteinuria (1+ by dipstik on urinanaysis, >300 mg of protein in a 24 hour urine collection, or random urine protein/creatinine ratio>0.3), and (3) resolution of hypertension and proteinuria by 12 weeks postpartum.

The symptoms of pre-eclampsia can also include renal dysfunction and glomerular endotheliosis or hypertrophy. By "symptoms of eclampsia" is meant the development of any of the following symptoms due to pregnancy or the influence of a recent pregnancy: seizures, coma, thrombocytopenia, liver edema, pulmonary edema, and cerebral edema.

By "therapeutic amount" is meant an amount that when administered to a patient suffering from pre-eclampsia or eclampsia is sufficient to cause a qualitative or quantitative reduction in the symptoms of pre-eclampsia or eclampsia as described herein. A "therapeutic amount" can also mean an amount that when administered to a patient suffering from pre-eclampsia or eclampsia is sufficient to cause a reduction in the expression levels of sFlt-1 or an increase in the expression levels of VEGF or PlGF as measured by the assays described herein.

By "treating" is meant administering a compound or a pharmaceutical composition for prophylactic and/or therapeutic purposes. To "treat disease" or use for "therapeutic treatment" refers to administering treatment to a subject already suffering from a disease to improve the subject's condition. Preferably, the subject is diagnosed as suffering from pre-eclampsia or eclampsia based on identification of any of the characteristic symptoms described below or the use of the diagnostic methods described herein. To "prevent disease" refers to prophylactic treatment of a subject who is not yet ill, but who is susceptible to, or otherwise at risk of, developing a particular disease. Preferably a subject is determined to be at risk of developing pre-eclampsia or eclampsia using the diagnostic methods described herein. Thus, in the claims and embodiments, treating is the administration to a mammal either for therapeutic or prophylactic purposes.

By "trophoblast" is meant the mesectodermal cell layer covering the blastocyst that erodes the uterine mucosa and through which the embryo receives nourishment from the mother; the cells contribute to the formation of the placenta.

By "vascular endothelial growth factor (VEGF)" is meant a mammalian growth factor that is homologous to the growth factor defined in U.S. Pat. Nos. 5,332,671; 5,240,848; 5,194,596; and Charnock-Jones et al. (*Biol. Reproduction*, 48: 1120-1128, 1993), and has VEGF biological activity. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g. VEGF-A, VEGF-B, VEGF-C, VEGF-D, VEGF-E, VEGF189, VEGF165, or VEGF 121). Preferably, VEGF is the VEGF121 or VEGF 165 isoform (Tischer et al., J. Biol. Chem. 266, 11947-11954, 1991; Neufed et al. *Cancer Metastasis* 15:153-158, 1996), which is described in U.S. Pat. Nos. 6,447,768; 5,219,739; and 5,194,596, hereby incorporated by reference. Also included are mutant forms of VEGF such as the KDR-selective VEGF and Flt-selective VEGF described in Gille et al. (*J Biol. Chem.* 276:3222-3230, 2001). As used herein VEGF also includes any modified forms of VEGF such as those described in LeCouter et al. (Science 299:890-893, 2003). Although human VEGF is preferred, the invention is not limited to human forms and can include other animal forms of VEGF (e.g. mouse, rat, dog, or chicken).

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

Other features and advantages of the invention will be apparent from the following description of the preferred embodiments thereof, and from the claims.

BRIEF DESCRIPTION OF THE DRAWINGS

FIG. 1A is an autoradiogram showing mRNA expression of placental sFlt-1 from three patients with pre-eclampsia (P1, P2, P3) and three normotensive term pregnancies (N1, N2, N3) as determined by northern blot analysis. The higher band (7.5 kb) is the full length flt-1 mRNA and the lower, more abundant band (3.4 kb) is the alternatively spliced sFlt-1 mRNA. GAPDH is included as a control and the arrowhead indicates 28S RNA. Patients P1 and P2 had severe pre-eclampsia, whereas patient P3 had mild pre-eclampsia. FIG. 1B is a graph showing sFlt-1 levels in serum from patients with mild pre-eclampsia (mild PE), patients with severe pre-eclampsia (severe PE), and normotensive pregnant women at term (normal). sFlt-1 levels were measured by an ELISA performed for sFlt-1 using a commercially available kit (R & D Systems, Minneapolis, Minn.). Patients with pre-term deliveries for other reasons (pre-term) were included as additional controls to rule out gestational age specific changes. The number of patients tested is shown in parenthesis in the X axis. Samples were collected prior to delivery (t=0) and 48 hours after delivery (t=48). FIG. 1C is a graph showing anti-angiogenesis index ratios (PAAI=sFlt-1/(VEGF+PlGF)) ratios at the time of delivery (t=0) as determined by ELISA for all the patients described in FIG. 1B.

FIGS. 2A, 2B, and 2C show assays performed using serum from a normal patient, while FIGS. 2D, 2E, and 2F show assays performed using serum from a patient with pre-eclampsia. In FIG. 2A, t=0 (10% serum from a normal pregnant woman at term); in FIG. 2B, t=48 (10% serum from normal pregnant woman 48 hours after delivery); in FIG. 2C, t=0+exogenous sFlt-1 (10 ng/ml); in FIG. 2D, t=0 (10% serum from pre-eclamptic woman prior to delivery); in FIG. 2E, t=48 (10% serum from pre-eclamptic woman 48 hours after delivery); and in FIG. 2F, t=0+exogenous VEGF(10 ng/ml)+PlGF (10 ng/ml). The tube assay was quantitated and the mean tube length+/−SEM is shown in pixels at the bottom of each panel.

FIG. 3A shows that the increase in relaxation responses of rat renal arterioles to sFlt-1 (S), VEGF (V), PlGF (P) was measured at three different doses. V+ and P+ represent vasodilatory responses of the individual reagents in the presence of sFlt-1 at 100 ng/ml. All experiments were done in 6 different dissected rat renal microvessels and data is shown as mean+/−SEM. The * represents statistical significance with $p<0.01$ as compared to individual reagents alone. FIG. 3B shows the increase in relaxation responses at physiological doses: VEGF 100 pg/ml (V), PlGF 500 pg/ml (P), sFlt-1 10 ng/ml (S), VEGF (100 pg/ml)+PlGF 500 pg/ml (V+P) or VEGF (100 pg/ml)+PlGF 500 pg/ml+sFlt-1 10 ng/ml (V+P+S). All experiments were done in 6 different dissected rat renal microvessels and data is shown as mean+/−SEM. The * represents statistical significance with $p<0.05$ as compared with V+P.

FIG. 4A is photomicrograph showing hematoxylin and eosin (H & E) staining in a capillary occlusion in the sFlt-1 treated animals with enlarged glomeruli and swollen cytoplasm as compared to controls. "Glomerular endotheliosis" with bubbly cytoplasm is shown in the sFlt-1 treated animals on periodic acid schiff (PAS) stain. All light microscopy pictures were taken at 60×, original magnification. FIG. 4B is an electron micrograph of sFlt-1 treated glomeruli that confirms cytoplasmic swelling of the endocapillary cells. The immunofluorescence (IF) for fibrin pictures were taken at 40× and the EM pictures were taken at 2400×, original magnification. All figures were reproduced at identical magnifications.

FIG. 5A is a graph showing the mean serum concentrations in pg/ml for normotensive controls (lighter line with open triangles), cases before pre-eclampsia (filled circles), and cases after pre-eclampsia—"endpoint" specimens—(filled squares) within 4-5 week gestational age windows prior to onset of labor. Brackets indicate standard error of the mean. Asterisks indicate significant differences with respect to control specimens within the same gestational age window after logarithmic transformation: *$p<0.05$, $p<0.01$, *$p<0.001$. FIG. 5B is a graph showing the mean serum concentrations of sFlt1 in pg/ml for cases before and after the onset of pre-eclampsia within intervals of weeks before pre-eclampsia. PE indicates the arithmetic mean of 43 endpoint specimens (obtained on or following onset of pre-eclampsia). Mean gestational age (days) is indicated in parentheses below each time interval. The horizontal line indicates the level in the endpoint specimens. The vertical lines demarcate the period ≤5 weeks before pre-eclampsia. FIG. 5C is a graph showing the mean serum concentrations of sFlt-1 in pg/ml by gestational age windows for normotensive controls and cases before pre-eclampsia, after excluding specimens obtained within 5 weeks of onset of pre-eclampsia. There are no significant differences.

FIG. 6A is a graph showing PlGF levels in all specimens obtained before labor and delivery. Brackets indicate standard error of the mean. Asterisks indicate significant differences with respect to control specimens within the same interval after logarithmic transformation: $p<0.01$, *$p<0.001$. FIG. 6B is a graph showing the mean serum concentrations of PlGF in pg/ml for cases before and after onset of pre-eclampsia within intervals of weeks before pre-eclampsia. PE indicates the arithmetic mean of 43 endpoint specimens (obtained on or following onset of pre-eclampsia). Mean gestational age (days) is indicated in parentheses below each time interval. The horizontal line indicates the level in the endpoint specimens. The vertical lines demarcate the period ≤5 weeks before pre-eclampsia. FIG. 6C is a graph showing the mean serum concentrations of PlGF in pg/ml by gestational age windows for normotensive controls and cases onset of pre-eclampsia.

FIG. 7A is a graph showing the arithmetic mean serum concentrations of sFlt-1 (black bars) and PlGF (white bars) at 23-32 weeks of gestation in controls and cases (before onset of clinical disease) with mild pre-eclampsia, severe pre-eclampsia, pre-eclampsia with onset <37 weeks, pre-eclampsia with a small for gestational age (SGA) infant, and pre-eclampsia with onset <34 weeks. Numbers of specimens are recorded below each column pair. Adjustment for gestational age and body mass index resulted in minor changes with no affect on level of significance. FIG. 7B is a graph showing the arithmetic mean serum concentrations of sFlt-1 (black bars) and PlGF (white bars) at 33-41 weeks of gestation in controls and cases (before onset of clinical disease) with mild pre-eclampsia, severe pre-eclampsia, pre-eclampsia with onset <37 weeks, and pre-eclampsia with an SGA infant. Numbers of specimens are recorded below each column pair. Adjustment for gestational age and body mass index resulted in minor changes.

DETAILED DESCRIPTION

We have discovered that sFlt-1 levels are elevated in blood serum samples taken from pre-eclamptic women. sFlt-1 binds to VEGF and PlGF with high affinity and blocks the mitogenic and angiogenic activity of these growth factors. Thus, sFlt-1 is an excellent diagnostic marker for pre-eclampsia and VEGF and PlGF may be used to treat pre-eclampsia. Furthermore, we have discovered therapeutic agents that interfere with sFlt-1 binding to purified VEGF or PlGF, or agents that increase levels of biologically active VEGF or PlGF, can be used to treat or prevent pre-eclampsia or eclampsia in a subject. Such agents include, but are not limited to, antibodies to sFlt-1, oligonucleotides for antisense or RNAi that reduce levels of sFlt-1, compounds that increase the levels of VEGF or PlGF, and small molecules that bind sFlt-1 and block the growth factor binding site. The invention also features methods for measuring levels of growth factors; the methods can be used as diagnostic tools for early detection of pre-eclampsia or an increased risk of developing pre-eclampsia or eclampsia.

While the detailed description presented herein refers specifically to sFlt-1, VEGF, or PlGF, it will be clear to one skilled in the art that the detailed description can also apply to sFlt-1, VEGF, or PlGF family members, isoforms, and/or variants, and to growth factors shown to bind sFlt-1. The following examples are for the purposes of illustrating the invention, and should not be construed as limiting.

Example 1. Increased Levels of sFlt-1 mRNA and Protein in Pregnant Women with Pre-Eclampsia In an attempt to identify novel secreted factors playing a pathologic role in pre-eclampsia, we performed gene expression profiling of placental tissue from women with and without pre-eclampsia using Affymetrix U95A microarray chips. We found that the gene for sFlt-1 was upregulated in women with pre-eclampsia.

Figure 1A:
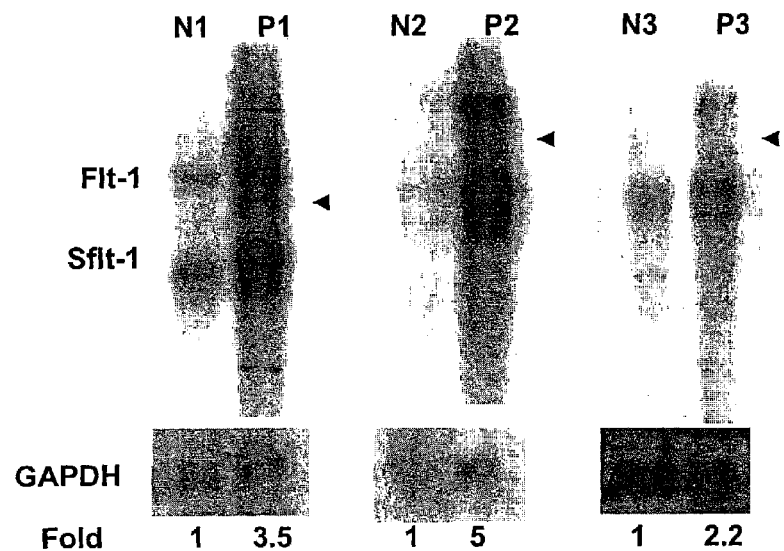
FIGS. 1A-1C show sFlt-1 mRNA and protein expression levels in pre-eclampsia.
Figure 1B:
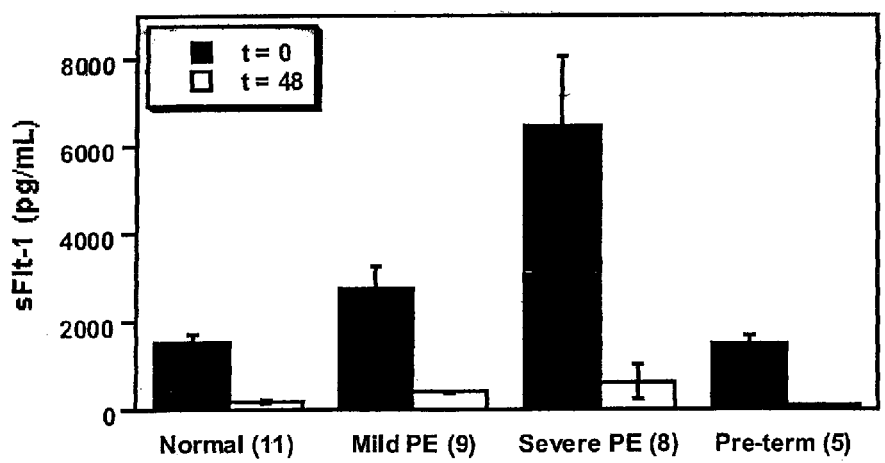

In order to confirm the upregulation of sFlt-1 in pre-eclampsia, we performed Northern blots to analyze the placental sFlt-1 mRNA levels (FIG. 1A) and ELISA assays to measure serum protein levels of sFlt-1 (FIG. 1B) in pre-eclamptic pregnant women as compared with normotensive pregnant women. Pre-eclampsia was defined as (1) a systolic blood pressure (BP)>140 mmHg and a diastolic BP>90 mmHg after 20 weeks gestation, (2) new onset proteinuria (1+ by dipstik on urinalysis, >300 mg of protein in a 24 hour urine collection, or random urine protein/creatinine ratio>0.3, and (3) resolution of hypertension and proteinuria by 12 weeks postpartum. Patients with underlying hypertension, proteinuria, or renal disease were excluded. Patients were divided into mild and severe pre-eclampsia based on the presence or absence of nephritic range proteinuria (>3 g of protein on a 24 hour urine collection or urine protein/creatinine ratio greater than 3.0). The mean urine protein/creatinine ratios in the mild pre-eclampsia group were 0.94+/−0.2 and in the severe pre-eclampsia group were 7.8+/−2.1. The mean gestational ages of the various groups were as follows: normal 38.8+/−0.2 weeks, mild pre-eclampsia 34+/−1.2 weeks, severe pre-eclampsia 31.3+/−0.6 weeks, and pre-term 29.5+/−2.0 weeks. Placental samples were obtained immediately after delivery. Four random samples were taken from each placenta, placed in RNAlater stabilization solution (Ambion, Austin, Tex.) and stored at −70° C. RNA isolation was performed using Qiagen RNAeasy Maxi Kit (Qiagen, Valencia, Calif.).

We detected an increase in both placental sFlt-1 mRNA and maternal serum sFlt-1 protein in pre-eclamptic pregnant women as compared to normotensive pregnant women. The average serum level of sFlt-1 was almost four times higher in the severe pre-eclampsia patients as compared to normal control pregnant women. To exclude the possibility that this effect was due to the earlier gestational age of the pre-eclamptic cases, we also measured sFlt-1 levels in gestationally matched normotensive women delivering pre-maturely for other reasons (gestational ages 23-36 weeks), and we found no significant difference in this group compared with normotensive term pregnancies. The probes used for northern blots were obtained by PCR and included a 500 bp fragment in the coding region from pUC 118 human flt-1 cDNA, and a GAPDH cDNA that was used as normalization control.

Figure 1C:
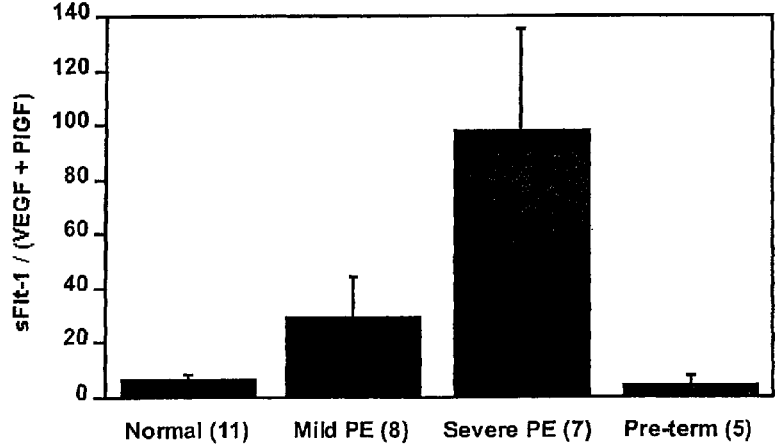
Figure 2A:
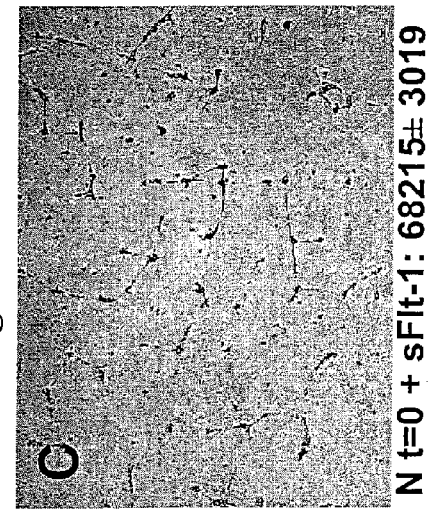
FIGS. 2A-2F are photomicrographs showing the anti-angiogenic effect of excess sFlt-1 in pre-eclampsia. Endothelial tube assays were performed using serum from four normal pregnant controls and four patients with pre-eclampsia. A representative experiment from one normal control and one patient with pre-eclampsia is shown.
Figure 2B:
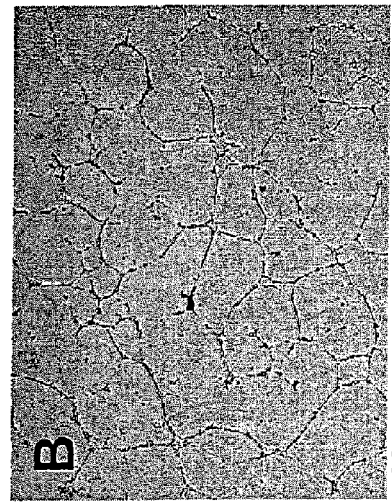
Figure 2C:
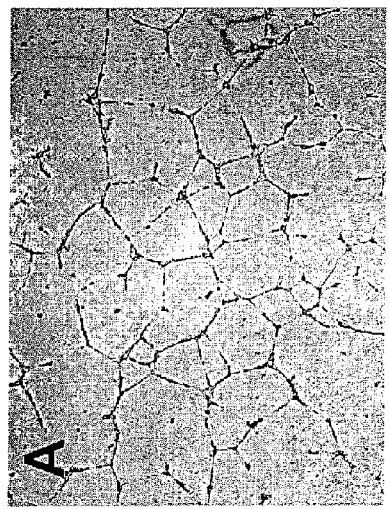
Figure 2D:
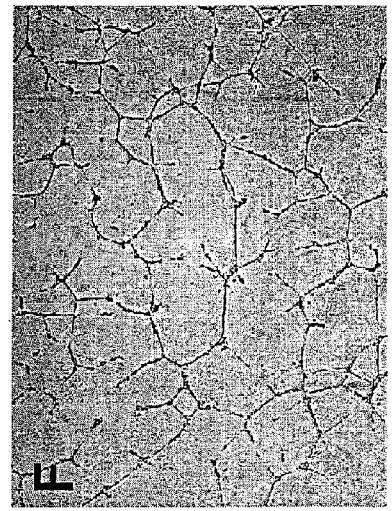
Figure 2E:
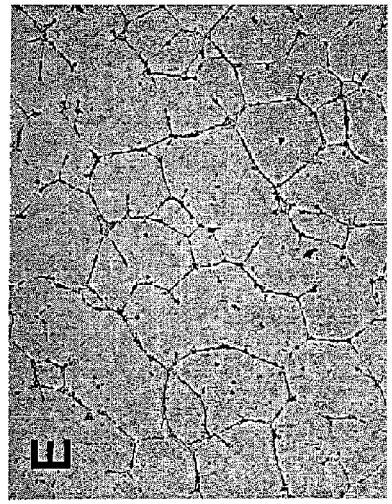
Figure 2F:
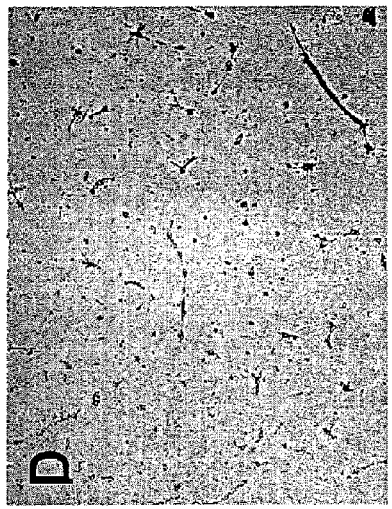

In normal pregnancy there is a balance between pro- and anti-angiogenic factors secreted by the placenta that is necessary for adequate placental development. We hypothesized that in pre-eclampsia, increased production of sFlt-1 and decreased production of VEGF and PlGF shifts the balance in favor of anti-angiogenesis. To address the net anti-angiogenic activity we measured VEGF and PlGF serum levels and found that PlGF and VEGF serum levels were lower in patients with pre-eclampsia as compared to normal control patients (mean PlGF, 235.3+/−45.3 pg/ml versus 464+/−116.6 pg/ml) as has been described (Tidwell et al., *Am. J. Obstet. Gynecol.*, 184:1267-1272, 2001). When we incorporated sFlt-1, VEGF and PlGF levels into an anti-angiogenic index, or PAAI, as an indicator of net anti-angiogenic activity, we found that we could clearly separate the pre-eclamptic from the normal patients and that the PAAI seemed to correlate with severity of the pre-eclampsia (FIG. 1C). This PAAI can be used as a diagnostic tool for the detection of pre-eclampsia in pregnant women.

Example 2. Serum from Women with Pre-Eclampsia Inhibits Angiogenesis in an In Vitro Endothelial Tube Assay We hypothesized that excess circulating sFlt-1 in patients with pre-eclampsia causes endothelial dysfunction and leads to an anti-angiogenic state. To address this, we used an endothelial tube assay as an in vitro model of angiogenesis. Growth factor reduced Matrigel (7 mg/mL, Collaborative Biomedical Products, Bedford, Mass.) was placed in wells (100 µl/well) of a pre-chilled 48-well cell culture plate and incubated at 37° C. for 25-30 minutes to allow polymerization. Human umbilical vein endothelial cells (30,000+ in 300 µl of endothelial basal medium with no serum, Clonetics, Walkersville, Md.) at passages 3-5 were treated with 10% patient serum, plated onto the Matrigel coated wells, and incubated at 37° C. for 12-16 hours. Tube formation was then assessed through an inverted phase contrast microscope at 4× (Nikon Corporation, Tokyo, Japan) and quantitatively analyzed (tube area and total length) using the Simple PCI imaging analysis software.

The conditions of the tube formation assay were adjusted such that normal human umbilical vein endothelial cells form tubes only in the presence of exogenous growth factors such as VEGF. Under these conditions, we found that while serum from normotensive women induced endothelial cells to form regular tube-like structures, serum from women with pre-eclampsia inhibited tube formation (FIG. 2). Notably, by 48 hours post-partum this anti-angiogenic effect had disappeared suggesting that the inhibition of tubes noted with the serum from pre-eclampsia patients was probably due to a circulating factor released by the placenta. When sFlt-1 was added to normotensive serum at doses similar to those found in patients with pre-eclampsia, tube formation did not occur, mimicking the effects seen with the serum from pre-eclamptic women. When exogenous VEGF and PlGF were added to the assay using pre-eclamptic serum, tube formation was restored (FIG. 2). Recombinant human VEGF, human PlGF, and human Flt-1Fc were used for these assays. These results suggested that the anti-angiogenic properties of pre-eclamptic serum were due to the antagonism of VEGF and PlGF by endogenous sFlt-1. These results also suggested that addition of purified VEGF and/or PlGF can reverse or mitigate the pre-eclamptic condition and can be used therapeutically.

Example 3. sFlt-1 Inhibits VEGF and PlGF Induced Vasodilation of Renal Microvessels The causative role of sFlt-1 in vasoconstriction was determined using an in vitro microvascular reactivity experiment. Microvascular reactivity experiments were done as described previously using rat renal microvessels (Sato et al., *J. Surg. Res.*, 90:138-143, 2000). Kidney artery microvessels (70-170 µm internal diameter) were dissected from rat kidneys using a 10× to 60× dissecting microscope (Olympus Optical, Tokyo, Japan). Microvessels were placed in an isolated microvessel chamber, cannulated with dual glass micropipettes measuring 30-60 µm in diameter, and secured with a 10-0 nylon monofilament suture (Ethicon, Somerville, N.J.). Oxygenated (95% oxygen and 5% carbon dioxide) Krebs' buffer solution warmed to 37° C. was continuously circulated through the vessel chamber and a reservoir containing a total of 100 ml of the solution. The vessels were pressurized to 40 mmHg in a no-flow state using a burette manometer filled with a Krebs' buffer solution. With an inverted microscope (40× to 200×; Olympus CK2 Olympus Optical) connected to video camera, the vessel image was projected onto a black-and-white television monitor. An electronic dimension analyzer (Living System Instrumentation, Burlington, Vt.) was used to measure the internal lumen diameter. Measurements were recorded with a strip-chart recorder (Graphtec, Irvine, Calif.). Vessels were allowed to bathe in the microvessel chamber for at least 30 minutes prior to any intervention. In all experimental groups, the relaxation responses of kidney microvessels were examined after pre-contraction of the microvessels with U46619 (thromboxane agonist) to 40-60% of their baseline diameter at a distending pressure of 40 mmHg. Once the steady-state tone was reached, the responses to various reagents such as VEGF, PlGF, and sFlt-1 were examined. Recombinant rat VEGF, mouse PlGF, and mouse Flt-1Fc were used for these assays. All drugs were applied extraluminally. Measurements were made when the response had stabilized (usually 2-3 minutes after the drug was administered). One to four interventions were performed on each vessel. The vessels were washed with a Krebs' buffer solution and allowed to equilibrate in a drug-free Krebs' buffer solution for 20-30 minutes between interventions.

Figure 3A:
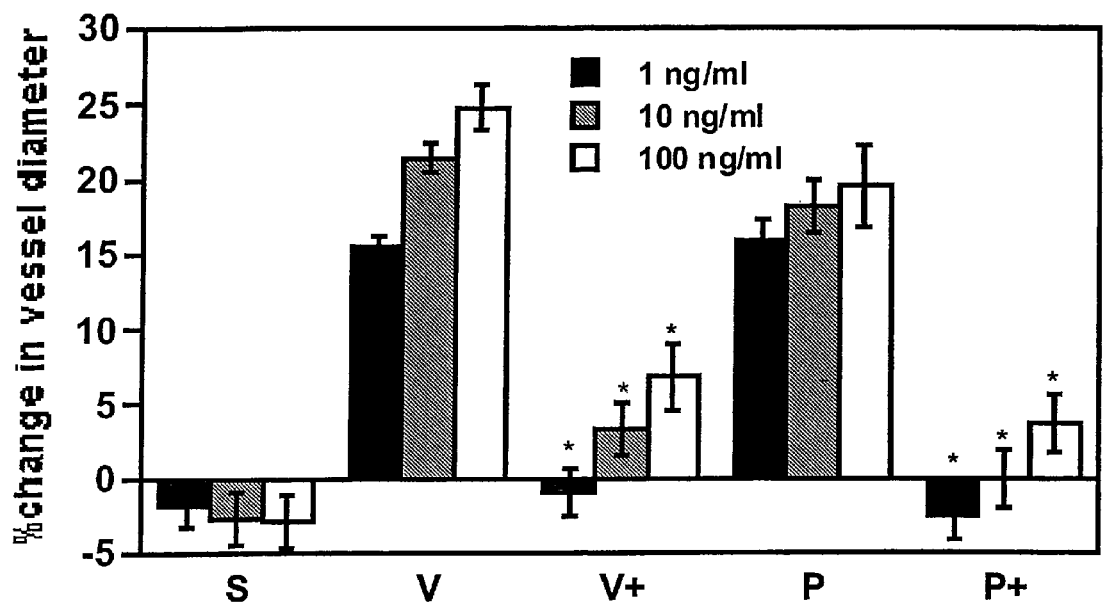
FIGS. 3A and 3B are graphs showing that inhibition of VEGF and PlGF induced vasodilation of renal microvessels by sFlt-1.
Figure 3B:
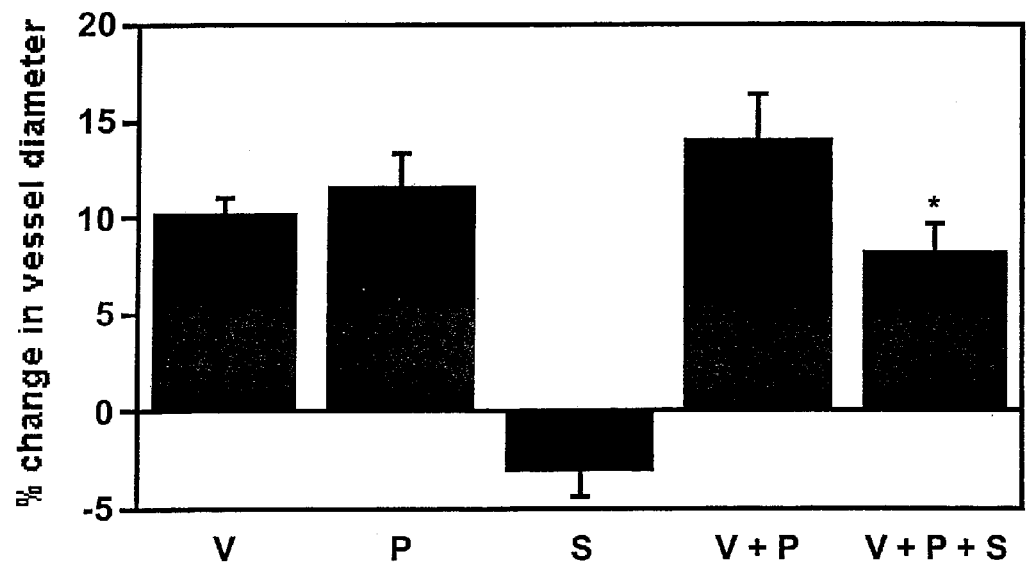

We found that sFlt-1 alone did not cause significant vasoconstriction, however it blocked the dose responsive increase in vasodilation induced by VEGF or PlGF (FIG. 3A). Furthermore, we found that VEGF and PlGF, at physiological levels seen in pregnancy, induced significant dose dependent arteriolar relaxation, and that this effect was blocked by the addition of 10 ng/ml sFlt-1, a concentration observed in severely pre-eclamptic women (FIG. 3B). This result suggested that circulating sFlt-1 in patients with pre-eclampsia may oppose vasorelaxation, thus contributing to hypertension. These results support the conclusion that sFlt-1 is responsible for many of the clinical and pathological symptoms of pre-eclampsia, including hypertension. Inhibition of sFlt-1, through the use of directed antibodies, for example, could reverse the effects of the protein in pre-eclamptic women and such sFlt-1 inhibitors could potentially be used as a therapeutic agent.

Example 4. Effects of sFlt-1 in an Animal Model of Pre-Eclampsia

Based on the above results, we hypothesized that the addition of exogenous sFlt-1 would produce hypertension and proteinuria in an animal model. Adenovirus expressing sFlt-1 has been shown to produce sustained systemic sFlt-1 levels associated with significant anti-tumor activity (Kuo et al., *Proc. Natl. Acad. Sci. USA*, 98:4605-4610, 2001). This recombinant adenovirus encoding murine sFlt-1 was injected into the tail vein of pregnant Sprague-Dawley rats on day 8-9 of pregnancy. Adenovirus encoding murine Fc and sFlk1-Fc (fusion protein of mouse VEGF receptor 1 Flk1 ectodomain and Fc protein) in equivalent doses were used as controls. Flk1 has been shown to bind to VEGF, but not PlGF. Hence, sFlk-1Fc was chosen as a control to help discriminate between the anti-VEGF and the anti-PlGF activity of sFlt1.

Both pregnant and non-pregnant Sprague-Dawley rats were injected with $1\times10^9$ pfu of Ad Fc, Ad sFlt-1, or Ad sFlk-1Fc by tail vein injections. These adenoviruses have been described previously (Kuo et al., supra) and were generated at the Harvard Vector Core Laboratory. Pregnant rats were injected with the adenoviruses at day 8-9 of pregnancy (early second trimester) and blood pressure was measured at day 16-17 of pregnancy (early third trimester). In non-pregnant animals, BPs were measured at day 8 after injection of the adenoviruses. BPs were measured in the rats after anesthesia with pentobarbital sodium (60 mg/kg, i.p.). The carotid artery was isolated and cannulated with a 3-Fr high-fidelity microtip catheter connected to a pressure transducer (Millar Instruments, Houston, Tex.). The Millar Mikro-Tip catheter was advanced into the artery to record blood pressure. Blood pressure and heart rate were recorded in by chart-strip recorder (model 56-1X 40-006158, Gould Instrument Systems, Cleveland, Ohio) and averaged over a 10-minute period. Blood, tissue, and urine samples were then obtained before euthanasia. Urinary albumin was measured by standard dipstick and quantitated by competitive enzyme-linked immunoassay (ELISA) as has been described elsewhere (Cohen et al., *Kidney Intl.*, 45: 1673-1679, 1994). Urinary creatinine was measured by a picric acid colorimetric procedure kit (Sigma, St. Louis, Mo.). We measured intrarterial blood pressures in the early third trimester of the pregnancy to mimic the natural pathology of pre-eclampsia. These experiments were also performed in non-pregnant female Sprague-Dawley rats to determine if the effects of sFlt-1 is direct or indirect through its effects on the placenta. Systemic levels of sFlt-1 on the day of blood pressure measurement were confirmed by Western blot analysis to be in the range of 25-350 ng/mL in the various sFlt-1 treated animals on the day of BP measurements. Blood pressure and proteinuria in the different experimental groups is shown in Table 1.

TABLE 1

Blood Pressure and Proteinuria in Rats

| | N | MAP (mmHg) | U alb:cr ratio |
|---|---|---|---|
| Fc (P) | 5 | 75.6 ± 11.1 | 62 ± 21 |
| sFlt-1 (P) | 4 | 109.0 ± 19.3* | 6923 ± 658* |
| sFlk-1Fc (P) | 4 | 72.8 ± 14.7 | 50 ± 32 |
| Fc (NP) | 5 | 89.3 ± 5.7 | 138 ± 78 |
| sFlt-1 (NP) | 6 | 117.9 ± 12.9* | 12947 ± 2776* |
| sFlk-1Fc (NP) | 4 | 137.3 ± 2.3* | 2269 ± 669* |

Pregnant (P) and nonpregnant (NP) rats were administered adenovirus expressing Fc (control), sFlt-1, or sFlk-1Fc protein.
Mean arterial blood pressure (MAP = diastolic + ⅓ pulse pressure in mmHg) ± S.E.M and urine albumin:Cr ratio (mg of albumin per gram of creatinine) ± S.E.M were measured eight days later, corresponding to the early third trimester in the pregnant rats.
N = the number of animals in each experimental group.
The * represents statistical significance with $p < 0.01$ when compared with the control group (Fc).

Figure 4A:
FIGS. 4A and 4B are images showing sFlt-1 induction of glomerular endotheliosis.
Figure 4B:
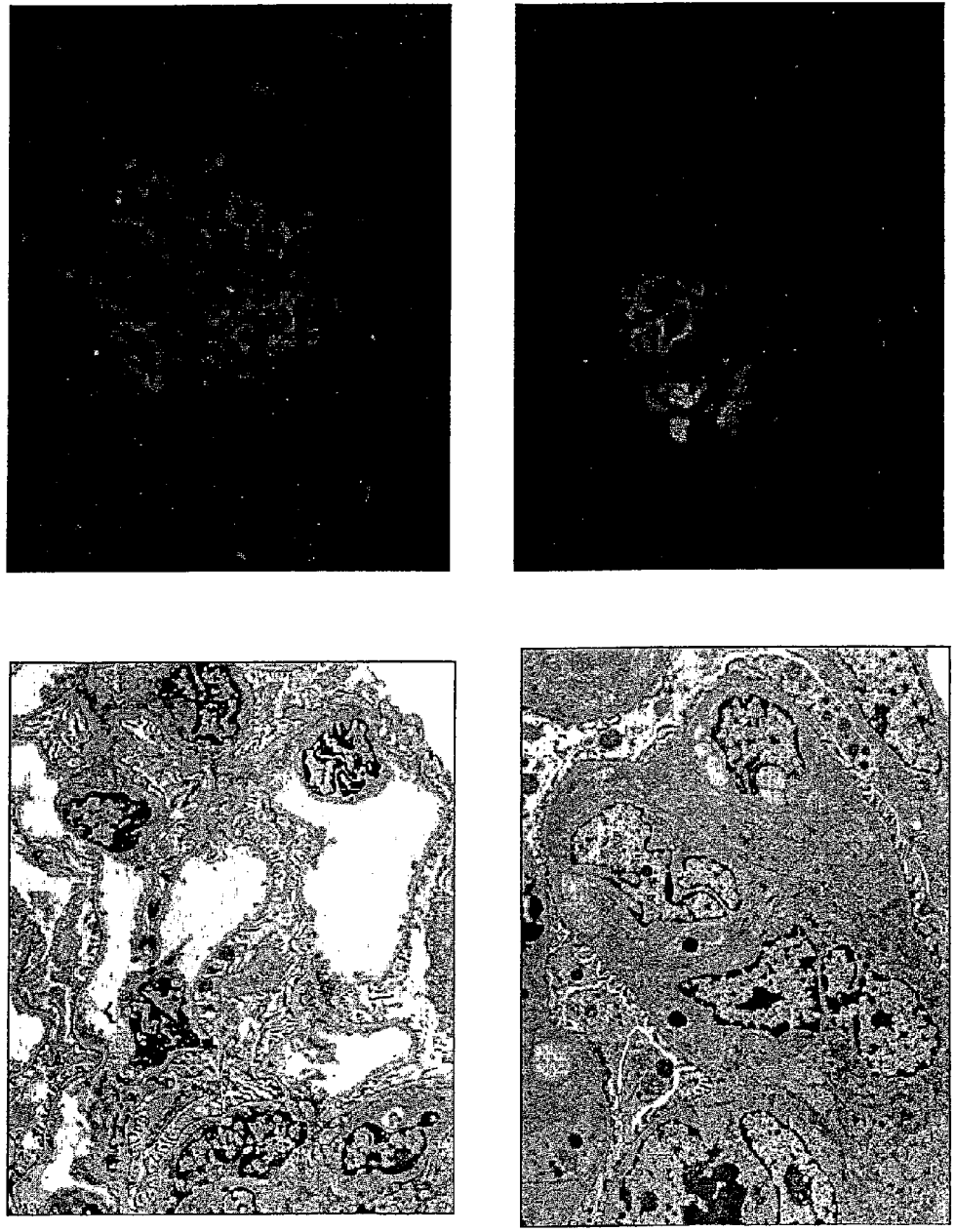

Pregnant rats treated with sFlt-1 had significant hypertension and nephrotic range albuminuria compared with Fc controls. Nonpregnant rats administered sFlt1 also developed hypertension and proteinuria. Notably, the sFlk-Fc treated nonpregnant rats developed hypertension and proteinuria, whereas the sFlk-Fc treated pregnant rats did not. In pregnancy, therefore, the antagonism of VEGF alone is insufficient to produce pre-eclampsia, possibly due to the presence of high levels of PlGF. In the nonpregnant state, where PlGF is virtually absent, antagonism of VEGF alone is sufficient to disrupt the pro/anti-angiogenic balance and produce renal pathologies similar to those associated with pre-eclampsia. Various staining techniques were used to examine the renal lesion that was observed in all sFlt-1 treated rats (FIG. 4). Harvested kidneys from the rats were fixed in Bouin's solution, sectioned and stained with H&E and PAS stains. For electron microscopy, renal tissue was fixed in glutaraldehyde, embedded in araldite-epon mixture, and ultrathin kidney sections (1 μm) were cut, stained with Toluene blue and assessed using a Zeiss EM 10 at various magnifications. Immunofluorescence for fibrin deposits within the glomeruli was done using polyclonal anti-fibrin antibody (ICN, Switzerland). Global and diffuse glomerular endotheliosis was the renal lesion universally observed in the sFlt-1 treated rats. We detected glomerular enlargement with occlusion of the capillary loops by swelling and hypertrophy of endocapillary cells. Numerous apparent protein resorption droplets were seen in the glomerular epithelial cells. No segmental glomerulosclerosis was observed. Isolated "double contours" and focal deposition of fibrin within the glomeruli were seen. This finding of fibrin deposition in the absence of significant mesangial interposition is similar to what has been described as typical of the pre-partum stage of the human disease (Kincaid-Smith, *Am. J. Kidney Dis.,* 17:144-148, 1991). Immunofluorescence for fibrin showed foci of fibrin deposition within the glomeruli of sFlt-1 treated animals but not Fc treated animals. The sFlk1 treated nonpregnant rats developed the same lesion. In fact, when sFlk1 was used at the same levels as sFlt-1, the renal damage was more severe in the non-pregnant rats, as there are fewer circulating pro-angiogenic molecules for the sFlt-1 to antagonize. These results suggested that elevated levels of sFlt-1 may be responsible for the glomerular endotheliosis associated with pre-eclampsia, but that this effect was independent of the placenta since glomerular changes were detected in nonpregnant as well as pregnant rats. These results also suggested that antagonism of both VEGF and PlGF is important in the pathology of pre-eclampsia as hypertension and proteinuria occurred in sFlk-1 treated non-pregnant mice but not in sFlk-1 treated pregnant mice where PlGF levels are high.

The animal model created herein can be used as an experimental model to test novel therapeutic compounds. Both the efficacy of potential therapeutic compounds and the pharmacology and toxicity can be studied using this animal model.

Example 5. Effects of sFlt-1 in an Animal Model of Eclampsia

Pregnant rats in their early second trimester of pregnancy are injected with exogenous sFlt-1. The rats are then monitored and tested during their early third trimester for the development of eclampsia. Tests used for detection of eclampsia can include MRI of the rat brains for the development of edema, EEG of the rat brain for the development of seizures, and histology of the rat brains to determine if endothelial damage has occurred along the blood-brain barrier and choroids-plexus using specific endothelial markers.

The animal model created herein can be used as an experimental model to test novel therapeutic compounds. Both the efficacy of potential therapeutic compounds and the pharmacology and toxicity can be studied using this animal model.

Example 6. PlGF/Creatinine Ratio in Urine is Diagnostic of Pre-Eclampsia

Urine samples were obtained from 10 women at 16 weeks gestation (five normals, four mild preeclamptics, and one severe pre-eclamptic). These samples were provided by Dr. Ravi Thadhani at Massachusetts General Hospital. The average urinary free PlGF/creatinine ratios (pg PlGF per mg of creatinine) for the normal pregnant women were 78+/−10.7 and for the four mild pre-eclamptics were 33+/−5.0 and for the one severe preeclamptic patient was 17. Thus, an alteration in the ratio of PlGF to creatinine in urine is useful as a diagnostic indicator for pre-eclampsia in a patient.

Example 7. Urinary PlGF Levels Measure in Control and Pre-Eclamptic Pregnant Women Urinary PlGF was measured in control pregnant women and pre-eclamptic women using archived urine specimens from the CPEP trial (see Example 8) in collaboration with Dr. Richard Levine at the NIH (Table 2). The table below shows significant decreases in urinary PlGF in patients who later developed pre-eclampsia during mid-pregnancy (22-30 weeks) and late pregnancy (>30 weeks), but not in early pregnancy (<20 weeks). All urine specimens were obtained prior to clinical symptoms of pre-eclampsia.

TABLE 2

Urinary PlGF levels in pg/ml in pre-eclamptic versus control pregnant patients.

|  | Control (n = 120) | PE (n = 120) |
|---|---|---|
| Early pregnancy | 39.80 | 42.28 |
| Mid pregnancy | 193.11 | 98.66 (p < 0.0001) |
| Late pregnancy | 107.82 | 62.05 (p = 0.0213) |

Example 8. sFlt-1 and PlGF Protein Levels as a Diagnostic Indicator of Pre-Eclampsia and Eclampsia in Women For this study we used archived samples from the Calcium for Pre-eclampsia Prevention trial in order to analyze the gestational patterns of circulating sFlt-1, free PlGF, and free VEGF in normotensive and pre-eclamptic pregnancies in collaboration with Dr. Richard Levine at the NIH. Calcium for Pre-eclampsia Prevention, or CPEP, was a randomized, double-blind clinical trial conducted during 1992-1995 to evaluate the effects of daily supplementation with 2 grams elemental calcium or placebo on the incidence and severity of pre-eclampsia (Levine et al., *N Engl. J. Med.* 377:69-76, 1997; Levine et al., *Control Clin. Trials* 17:442-469, 1996). Healthy nulliparous women with singleton pregnancies were enrolled between 13 and 21 weeks gestation at five participating U.S. medical centers and followed until 24 hours postpartum using a common protocol and identical data collection forms. At enrollment, all CPEP participants had blood pressure<135/85 mm Hg, and none had renal dysfunction or proteinuria. Gestational age was determined by ultrasound examination. Serum specimens were obtained from participants prior to enrollment in the trial (13-21 weeks), at 26-29 weeks, at 36 weeks if still pregnant, and when hypertension or proteinuria were noted. "Endpoint specimens" were specimens obtained at or after onset of pre-eclampsia symptoms and signs, but before labor and delivery as described elsewhere (Levine et al., 1996, supra). Archived blood samples from the CPEP trial were obtained through collaboration with Dr. Richard Levine at the NIH.

Participants

We selected subjects having complete outcome information, serum samples obtained at <22 weeks, and a liveborn male infant. Of 4,589 CPEP participants, we excluded 253 lost to follow-up, 21 whose pregnancy had terminated prior to 20 weeks, 13 missing maternal or perinatal outcome data, 4 without smoking history, 9 with hypertension not verified by chart review teams, and 32 others with stillbirths, leaving 4,257 women with adequate information and live births. Among these 2,156 had male infants. After excluding one woman whose infant had a chromosomal abnormality, 381 with gestational hypertension, and 43 without a baseline serum specimen, 1,731 women remained. Of these, 175 developed pre-eclampsia and 1,556 remained normotensive throughout pregnancy.

Since calcium supplementation had no effect on the risk and severity of pre-eclampsia and was unrelated to concentrations of pro- and anti-angiogenic molecules, cases and controls were chosen without regard to CPEP treatment. For each pre-eclampsia case one normotensive control was selected, matched for enrollment site, gestational age at collection of the first serum specimen (within one week), and freezer storage time at −70° C. (within 12 months). 120 matched pairs ("cases" and "controls") were randomly chosen for analysis of all 657 serum specimens obtained before labor (Table 3, below). Mean gestational age at collection of the first serum specimen was 112.8 and 113.6 days in cases and controls, respectively; mean duration of freezer storage was 9.35 and 9.39 years.

TABLE 3

Characteristics of cases and controls at CPEP enrollment and of their newborn infants

| Characteristic | Cases (n = 120) | Controls (n = 120) |
|---|---|---|
| Age (yr) | 20.8 ± 4.5 | 20.2 ± 3.6 |
| Height (cm) | 161.0 ± 6.7 | 163.0 ± 6.9 * |
| Weight (kg) | 71.0 ± 19.4 | 66.8 ± 17.1 |
| Body mass index | 27.3 ± 6.8 | 25.1 ± 6.1 ** |
| Systolic blood pressure (mm Hg) | 109.5 ± 8.8 | 105.7 ± 9.0 ** |
| Diastolic blood pressure (mm Hg) | 62.0 ± 7.9 | 59.4 ± 7.4 ** |
| Prior pregnancy loss [n (%)] | 23 (19.2) | 25 (20.8) |
| Current smoker [n (%)] | 9 (7.5) | 13 (10.8) |
| Private health insurance [n (%)] | 8 (6.7) | 13 (10.8) |
| Ever married [n (%)] | 25 (20.8) | 24 (20.0) |
| Race/ethnicity | | |
| White, non-Hispanic [n (%)] | 24 (20.0) | 35 (29.2) |
| White, Hispanic [n (%)] | 21 (17.5) | 14 (11.7) |
| African-American [n (%)] | 69 (57.5) | 68 (56.7) |
| Other, unknown [n (%)] | 6 (5.0) | 3 (2.5) |
| Birthweight (g) | 3100 ± 796 | 3255 ± 595 |
| Delivery <37 wks [n (%)] | 29 (24.2) | 9 (7.5) ** |
| Small for gestational age | | |
| ($<10^{th}$ percentile) [n (%)] | 18 (15.0) | 4 (3.3) ** |

Mean ± standard deviation unless indicated
* $p < 0.05$
** $p < 0.01$

For this study, hypertension was defined as a diastolic blood pressure of at least 90 mm Hg on two occasions 4-168 hours apart. Severe hypertension was defined as a diastolic blood pressure of at least 110 mm Hg on two occasions 4-168 hours apart, or one occasion if the woman had received anti-hypertensive therapy. Proteinuria was defined as 300 mg or more protein in a 24-hour urine collection, two random urine specimens 4-168 hours apart containing at least 1+ protein by dipstick, a single urine sample with a protein/creatinine ratio at least 0.35, or a single random urine specimen containing at least 2+ protein by dipstick. Severe proteinuria was diagnosed by a 24-hour urine collection sample containing at least 3.5 g protein or by two random urine specimens with at least 3+ protein by dipstick. Pre-eclampsia was defined as hypertension and proteinuria occurring within 7 days of each other; severe pre-eclampsia was defined as pre-eclampsia with severe hypertension, severe proteinuria, HELLP syndrome (hemolysis, elevated liver enzymes, low platelets), or eclampsia. The onset of pre-eclampsia was the time of detection of the first elevated blood pressure or proteinuria in the urine sample leading to the diagnosis of pre-eclampsia.

Small for gestational age (SGA) was defined as birth weight lower than the $10^{th}$ percentile for gestational age according to US tables of birth weight for gestational age by race, parity, and infant sex (Zhang and Bowes 1995, supra).

Procedures

Assays were performed at the Beth Israel Deaconess Medical Center by laboratory personnel who were blinded to patients' diagnoses and other relevant clinical information. Specimens were randomly ordered for analysis. Enzyme-linked immunosorbent assays (ELISA) for human sFlt-1, free PlGF, and free VEGF were performed according to the manufacturer's instructions, using kits purchased from R&D Systems (Minneapolis, Minn.). Aliquots of serum samples which had been stored at −70° C., were thawed to room temperature, diluted with BSA/Tris-buffered saline, and incubated for 2 hours in a 96-well plate pre-coated with a capture antibody directed against sFlt-1, PlGF, or VEGF. The wells were then washed three times, incubated 20 minutes with a substrate solution containing hydrogen peroxide and tetramethylbenzidine, and the reaction quenched with 2N sulfuric acid. Optical density was determined at 450 nm (wavelength correction 550 nm). All assays were performed in duplicate. Protein concentrations were calculated using a standard curve derived from known concentrations of the respective recombinant proteins. If the difference between duplicates exceeded 25%, the assay was repeated and initial results discarded. The assays had sensitivities of 5, 7, and 5 pg/ml for sFlt 1, PlGF, and VEGF, respectively, with inter- and intra-assay coefficients of variation of 7.6% and 3.3% for sFlt 1, 11.2% and 5.4% for PlGF, and 7.3% and 5.4% for VEGF.

Statistical Analysis

Chi-square and t tests were used in analyses of maternal or infant characteristics to compare categorical or continuous variables, respectively. Although arithmetic mean values of concentrations are given in text and figures, statistical testing was performed after logarithmic transformation unless noted otherwise. Adjustment was performed using logistic regression on logarithmically transformed concentrations.

Results

Of the 120 cases, 80 developed mild and 40 severe pre-eclampsia, including 3 with HELLP syndrome and 3 with eclampsia. Case patients were shorter than control patients, had a higher body mass index, and higher baseline blood pressure (Table 2). In addition, larger proportions of case patients had pregnancies complicated by pre-term delivery or small-for-gestational age (SGA) infants. Case patients contributed an average of 2.9 serum specimens to the study; controls, 2.6 specimens.

We first confirmed that sFlt-1, PlGF, and VEGF were altered in patients with pre-eclampsia at the time of active disease as compared to gestationally matched controls from this CPEP study group. Specimens drawn at the time of established clinical pre-eclampsia (endpoint specimens) had dramatically increased sFlt-1 levels, decreased PlGF levels, and decreased VEGF levels compared to controls with gestational ages (4382 vs. 1643 pg/ml sFlt1, $p<0.0001$; 137 vs. 669 pg/ml PlGF, $p<0.0001$; and 6.41 vs. 13.86 pg/ml VEGF, $p=0.06$) for cases and controls, respectively, in 23 gestational-age matched pairs) similar to prior published reports (Maynard et al., J. Clin. Invest. 111:649-658, 2003).

Figure 5A:
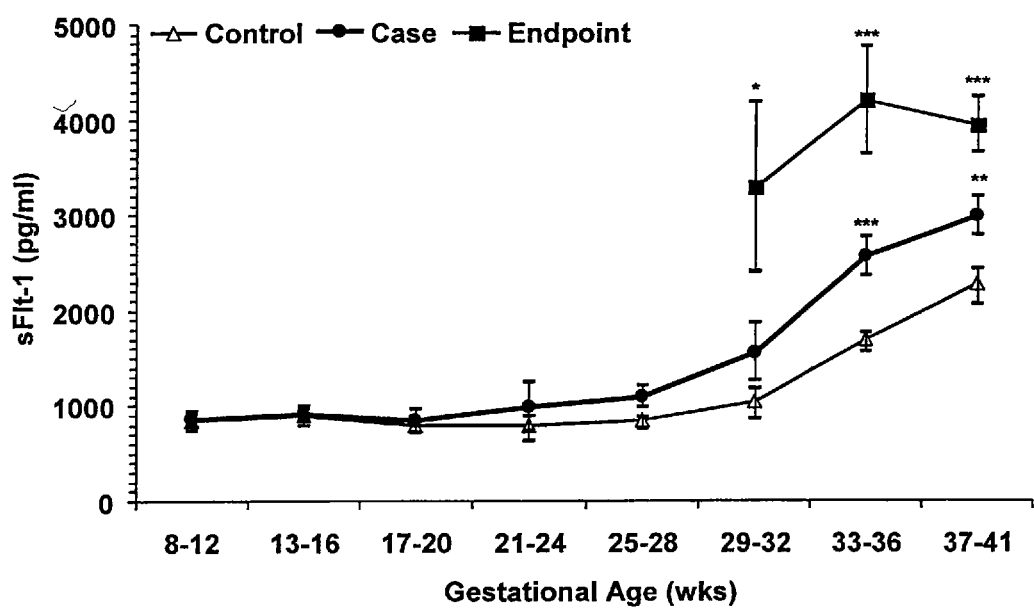
FIGS. 5A-5C are graphs showing sFlt-1 levels measured before and after the onset of pre-eclampsia by gestational age.
Figure 5B:
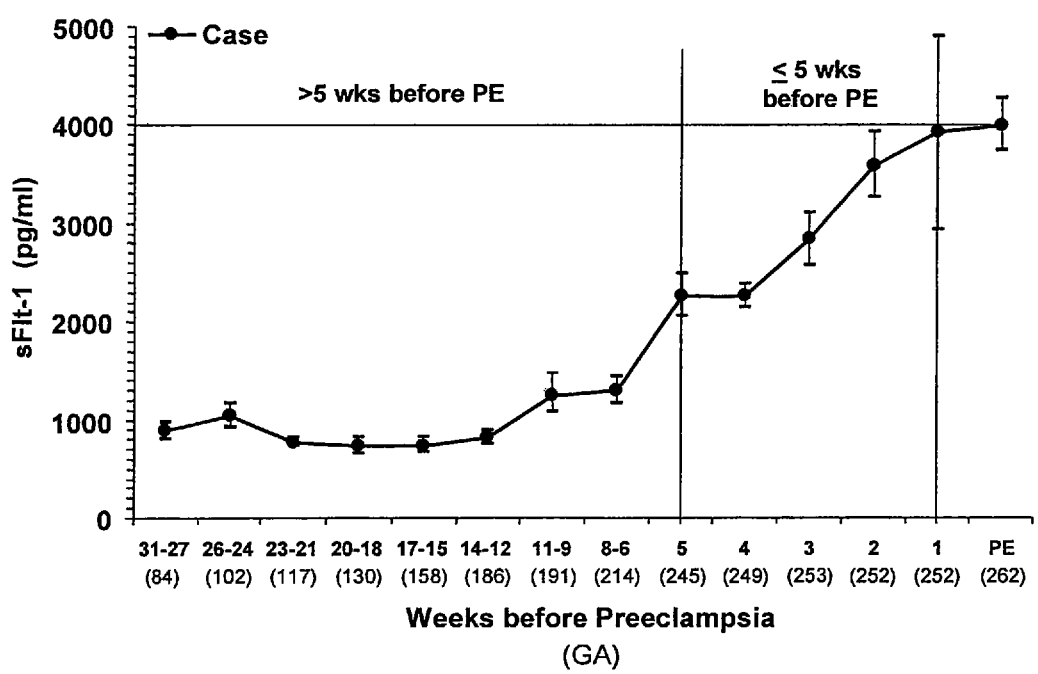
Figure 5C:
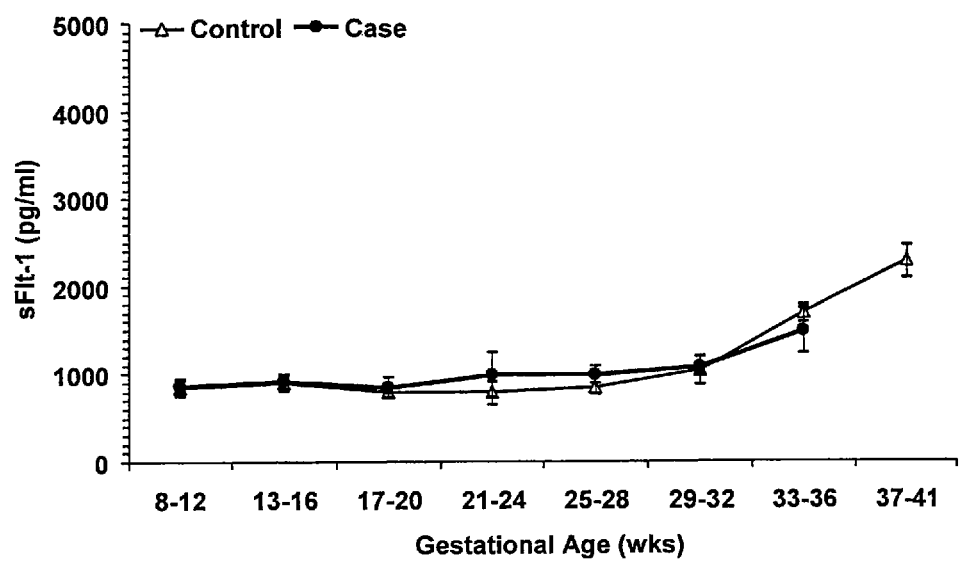

In order to evaluate the gestational pattern of sFlt-1, PlGF and VEGF levels, we measured circulating concentrations of sFlt-1, PlGF, and VEGF from serum specimens obtained from case patients and control patients within various gestational age windows. The gestational pattern of sFlt-1 protein for 120 pre-eclamptic and 120 control women is shown in FIG. 5A. sFlt-1 levels in control patients remained constant until 33-36 weeks, when they rose by approximately 145 pg/ml per week until labor and delivery. Among case patients before clinical symptoms, sFlt-1 appeared to begin to rise at 21-24 weeks, with a steeper rise and a statistically significant difference from controls at 29-32 weeks (FIG. 5A). Overall, differences between case and control patients measured before the onset of clinical symptoms were 17% ($p<0.05$) at mid-gestation. The end-point specimens were significantly elevated as compared to specimens drawn prior to the disease. In order to evaluate the mechanisms of sFlt-1 rise prior to the onset of clinical disease, we plotted sFlt-1 concentrations on all pre-eclamptics by weeks prior to the onset of pre-eclampsia (FIG. 5B). Mean sFlt-1 concentrations in specimens from case patients were plotted by completed weeks before onset of pre-eclampsia. Beginning at 5 weeks prior to pre-eclampsia, sFlt-1 concentrations rose substantially until 1 week prior to the onset of disease when they approached the concentrations observed in endpoint specimens. The increases in sFlt-1 at 4, 3, 2, and 1 week(s) before pre-eclampsia occurred with little change in mean gestational age and cannot be explained by late third trimester increases with advancing gestational age. From 8-6 to 5 weeks before pre-eclampsia sFlt-1 increased 962 pg/ml, while mean gestational age rose 31 days. About one-third of this increase in sFlt-1 cannot be attributed to advancing gestation. When sFlt-1 was graphed by gestational age in controls and in cases after removing specimens obtained <5 weeks before onset of pre-eclampsia, no substantial differences were observed (FIG. 5C). These data suggest that the higher sFlt-1 concentration in case patients prior to onset of pre-eclampsia is due to acute rises in sFlt-1 within the 5 weeks before onset of clinical disease.

Figure 6A:
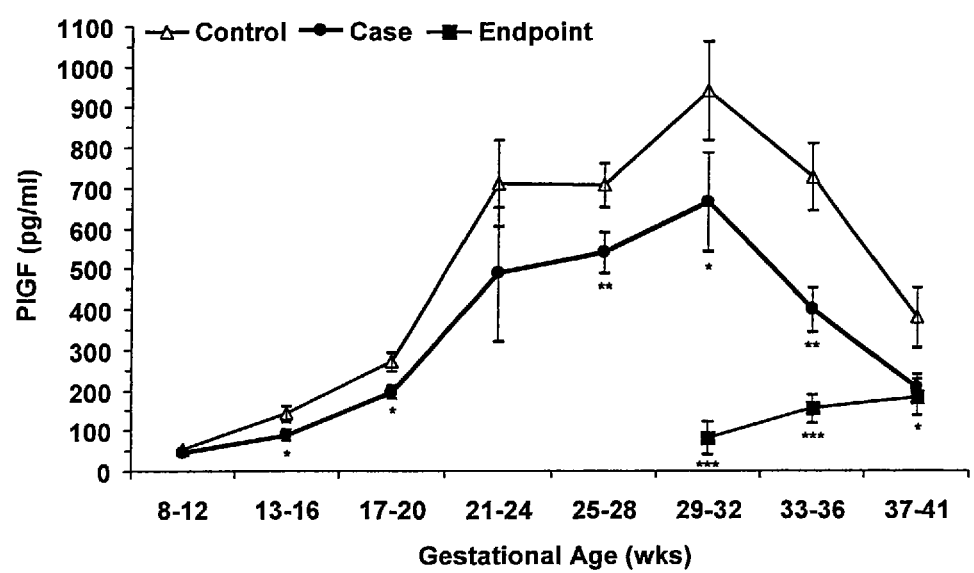
FIGS. 6A-6C are graphs showing the levels of PlGF before and after pre-eclampsia by gestational age.
Figure 6B:
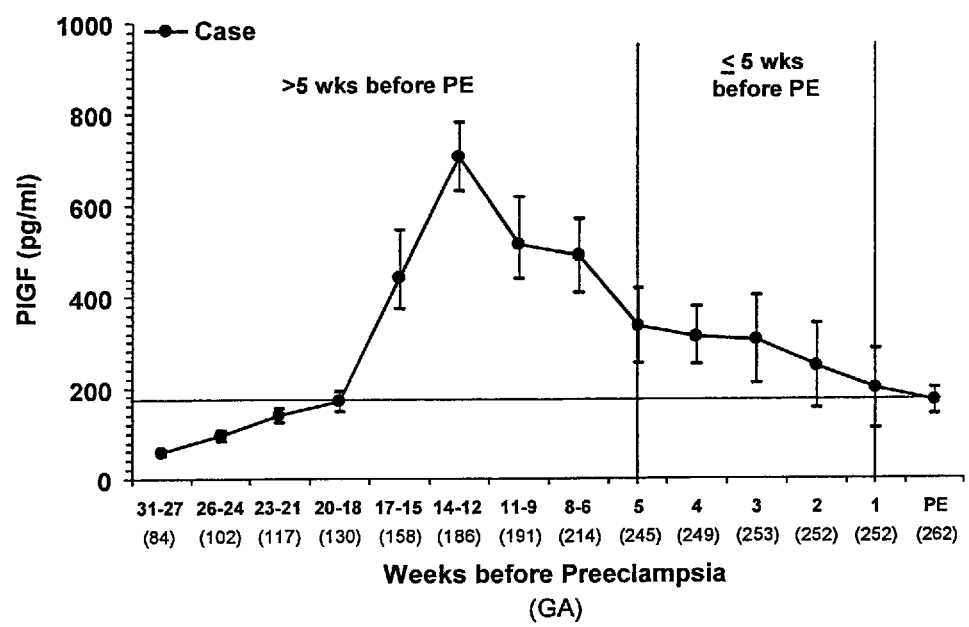
Figure 6C:
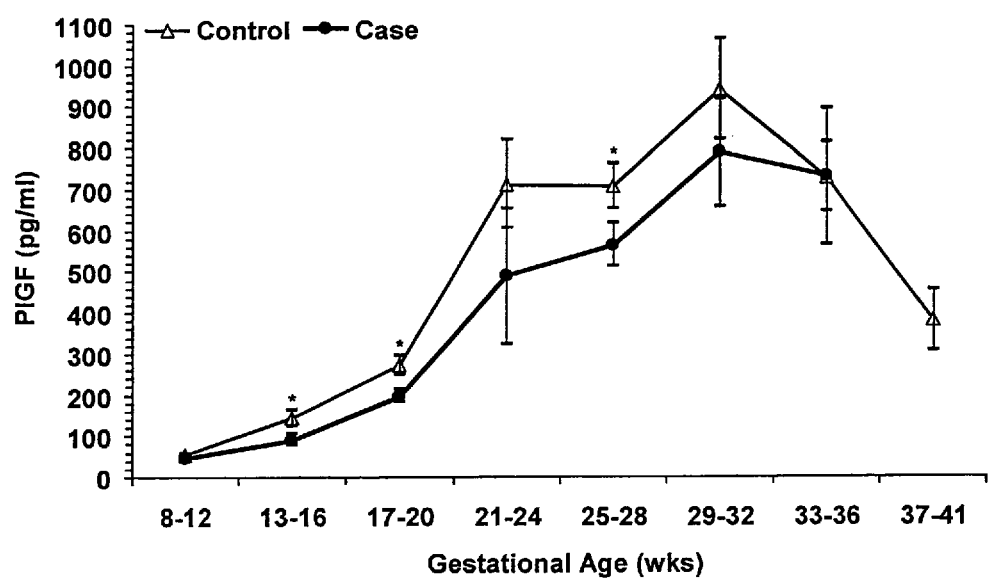

We then plotted the gestational pattern of PlGF protein in the same patient group as shown in FIG. 6A. Control PlGF protein concentrations rose during the first two trimesters, peaked at 29-32 weeks, and fell during late gestation. Among case patients, prior to pre-eclampsia, PlGF protein concentrations followed a similar gestational pattern, but were significantly lower than controls from 13-16 weeks. Overall, differences in PlGF between cases patients and controls measured before the onset of clinical symptoms were 35% ($p<0.0001$) at mid-gestation. PlGF levels in cases prior to onset of pre-eclampsia is depicted by weeks before pre-eclampsia (FIG. 6B), and by gestational age after removing specimens <5 weeks before pre-eclampsia (FIG. 6C). By 1 week prior to onset of pre-eclampsia, concentrations approached those observed after onset of pre-eclampsia (FIG. 6B). Compared to controls, PlGF levels from case patients were moderately reduced remote from delivery, with more substantial reductions at 5 and 3 weeks before delivery. Concentrations from control patients remained high from 17-15 through 3 weeks before delivery, then fell dramatically. The graph showing PlGF levels excluding specimens obtained <5 weeks before pre-eclampsia indicates a smaller decrease in cases relative to controls at 29-32 weeks of gestation and none at all in specimens obtained from case patients at 33-36 weeks (FIG. 6C). This suggests that the fall in PlGF concentrations in the weeks prior to the disease was responsible for the dramatically low levels of PlGF noted at the onset of disease (or end point specimens shown in FIG. 6A).

VEGF concentrations throughout pregnancy were very low and similar in controls and cases before pre-eclampsia, except for a significant decrease in case patients at 37-41 weeks. Mean VEGF concentrations at 23-32 weeks in cases excluding specimens obtained 5 weeks before pre-eclampsia did not differ significantly from controls (11.6 vs. 12.8 pg/ml), whereas concentrations in cases including specimens <5 weeks before delivery did (5.1 vs. 12.8 pg/ml, $p<0.01$). At 33-41 weeks case VEGF concentrations >5 or <5 weeks before pre-eclampsia were higher and lower than controls, respectively (11.2 pg/ml and 8.3 vs. 9.7 pg/ml), although these differences were not significant.

Figure 7A:
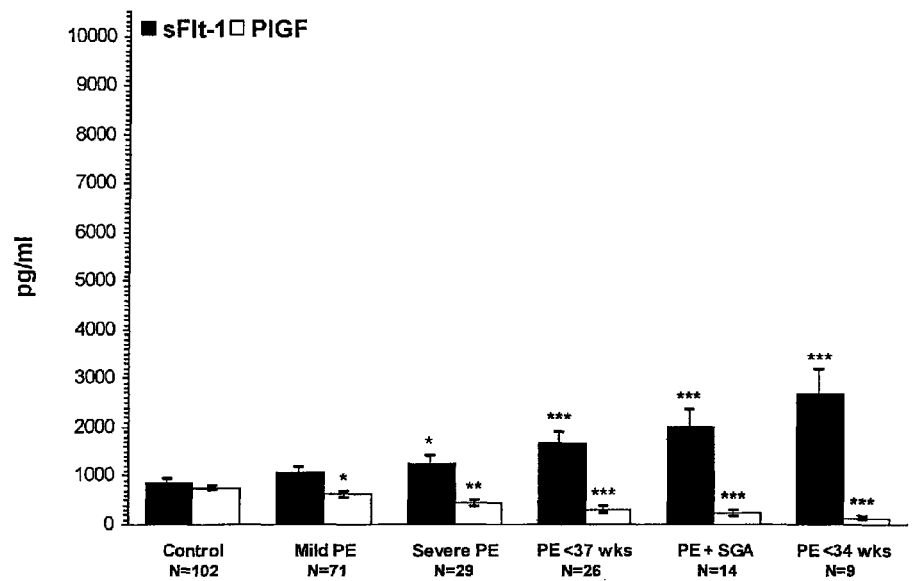
FIGS. 7A and 7B are graphs showing sFlt-1 and PlGF levels by pre-eclampsia status and severity.
Figure 7B:
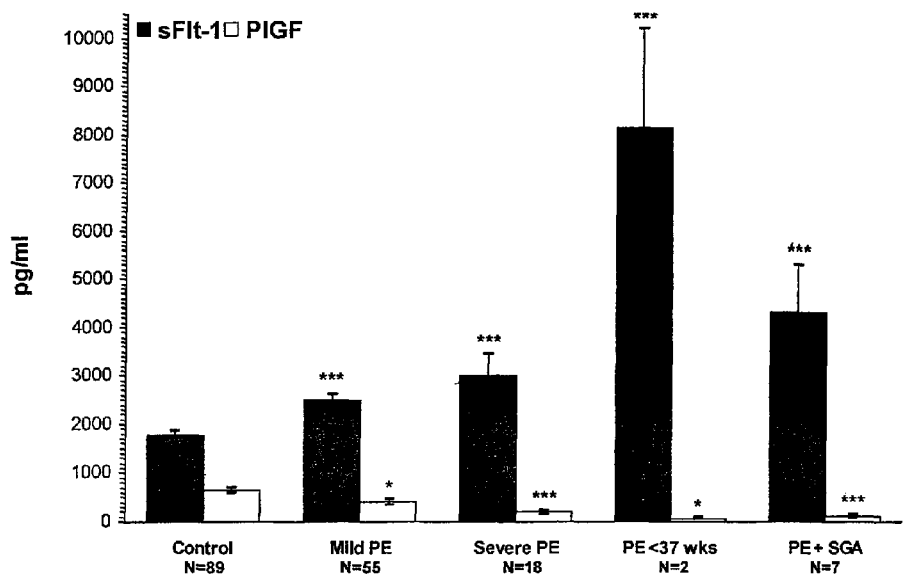

FIG. 7 depicts sFlt-1 and PlGF at 23-32 weeks (FIG. 7A) and 33-41 weeks (FIG. 7B) by pre-eclampsia status and severity. The graphs show that sFlt-1 increases and PlGF decreases before onset of pre-eclampsia were associated with disease severity, time of onset, and the presence of an SGA infant. At 23-32 weeks, sFlt-1 and PlGF in case patients with an SGA infant before onset of pre-eclampsia were significantly higher or lower, respectively, than corresponding concentrations in control patients with an SGA infant. Moreover, in comparison to control patients who delivered pre-term, case patients with pre-term delivery had higher sFlt-1 and significantly lower PlGF.

To determine whether concentrations of sFlt-1 or PlGF prior to clinical signs of pre-eclampsia were associated with the risk of this condition, we calculated odds ratios for pre-eclampsia for each quartile of control values of sFlt-1 and PlGF, as compared to the lowest or highest quartile, respectively (Table 4). We also examined the pre-eclampsia risk of the extreme quartiles with respect to all other quartiles, as follows. For specimens obtained in the second- and early third-trimester, the lowest quartile of PlGF was associated with an increased risk of preterm (<37 weeks gestation) pre-eclampsia (OR 7.4, 95% CI 1.8 to 30.2 for 13-20 week specimens; OR 7.9, 95% CI 2.9 to 21.5 for 21-32 week specimens). A level of PlGF in the lowest quartile, however, was not a significant predictor of term (>37 weeks) pre-eclampsia. For sFlt-1, associations with pre-eclampsia were observed only closer to disease onset. An sFlt-1 level in the highest quartile between 21 to 32 weeks gestation (but not earlier) predicted preterm pre-eclampsia (OR 5.1, 95 percent CI 2.0 to 13.0), and a level in the highest quartile between 33 and 41 weeks (but not earlier) predicted term pre-eclampsia (OR 6.0, 95 percent CI 2.9 to 12.5). This is consistent with FIG. 5B, which shows that elevation of sFlt-1 occurs largely within 5 weeks of onset of clinical disease. The lowest quartile of VEGF was not predictive of pre-eclampsia.

PlGF and VEGF. Three pre-eclampsia subgroups—severe pre-eclampsia, early onset of disease, and SGA infants—had higher sFlt-1 and lower PlGF concentrations at 23-32 weeks and at 33-41 weeks than controls or women with mild pre-eclampsia. We have also demonstrated a small but significant decrease in free PlGF beginning early in the second trimester among women destined to develop pre-eclampsia. These results demonstrate that a decrease in PlGF levels may be a useful predictor of early onset pre-eclampsia.

We describe here for the first time the gestational pattern of sFlt-1 in normal pregnancy, observing relatively stable levels throughout gestation followed by a steady increase beginning at 33-36 weeks. This rise corresponds to the late gestational fall in PlGF observed in normal pregnancy by others (Torry et al., *J. Soc. Gynecol. Invest.* 10:178-188, 1998; Taylor et al., *Am. J. Obstet. Gynecol.* 188:177-182, 2003) and in the results described herein. The temporal association, together with the knowledge that sFlt-1 interferes with PlGF ELISA measurement (Maynard et al., supra) suggests that the fall in free PlGF levels during late gestation may be due to the rise in sFlt-1 levels. During first and second trimesters, when placental growth is needed to keep pace with increasing fetal demands, PlGF concentrations are high and sFlt-1 concentrations are low, creating a relatively pro-angiogenic state. Later in gestation, when placental vascular growth may need to be tempered and halted, there is a rise in the anti-angiogenic sFlt-1 and resulting decrease in PlGF. In women with pre-eclampsia, the sFlt-1 rise begins earlier in gestation, approximately five weeks before symptom onset, at about 29-32 weeks gestation on average. Thus, in pre-eclampsia, the anti-angiogenic "brakes" may be applied too soon and too strongly, resulting in an exaggeration of a normal physiologic process which arrests placental growth. It seems clear that the pathologic placental changes

TABLE 4

Odds Ratios (OR) for Pre-eclampsia at <37 and ≥37 Weeks Prior to Clinical Signs by Quartiles of Total sFlt-1 and Free PlGF in Controls at 13-20, 21-32, and 33-41 Weeks Gestation

| sFlt-1 (pg/ml) | Controls N | PE < 37 wks N | OR * | PE ≥ 37 wks N | OR * | PlGF (pg/ml) | Controls N | PE < 37 wks N | OR * | PE ≥ 37 wks N | OR * |
|---|---|---|---|---|---|---|---|---|---|---|---|
| | | | | | | 13-20 wks | | | | | |
| Q4: >1047 | 25 | 6 | 1.3 (0.4-5.0) | 20 | 1.5 (0.6-3.7) | Q4: >307 | 25 | 4 | 1.0 Referent | 4 | 1.0 Referent |
| Q3: >698-1047 | 25 | 8 | 2.2 (0.6-7.8) | 23 | 1.9 (0.8-4.5) | Q3: >160-307 | 25 | 2 | 0.6 (0.1-3.5) | 22 | 5.6 (1.7-19.0) |
| Q2: >531-698 | 25 | 4 | 0.5 (0.1-2.3) | 16 | 1.1 (0.4-2.7) | Q2: >87-160 | 25 | 6 | 1.9 (0.4-8.2) | 26 | 6.4 (1.9-22.1) |
| Q1: ≤531 | 25 | 6 | 1.0 Referent | 16 | 1.0 Referent | Q1: ≤87 | 25 | 12 | 9.6 (1.6-57.6) | 23 | 6.7 (1.6-27.5) |
| | | | | | | 21-32 wks | | | | | |
| Q4: >1131 | 25 | 16 | 4.7 (1.3-16.6) | 18 | 1.7 (0.7-4.4) | Q4: >1021 | 25 | 1 | 1.0 Referent | 14 | 1.0 Referent |
| Q3: >743-1131 | 26 | 5 | 1.4 (0.3-6.0) | 21 | 1.7 (0.7-4.2) | Q3: >677-1021 | 26 | 1 | 1.1 (0.1-18.2) | 19 | 1.2 (0.5-3.1) |
| Q2: >512-743 | 25 | 1 | 0.3 (0.0-2.8) | 21 | 1.9 (0.8-4.7) | Q2: >363-677 | 25 | 5 | 5.3 (0.6-49.3) | 20 | 1.3 (0.5-3.2) |
| Q1: ≤512 | 26 | 4 | 1.0 Referent | 14 | 1.0 Referent | Q1: ≤363 | 26 | 19 | 19.6 (2.3-163.8) | 21 | 1.2 (0.5-3.1) |
| | | | | | | 33-41 wks | | | | | |
| Q4: >2191 | 22 | | | 44 | 7.5 (2.6-21.8) | Q4: >948 | 22 | | | 6 | 1.0 Referent |
| Q3: >1633-2191 | 22 | | | 12 | 1.7 (0.5-5.5) | Q3: >377-948 | 22 | | | 18 | 2.7 (0.9-8.3) |
| Q2: >1287-1633 | 22 | | | 7 | 1.0 (0.3-3.3) | Q2: >175-377 | 22 | | | 19 | 2.8 (0.9-8.5) |
| Q1: ≤1287 | 23 | | | 8 | 1.0 Referent | Q1: ≤175 | 23 | | | 28 | 4.1 (1.4-12.2) |

* Odds ratio adjusted for gestational age and body mass index (with 95% CI). OR with 95% CI > 1.0 in bold type. Case specimens were obtained prior to clinical signs of preeclampsia.

These results demonstrate that sFlt-1 levels begin to rise dramatically about 5 weeks before the onset of pre-eclampsia symptoms. Parallel with the rise in sFlt-1, free PlGF and free VEGF levels fall, suggesting that the decrease in PlGF and VEGF may be due at least partially to antagonism by sFlt-1 and not due to a decrease in placental production of that characterize pre-eclampsia occur early in gestation (10-14 weeks), well before the dramatic rise in sFlt-1. The resulting placental ischemia itself may enhance sFlt-1 production, ultimately triggering a burst in sFlt-1.

In addition to the large differences seen in the five weeks prior to the development of clinical symptoms, women destined to develop pre-eclampsia had small, but statistically significant, decreases in free PlGF as early as 13-16 weeks gestation. This fall in PlGF generally was not accompanied by a reciprocal increase in sFlt-1 levels. However, there was a tendency towards slightly higher sFlt-1 levels in cases during the first trimester though it was not statistically significant (For example at the 17-20 week window, average sFlt-1 levels in cases were 865.77 pg/ml vs. 795.25 in controls). This decrease in PlGF levels early on in gestation might reflect a smaller placental production of PlGF in pregnancies compromised by conditions such as pre-eclampsia or SGA. Importantly, in patients with pre-eclampsia complicated by SGA, we found a statistically significant increase in both sFlt-1 elevation and PlGF fall prior to the disease presentation. It is also possible that there is no change in placental production of PlGF in pre-eclamptics and that elevation of local sFlt-1 levels in the placenta may contribute to the decrease in circulating free PlGF. This is supported by the finding that placental PlGF, measured by immunohistochemistry, is not altered in pre-eclampsia (Zhou et al., Am. J. Pathol. 160:1405-1423, 2002).

In summary, we have shown that sFlt-1 starts rising in pre-eclampsia at least 5 weeks before the onset of clinical disease which is accompanied by decreases in circulating free PlGF and free VEGF. Decreased PlGF during the first trimester may serve as a predictor of pre-eclampsia and elevated sFlt-1 may serve as a predictor of proximity to clinical disease. This data in conjunction with the animal work described above demonstrating sFlt-1 alone induces pre-eclampsia like symptoms in rodents suggests a probable etiological role for sFlt-1 in the pathogenesis of pre-eclampsia. Our limited data on SGA infants and preterm delivery in controls, as compared to case patients, suggest that the increased alterations in protein levels observed in pre-eclamptic pregnancies with an SGA infant are more substantial than a difference due only to intrauterine growth restriction or pre-term delivery in the absence of pre-eclampsia.

Figure 8:
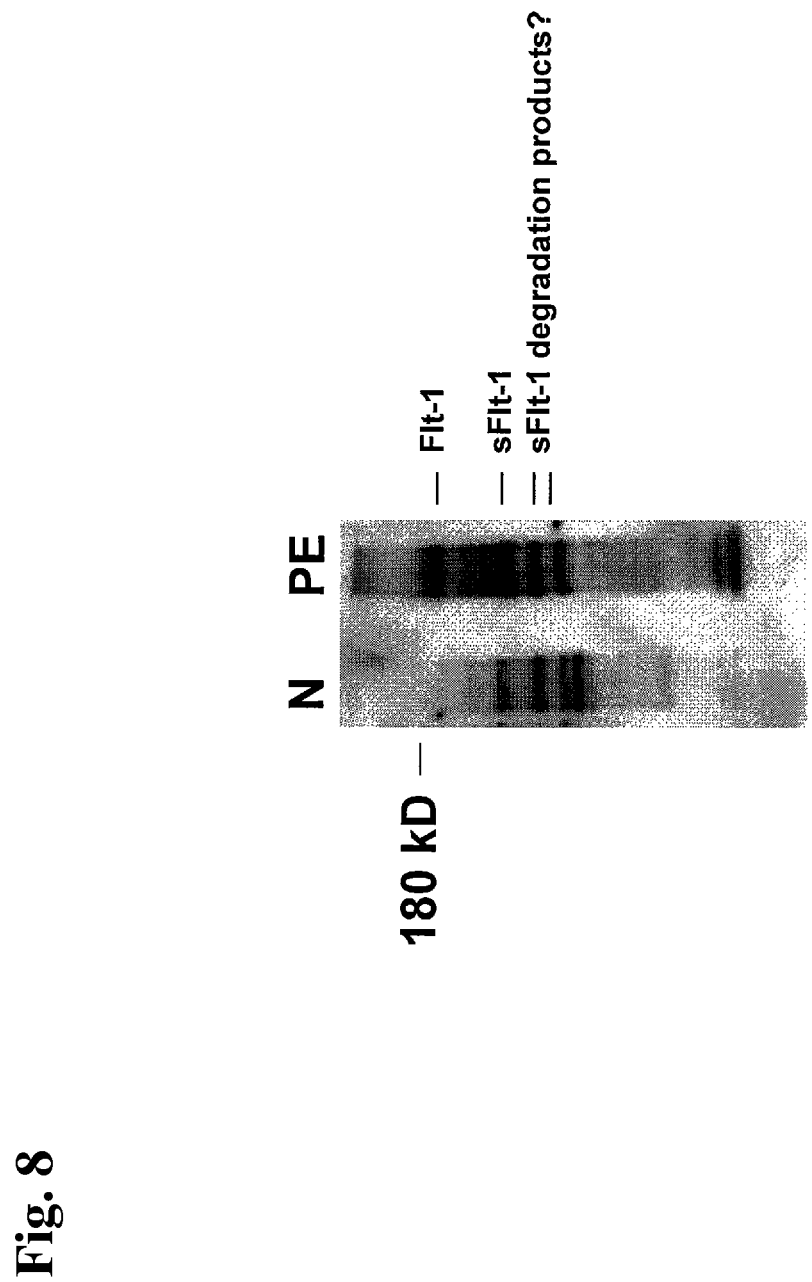
FIG. 8 is an autoradiogram showing the expression of flt, sFlt-1, and related variants or fragments in PBMCs isolated from normal and preeclamptic patients. Protein lysates were analyzed by western blots using an antibody that recognizes the N-terminus of Flt-1 protein.

Example 9. sFlt-1 Protein and Protein Fragments Detected in Monocytes from Normal and Preeclamptic Patients Peripheral blood mononuclear cells, rich in monocytes, were isolated from normal and pre-eclamptic patients and used to measure the leves of sFlt-1 and sFlt-1 fragments. Protein extracts were prepared from the PBMCs and Flt-1/sFlt-1 levels were analyzed by Western blots using an antibody that recognizes the N-terminus of Flt-1 protein (a region common to both proteins). The results of this experiment showed increased Flt-1 and sFlt-1 levels in the monocytes from pre-eclamptic patients (FIG. 8). In addition several bands were detected that had a faster migration than full-length sFlt-1. These faster migrating bands may be degradation products, alternatively spliced isoforms, enzymatic cleavage products, or other forms of sFlt-1.

Example 10. sFlt-1 Protein Levels as a Diagnostic Indicator of Cardiovascular Conditions in Women with a History of Pre-Eclampsia Women with a history of pre-eclampsia have been shown to have a propensity to develop cardiovascular conditions (see for example Kestenbaum et al., Am. J. Kidney Dis. 42:982-989, 2003). Given our discovery of the use of s-Flt-1 as a diagnostic indicator of pre-eclampsia or eclampsia or a predisposition to pre-eclampsia or eclampsia, a study was performed to determine if sFlt-1 could also be used as a diagnostic indicator of a propensity to develop cardiovascular conditions or events in women who have a history of preeclampsia. The results of this study are shown in Table 5.

We examined 29 normotensive women with a history of preeclampsia and 32 normotensive women with previous normal pregnancies at 18.0±9.7 months postpartum in the General Clinical Research Centers at the Massachusetts Institute of Technology in collaboration with Dr. Ravi Thadhani at the Massachussetts General Hospital. Since preeclampsia often presents near term and other disorders can lead to preterm delivery, to prevent misclassification of pregnancy outcome, all normotensive women had delivered at term (>38 weeks). Women with current pregnancy, diabetes or a history of gestational diabetes, chronic hypertension, proteinuria or serum creatinine >1.0 mg/dL were excluded. After providing written informed consent, subjects underwent a history and physical examination and a urine pregnancy test. Blood was collected on the morning after an overnight fast for measurement of free VEGF and sFlt-1. Samples were processed immediately, stored at −80° C. for no longer than 18 months and were thawed only for the current study. Commercial assay ELISA kits were used for sFlt-1 and free VEGF (R&D systems, Minnesota USA). The intra- and inter-assay co-eficent of variance (CVs) for sFlt-1 and VEGF were 3.5 and 5.6, and 8.1 and 10.9, respectively. All samples were run in duplicate by technicians blinded to pregnancy outcome.

Univariate comparisons between the pregnancy outcome groups were performed using two-sample t tests, Wilcoxon rank sum test or Fisher exact test as appropriate. Logistic regression was used to calculate odds ratios for having had prior preeclampsia given levels of postpartum markers, and to adjust for potential confounding.

TABLE 5

Postpartum sFlt-1 data according to pregnancy outcome.

|  | Preeclampsia N = 29 | Normotensive N = 32 | P |
| --- | --- | --- | --- |
| Age (years) | 33.7 ± 5.8 | 30.7 ± 7.1 | 0.08 |
| Race (% Caucasian) | 86 | 84 | 0.6 |
| Months postpartum | 18.0 ± 10 | 18.0 ± 10 | 1.0 |
| Body mass index (kg/m$^2$) | 29.2 ± 7.8 | 25.0 ± 5.8 | 0.02 |
| Systolic blood pressure (mmHg) | 111 ± 10 | 105 ± 8 | 0.01 |
| Diastolic blood pressure (mmHg) | 73 ± 10 | 68 ± 7 | 0.04 |
| Mean arterial blood pressure (mmHg)* | 86 ± 10 | 81 ± 7 | 0.01 |
| Oral or subcutaneous contraception (%) | 31 | 34 | 0.8 |
| Fasting glucose (mg/dL) | 81 ± 7 | 80 ± 6 | 0.5 |
| Soluble fms-like tyrosine kinase (pg/ml) | 41.6 ± 6.7 | 30.4 ± 10.2 | <0.01 |

Continuous variables are reported as mean ± standard deviation or median (interquartile range) as appropriate.

These results indicate that women with a history of pre-eclampsia during pregnancies showed elevated levels of sFlt-1 for an extended period of time after the pregnancy. Given that statistical analysis has shown that women with a history of pre-eclampsia or eclampsia have a predisposition to develop cardiovascular conditions, these results provide support for the use of sFlt-1 post-partum levels as a diagnostic indicator of a cardiovascular condition or a propensity to develop a cardiovascular condition.

Diagnostics

The present invention features diagnostic assays for the detection of pre-eclampsia, eclampsia, or the propensity to develop such conditions. Levels of VEGF, PlGF, or sFlt-1, either free or total levels, are measured in a subject sample and used as an indicator of pre-eclampsia, eclampsia, or the propensity to develop such conditions.

In one embodiment, a metric is used to determine whether a relationship between levels of at least two of the proteins is indicative of pre-eclampsia or eclampsia. Standard methods may be used to measure levels of VEGF, PlGF, or sFlt-1 polypeptide in any bodily fluid, including, but not limited to, urine, serum, plasma, saliva, amniotic fluid, or cerebrospinal fluid. Such methods include immunoassay, ELISA, western blotting using antibodies directed to VEGF, PlGF or sFlt-1, and quantitative enzyme immunoassay techniques such as those described in Ong et al. (*Obstet. Gynecol.* 98:608-611, 2001) and Su et al. (*Obstet. Gynecol.*, 97:898-904, 2001). ELISA assays are the preferred method for measuring levels of VEGF, PlGF, or sFlt-1. Elevated serum levels of sFlt-1 are considered a positive indicator of pre-eclampsia. This value of sFlt-1 may be preferentially 2 ng/ml or more. Additionally, any detectable alteration in levels of sFlt-1, VEGF, or PlGF relative to normal levels is indicative of eclampsia, pre-eclampsia, or the propensity to develop such conditions. Preferably, sFlt-1 is measured, more preferably measurement of VEGF and PlGF are combined with this measurement, and most preferably all three proteins (or mRNA levels indicative of protein levels) are measured. In additional preferred embodiments, the body mass index (BMI) and gestational age of the fetus is also measured and included the diagnostic metric.

In another embodiment, the PAAI (sFlt-1/VEGF+PlGF) is used as an anti-angiogenic index that is diagnostic of pre-eclampsia, eclampsia, or the propensity to develop such conditions. If the PAAI is greater than 10, more preferably greater than 20, then the subject is considered to have pre-eclampsia, eclampsia, or to be in imminent risk of developing the same. The PAAI (sFlt-1/VEGF+PlGF) ratio is merely one example of a useful metric that may be used as a diagnostic indicator. It is not intended to limit the invention. Virtually any metric that detects an alteration in the levels of any of sFlt-1, PlGF, or VEGF in a subject relative to a normal control may be used as a diagnostic indicator.

Expression levels of particular nucleic acids or polypeptides may be correlated with a particular disease state (e.g., pre-eclampsia or eclampsia), and thus are useful in diagnosis. Oligonucleotides or longer fragments derived from a sFlt-1, PlGF, or VEGF nucleic acid sequence may be used as a probe not only to monitor expression, but also to identify subjects having a genetic variation, mutation, or polymorphism in an sFlt-1, PlGF, or VEGF nucleic acid molecule that are indicative of a predisposition to develop the conditions. Such polymorphisms are known to the skilled artisan and are described, for example, by Parry et al. (*Eur. J Immunogenet.* 26:321-3, 1999). A survey of the GenBank database (www.ncbi.nlm.nih.gov) reveals at least 330 known polymorphisms in the gene and the promoter region of Flt-1/sFlt-1. These polymorphisms may affect sFlt-1 nucleic acid or polypeptide expression levels or biological activity. Detection of genetic variation, mutation, or polymorphism relative to a normal, reference sample can be as a diagnostic indicator of pre-eclampsia, eclampsia, or the propensity to develop pre-eclampsia or eclampsia.

Such genetic alterations may be present in the promoter sequence, an open reading frame, intronic sequence, or untranslated 3' region of an sFlt-1 gene. Information related to genetic alterations can be used to diagnose a subject as having pre-eclampsia, eclampsia, or a propensity to develop such conditions. As noted throughout, specific alterations in the levels of biological activity of sFlt-1, VEGF, and/or PlGF can be correlated with the likelihood of pre-eclampsia or eclampsia, or the predisposition to the same. As a result, one skilled in the art, having detected a given mutation, can then assay one or more metrics of the biological activity of the protein to determine if the mutation causes or increases the likelihood of pre-eclampsia or eclampsia.

In one embodiment, a subject having pre-eclampsia, eclampsia, or a propensity to develop such conditions will show an increase in the expression of a nucleic acid encoding sFlt-1 or an alteration in PlGF or VEGF levels. Methods for detecting such alterations are standard in the art and are described in Ausubel et al., supra. In one example northern blotting or real-time PCR is used to detect sFlt-1, PlGF, or VEGF mRNA levels.

In another embodiment, hybridization with PCR probes that are capable of detecting an sFlt-1 nucleic acid molecule, including genomic sequences, or closely related molecules, may be used to hybridize to a nucleic acid sequence derived from a subject having pre-eclampsia or eclampsia or at risk of developing such conditions. The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques may be used to identify mutations indicative of a pre-eclampsia or eclampsia in an sFlt-1 nucleic acid molecule, or may be used to monitor expression levels of a gene encoding an sFlt-1 polypeptide (for example, by Northern analysis, Ausubel et al., supra).

In yet another embodiment, humans may be diagnosed for a propensity to develop pre-eclampsia or eclampsia by direct analysis of the sequence of an sFlt-1, VEGF, or PlGF nucleic acid molecule.

A subject having pre-eclampsia, eclampsia, or a propensity to develop such conditions will show an increase in the expression of an sFlt-1 polypeptide. The sFlt-1 polypeptide can include full-length sFlt-1, degradation products, alternatively spliced isoforms of sFlt-1, enzymatic cleavage products of sFlt-1, and the like. An antibody that specifically binds an sFlt-1 polypeptide may be used for the diagnosis of pre-eclampsia or eclampsia or to identify a subject at risk of developing such conditions. A variety of protocols for measuring an alteration in the expression of such polypeptides are known, including immunological methods (such as ELISAs and RIAs), and provide a basis for diagnosing pre-eclampsia or eclampsia or a risk of developing such conditions. Again, an increase in the level of the sFlt-1 polypeptide is diagnostic of a subject having pre-eclampsia, eclampsia, or a propensity to develop such conditions.

In one embodiment, the level of sFlt-1, VEGF, or PlGF polypeptide or nucleic acid, or any combination thereof, is measured at least two different times and an alteration in the levels as compared to normal reference levels over time is used as an indicator of pre-eclampsia, eclampsia, or the propensity to develop such conditions.

The level of sFlt-1, VEGF, or PlGF in the bodily fluids of a subject having pre-eclampsia, eclampsia, or the propensity to develop such conditions may be altered by as little as 10%, 20%, 30%, or 40%, or by as much as 50%, 60%, 70%, 80%, 90% or more relative to the level of sFlt-1, VEGF, or PlGF in a normal control. The level of sFlt-1 present in the bodily fluids of a subject having pre-eclampsia, eclampsia, or the propensity to develop such conditions may be increased by 1.5-fold, 2-fold, 3-fold, 4-fold or even by as much as 10-fold or more relative to levels in a normal control subject.

In one embodiment, a subject sample of a bodily fluid (e.g., urine, plasma, serum, amniotic fluid, or cerebrospinal fluid) is collected early in pregnancy prior to the onset of pre-eclampsia symptoms. In another example, the sample can be a tissue or cell collected early in pregnancy prior to the onset of pre-eclampsia symptoms. Non-limiting examples include placental tissue, placental cells, endothelial cells, and leukocytes such as monocytes. In humans, for example, maternal blood serum samples are collected from the antecubital vein of pregnant women during the first, second, or third trimesters of the pregnancy. Preferably, the assay is carried out during the first trimester, for example, at 4, 6, 8, 10, or 12 weeks, or during the second trimester, for example at 14, 16, 18, 20, 22, or 24 weeks. Such assays may also be conducted at the end of the second trimester or the third trimester, for example at 26, 28, 30, 32, 34, or 36 weeks. It is preferable that levels of sFlt-1, VEGF, or PlGF be measured twice during this period of time. For the diagnosis of post-partum pre-eclampsia or eclampsia, assays for sFlt-1, VEGF, or PlGF may be carried out postpartum.

In one particular example, serial blood samples can be collected during pregnancy and the levels of soluble sFlt-1 determined by ELISA. In one study using this technique, the alternatively spliced mRNA encoding sFlt-1 is highly expressed by trophoblast cells and the protein was readily detectable in the plasma of pregnant women. It was observed that the levels of sFlt-1 increased approximately 3-fold between 20 and 36 weeks gestation. Levels were observed to be significantly higher in high-risk women who subsequently went on to develop pre-eclampsia (Charnock-Jones et al., *J. Soc. Gynecol. Investig.* 10(2):230, 2003).

In veterinary practice, assays may be carried out at any time during the pregnancy, but are, preferably, carried out early in pregnancy, prior to the onset of pre-eclampsia symptoms. Given that the term of pregnancies varies widely between species, the timing of the assay will be determined by a veterinarian, but will generally correspond to the timing of assays during a human pregnancy.

The diagnostic methods described herein can be used individually or in combination with any other diagnostic method described herein for a more accurate diagnosis of the presence of, severity of, or estimated time of onset of pre-eclampsia or eclampsia. In addition, the diagnostic methods described herein can be used in combination with any other diagnostic methods determined to be useful for the accurate diagnosis of the presence of, severity of, or estimated time of onset of pre-eclampsia or eclampsia.

The diagnostic methods described herein can also be used to monitor and manage pre-eclampsia or eclampsia in a subject. In one example, if a subject is determined to have a serum sFlt-1 protein level of 10 ng/mL and a serum level of free PlGF of 100 pg/mL, then VEGF can be administered until the serum PlGF level rises to approximately 400 pg/mL. In this embodiment, the levels of sFlt-1, PlGF, and VEGF, or any and all of these, are measured repeatedly as a method of not only diagnosing disease but monitoring the treatment and management of the pre-eclampsia and eclampsia.

The invention also features diagnostic assays for the detection of a cardiovascular condition or a propensity to develop a cardiovascular condition. In a preferred embodiment, sFlt-1 levels are measured in women with a history of pre-eclampsia or eclampsia and compared to sFlt-1 levels from a reference sample. Reference samples preferably include samples taken from women with previous pregnancies and no history of pre-eclampsia or eclampsia. Alterations in the levels of sFlt-1 polypeptide or nucleic acid as compared to the reference sample can be used to diagnose a cardiovascular condition or to predict a propensity to develop a cardiovascular condition. Alterations in the nucleic acid sequence of sFlt-1, PlGF, or VEGF as compared to a reference sequence can also be used to diagnose a cardiovascular condition or to predict a propensity to develop a cardiovascular condition. Any of the diagnostic methods and metrics described above can be used to monitor women with a history of pre-eclampsia or eclampsia postpartum or to diagnose a cardiovascular condition or to predict a propensity to develop a cardiovascular condition. Post-partum monitoring can be performed on a regular basis (e.g., once a month, once every six months, yearly, every other year, or less frequently) to assist in the diagnosis, prediction, or prevention of future cardiovascular events or conditions.

Diagnostic Kits

The invention also provides for a diagnostic test kit. For example, a diagnostic test kit can include antibodies to sFlt-1, VEGF, or PlGF, and means for detecting, and more preferably evaluating, binding between the antibodies and the sFlt-1, VEGF, or PlGF polypeptide. For detection, either the antibody or the sFlt-1, VEGF, or PlGF polypeptide is labeled, and either the antibody or the sFlt-1, VEGF, or PlGF polypeptide is substrate-bound, such that the sFlt-1, VEGF, or PlGF polypeptide-antibody interaction can be established by determining the amount of label attached to the substrate following binding between the antibody and the sFlt-1, VEGF, or PlGF polypeptide. A conventional ELISA is a common, art-known method for detecting antibody-substrate interaction and can be provided with the kit of the invention. sFlt-1, VEGF, or PlGF polypeptides can be detected in virtually any bodily fluid including, but not limited to urine, serum, plasma, saliva, amniotic fluid, or cerebrospinal fluid. A kit that determines an alteration in the level of sFlt-1, VEGF, or PlGF polypeptide relative to a reference, such as the level present in a normal control, is useful as a diagnostic kit in the methods of the invention. Desirably, the kit will contain instructions for the use of the kit. In one example, the kit contains instructions for the use of the kit for the diagnosis of pre-eclampsia, eclampsia, or the propensity to develop pre-eclampsia or eclampsia. In another example, the kit contains instructions for the diagnosis of cardiovascular conditions or the propensity to develop cardiovascular conditions. In yet another example, the kit contains instructions for the use of the kit to monitor therapeutic treatment or dosage regimens.

Screening Assays

As discussed above, the expression of an sFlt-1 nucleic acid or polypeptide is increased in a subject having pre-eclampsia, eclampsia, or a propensity to develop such conditions. Based on these discoveries, compositions of the invention are useful for the high-throughput low-cost screening of candidate compounds to identify those that modulate the expression of a sFlt-1, VEGF, or PlGF polypeptide or nucleic acid molecule whose expression is altered in a subject having a pre-eclampsia or eclampsia.

Any number of methods are available for carrying out screening assays to identify new candidate compounds that alter the expression of a sFlt-1, VEGF, or PlGF nucleic acid molecule. In one working example, candidate compounds are added at varying concentrations to the culture medium of cultured cells expressing a sFlt-1, VEGF, or PlGF nucleic acid sequence. Gene expression is then measured, for example, by microarray analysis, Northern blot analysis (Ausubel et al., supra), or RT-PCR, using any appropriate fragment prepared from the nucleic acid molecule as a hybridization probe. The level of gene expression in the presence of the candidate compound is compared to the level measured in a control culture medium lacking the candidate compound. A compound that promotes an alteration such as an increase in the expression of a VEGF or PlGF gene, nucleic acid molecule, or polypeptide, or a decrease in the expression of an sFlt-1 gene, nucleic acid molecule, or polypeptide, or a functional equivalent thereof, is considered useful in the invention; such a molecule may be used, for example, as a therapeutic to treat pre-eclampsia or eclampsia in a subject.

In another working example, the effect of candidate compounds may be measured at the level of polypeptide production using the same general approach and standard immunological techniques, such as Western blotting or immunoprecipitation with an antibody specific for a sFlt-1, VEGF, or PlGF polypeptide. For example, immunoassays may be used to detect or monitor the expression of at least one of the polypeptides of the invention in an organism. Polyclonal or monoclonal antibodies (produced as described above) that are capable of binding to such a polypeptide may be used in any standard immunoassay format (e.g., ELISA, western blot, or RIA assay) to measure the level of the polypeptide. In some embodiments, a compound that promotes an alteration such as an increase in the expression or biological activity of a VEGF or PlGF polypeptide or a decrease in the expression or biological activity of an sFlt-1 polypeptide is considered particularly useful. Again, such a molecule may be used, for example, as a therapeutic to delay, ameliorate, or treat a pre-eclampsia or eclampsia, or the symptoms of a pre-eclampsia or eclampsia, in a subject.

In yet another working example, candidate compounds may be screened for those that specifically bind to an sFlt-1, VEGF, or PlGF polypeptide. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind a polypeptide of the invention. In another embodiment, a candidate compound is tested for its ability to decrease the biological activity of an sFlt-1 polypeptide by decreasing binding of an sFlt-1 polypeptide and a growth factor, such as VEGF or PlGF.

In another working example, an sFlt-1, VEGF, or PlGF nucleic acid is expressed as a transcriptional or translational fusion with a detectable reporter, and expressed in an isolated cell (e.g., mammalian or insect cell) under the control of a heterologous promoter, such as an inducible promoter. The cell expressing the fusion protein is then contacted with a candidate compound, and the expression of the detectable reporter in that cell is compared to the expression of the detectable reporter in an untreated control cell. A candidate compound that decreases the expression of an sFlt-1 detectable reporter, or that increases the expression of a VEGF or PlGF detectable reporter is a compound that is useful for the treatment of pre-eclampsia or eclampsia. In preferred embodiments, the candidate compound alters the expression of a reporter gene fused to a nucleic acid or nucleic acid.

In one particular working example, a candidate compound that binds to an sFlt-1 polypeptide may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the sFlt-1 polypeptide is identified on the basis of its ability to bind to the polypeptide and be immobilized on the column. To isolate the compound, the column is washed to remove non-specifically bound molecules, and the compound of interest is then released from the column and collected. Similar methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to decrease the activity of an sFlt-1 polypeptide or to increase the activity of a VEGF signaling pathway (e.g., as described herein). Compounds isolated by this approach may also be used, for example, as therapeutics to treat pre-eclampsia or eclampsia in a human subject. Compounds that are identified as binding to a polypeptide of the invention with an affinity constant less than or equal to 10 mM are considered particularly useful in the invention. Alternatively, any in vivo protein interaction detection system, for example, any two-hybrid assay may be utilized to identify compounds or proteins that bind to a polypeptide of the invention.

Potential antagonists include organic molecules, peptides, peptide mimetics, polypeptides, nucleic acids, and antibodies that bind to an sFlt-1 nucleic acid sequence or sFlt-1 polypeptide.

sFlt-1 DNA sequences may also be used in the discovery and development of a therapeutic compound for the treatment of pre-eclampsia or eclampsia. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that decrease the expression of an sFlt-1 coding sequence. Such sequences may be isolated by standard techniques (Ausubel et al., supra).

Optionally, compounds identified in any of the above-described assays may be confirmed as useful in an assay for compounds that decrease the biological activity of sFlt-1 or that increase the activity of a VEGF signaling pathway.

Small molecules of the invention preferably have a molecular weight below 2,000 daltons, more preferably between 300 and 1,000 daltons, and most preferably between 400 and 700 daltons. It is preferred that these small molecules are organic molecules.

Therapeutics Targeting the VEGF Signaling Pathway

VEGF is a potent endothelial cell-specific mitogen that stimulates angiogenesis, vascular hyperpermeability, and vasodilation. Three tyrosine-kinase signaling receptors for VEGF have been identified. VEGF-receptor binding triggers a signaling cascade that results in tyrosine phosphorylation of phospholipase $C\gamma 1$, leading to increases in intracellular levels of inositol 1,4,5-triphosphate and increases in intracellular calcium that activates nitric oxide synthase to produce nitric oxide (NO). NO formation activates guanylate cyclase within vascular smooth muscle cells and endothelial cells, causing cGMP production. This NO/cGMP cascade is thought to mediate the vasoactive effects of VEGF. Another pathway that appears to be involved in mediating the vasoactive effects of VEGF is the prostacyclin release pathway.

VEGF induces PGI2 production via activation of phospholipase A2 as a consequence of initiation of the MAPK cascade.

Increased VEGF levels are useful for the treatment of pre-eclampsia and eclampsia. Therapeutic compounds that target VEGF signaling pathways, or components of a VEGF signaling pathway, and enhance the activity of a VEGF signaling pathway are also useful for the treatment of pre-eclampsia and eclampsia. Such compounds include sildenafil, prostacyclin analogs, such as Flolan, Remodulin, and Tracleer.

Test Compounds and Extracts

In general, compounds capable of decreasing the activity of a sFlt-1 polypeptide or increasing the activity of VEGF or PlGF are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their molt-disrupting activity should be employed whenever possible.

When a crude extract is found to decrease the activity of an sFlt-1 polypeptide, or to bind to sFlt-1 polypeptide, further fractionation of the positive lead extract is necessary to isolate chemical constituents responsible for the observed effect. Thus, the goal of the extraction, fractionation, and purification process is the careful characterization and identification of a chemical entity within the crude extract that decreases the activity of an sFlt-1 polypeptide. Methods of fractionation and purification of such heterogeneous extracts are known in the art. If desired, compounds shown to be useful as therapeutics for the treatment of a human pre-eclampsia or eclampsia are chemically modified according to methods known in the art.

Therapeutics

The present invention features methods for treating or preventing pre-eclampsia or eclampsia in a subject. Preferably, the therapeutic is administered during pregnancy for the treatment or prevention of pre-eclampsia or eclampsia or after pregnancy to treat post-partum pre-eclampsia or eclampsia. Techniques and dosages for administration vary depending on the type of compound (e.g., chemical compound, antibody, antisense, or nucleic acid vector) and are well known to those skilled in the art or are readily determined.

Therapeutic compounds of the present invention may be administered with a pharmaceutically acceptable diluent, carrier, or excipient, in unit dosage form. Administration may be parenteral, intravenous, subcutaneous, oral or local by direct injection into the amniotic fluid. Intravenous delivery by continuous infusion is the preferred method for administering the therapeutic compounds of the present invention.

The composition can be in the form of a pill, tablet, capsule, liquid, or sustained release tablet for oral administration; or a liquid for intravenous, subcutaneous or parenteral administration; or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The compound may be optionally administered as a pharmaceutically acceptable salts, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The dosage and the timing of administering the compound depends on various clinical factors including the overall health of the subject and the severity of the symptoms of pre-eclampsia. In general, once pre-eclampsia or a propensity to develop pre-eclampsia is detected, continuous infusion of the purified protein is used to treat or prevent further progression of the condition. Treatment can be continued for a period of time ranging from 1 to 100 days, more preferably 1 to 60 days, and most preferably 1 to 20 days, or until the completion of pregnancy. Dosages vary depending on each compound and the severity of the condition and are titrated to achieve a steady-state blood serum concentration ranging from 1 to 500 ng/mL VEGF or PlGF, or both, preferably 1 to 100 ng/mL, more preferably 5 to 50 ng/mL and most preferably 5 to 10 ng/mL VEGF or PlGF, or both.

The diagnostic methods described herein can also be used to monitor the pre-eclampsia or eclampsia during therapy or to determine the dosages of therapeutic compounds. In one example, a therapeutic compound is administered and the PAAI is determined during the course of therapy. If the PAAI is less than 10, preferably less than 20, then the therapeutic dosage is considered to be an effective dosage.

Methods to Increase VEGF or PlGF Protein Expression

The present invention features methods for increasing the levels of VEGF and PlGF in a subject diagnosed with pre-eclampsia or eclampsia. The increased levels of VEGF or PlGF can be achieved using several different methodologies that are described below, among others.

Purified Proteins

In a preferred embodiment of the present invention, purified forms of VEGF or PlGF or both are administered to the subject in order to treat or prevent pre-eclampsia or eclampsia.

Purified VEGF or VEGF-like proteins include any protein with an amino acid sequence that is homologous, more desirably, substantially identical to the amino acid sequence of VEGF, or any VEGF family member, that can induce angiogenesis or that is capable of promoting selective growth of vascular endothelial cells or umbilical vein endothelial cells. One example of a purified VEGF compound is human recombinant VEGF-165 from Genentech, Inc. (San Francisco, Calif.). Another example is human recombinant VEGF-121 from Scios, Inc (Fremont, Calif.).

Purified PlGF or PlGF-like proteins include any protein with an amino acid sequence that is homologous, more desirably, substantially identical to the amino acid sequence of PlGF, or any PlGF family member, that can induce angiogenesis or that is capable of promoting selective growth of vascular endothelial cells or umbilical vein endothelial cells. An example of commercially available purified PlGF is human recombinant PlGF from R&D Systems (catalog #264-PG, R&D Systems, Minneapolis, Minn.). ThromboGenics Ltd is also developing a purified form of PlGF for the treatment of ischemic stroke; presumably this form of PlGF would be effective for the applications described in the present invention.

Therapeutic Compounds that Increase VEGF or PlGF Activity

The present invention provides for the use of any compound known to stimulate or increase blood serum levels of VEGF or PlGF, or the biological activity of these polypeptides, for the treatment or prevention of pre-eclampsia in a subject. These compounds can be used alone or in combination with the purified proteins described above or any of the other methods used to increase VEGF or PlGF protein levels described herein.

One example of a compound shown to stimulate VEGF production is nicotine. Although smoking poses many risks for the overall health of a pregnant woman and her developing fetus, nicotine by itself is believed to be safer than cigarettes and can be used for short-term therapy on high-risk subjects. Examples include Nicorette (nicotine polacrilex), which is an over-the-counter nicotine gum product made by SmithKline Beecham and NicoDerm CQ, which is an over-the counter nicotine patch made by Hoechst Marion Roussel Inc. (formerly Marion Merrell Dow). Nicotine delivered via tobacco is specifically excluded from the methods of the invention where the patient has not also been diagnosed using the methods of the invention.

Nicotine is administered after the diagnosis of pre-eclampsia or eclampsia using either the patch or gum. Dosages vary depending on the severity of the condition and the overall health of the subject. In general, the manufacturer's instructions are followed to achieve a serum level of nicotine ranging from 5 to 500 ng/mL, more preferably 5 to 100 ng/mL, and most preferably 50 to 100 ng/mL.

Theophylline is another example of an additional compound that can be used to treat or prevent pre-eclampsia or eclampsia. Theophylline is a bronchodilator which is often used for the treatment of asthma and is available under many brand names (e.g., Aerolate Sr, Asmalix, Elxophyllin, etc.) as well as the generic. Methods of administration and dosages vary with each manufacturer and are chosen based on the overall health of the subject and the severity of the condition. In general, daily dosages range from 1 to 500 mg, more preferably 100 to 400 mg, and most preferably 250 to 350 mg given twice a day to achieve a serum level of theophylline of 5 to 50 µg/mL.

Adenosine is another example of an additional compound that can be used to treat or prevent pre-eclampsia or eclampsia. Adenosine (Fujisawa Pharmaceutical Co.) is commonly used as an anti-hypertensive drug. Methods of administration and dosages vary with each manufacturer and are chosen based on the overall health of the subject and the severity of the condition. In general, a daily dosage of 50 mg/kg given twice a day is typical for adenosine.

Nifedipine is another example of an additional compound that can be used to treat or prevent pre-eclampsia or eclampsia. Nifedipine (Bayer Pharmaceuticals) is commonly used as an anti-hypertensive drug. Methods of administration and dosages vary with each manufacturer and are chosen based on the overall health of the subject and the severity of the condition. In general, a daily dosage of 1-2 mg/kg given twice a day orally or subcutaneously is typical for nifedipine.

Minoxidil is another example of an additional compound that can be used to treat or prevent pre-eclampsia or eclampsia. Minoxidil is commonly used as an anti-hypertensive drug. Methods of administration and dosages vary with each manufacturer and are chosen based on the overall health of the subject and the severity of the condition. In general, a daily dosage of 0.25 to 1.0 mg/kg given twice a day orally or subcutaneously is typical for minoxidil.

Magnesium sulfate is another example of an additional compound that can be used to treat or prevent pre-eclampsia or eclampsia. Magnesium sulfate is a generic drug which is typically used as an anti-hypertensive drug. Methods of administration and dosages vary with each manufacturer and are chosen based on the overall health of the subject and the severity of the condition. In general, a daily dosage of 1-2 gm given intravenously ever four hours is a typical dosage for magnesium sulfate.

In addition to the use of compounds that can increase serum levels of VEGF or PlGF, the invention provides for the use of any chronic hypertension medications used in combination with any of the VEGF or PlGF directed compounds. Medications used for the treatment of hypertension during pregnancy include methyldopa, hydralazine hydrochloride, or labetalol. For each of these medications, modes of administration and dosages are determined by the physician and by the manufacturer's instructions.

Therapeutic Nucleic Acids

Recent work has shown that the delivery of nucleic acid (DNA or RNA) capable of expressing an endothelial cell mitogen such as VEGF to the site of a blood vessel injury will induce proliferation and reendothelialization of the injured vessel. While the present invention does not relate to blood vessel injury, the techniques for the delivery of nucleic acid encoding endothelial cell mitogens such as VEGF and PlGF used in these studies can also be employed in the present invention. These techniques are described in U.S. Pat. Nos. 5,830,879 and 6,258,787 and are incorporated herein by reference.

In the present invention the nucleic acid may be any nucleic acid (DNA or RNA) including genomic DNA, cDNA, and mRNA, encoding VEGF or PlGF or any VEGF or PlGF family members. The nucleic acid may also include any nucleic acid which encodes a protein shown to bind to the sFlt-1 receptor. The nucleic acids encoding the desired protein may be obtained using routine procedures in the art, e.g. recombinant DNA, PCR amplification.

Therapeutic Nucleic Acids that Inhibit sFlt-1 Expression

The present invention also features the use of antisense nucleobase oligomers to downregulate expression of sFlt-1 mRNA directly. By binding to the complementary nucleic acid sequence (the sense or coding strand), antisense nucleobase oligomers are able to inhibit protein expression presumably through the enzymatic cleavage of the RNA strand by RNAse H. Preferably the antisense nucleobase oligomer is capable of reducing sFlt-1 protein expression in a cell that expresses excess levels of sFlt-1. Preferably the decrease in sFlt-1 protein expression is at least 10% relative to cells treated with a control oligonucleotide, more preferably 25%, and most preferably 50% or greater. Methods for selecting and preparing antisense nucleobase oligomers are well known in the art. For an example of the use of antisense nucleobase oligomers to downregulate VEGF expression see U.S. Pat. No. 6,410,322, incorporated herein by reference. Methods for assaying levels of protein expression are also well known in the art and include western blotting, immunoprecipitation, and ELISA.

The present invention also features the use of RNA interference (RNAi) to inhibit expression of sFlt-1. RNA interference (RNAi) is a recently discovered mechanism of post-transcriptional gene silencing (PTGS) in which double-stranded RNA (dsRNA) corresponding to a gene or mRNA of interest is introduced into an organism resulting in the degradation of the corresponding mRNA. In the RNAi reaction, both the sense and anti-sense strands of a dsRNA molecule are processed into small RNA fragments or segments ranging in length from 21 to 23 nucleotides (nt) and having 2-nucleotide 3' tails. Alternatively, synthetic dsRNAs, which are 21 to 23 nt in length and have 2-nucleotide 3' tails, can be synthesized, purified and used in the reaction. These 21 to 23 nt dsRNAs are known as "guide RNAs" or "short interfering RNAs" (siRNAs).

The siRNA duplexes then bind to a nuclease complex composed of proteins that target and destroy endogenous mRNAs having homology to the siRNA within the complex. Although the identity of the proteins within the complex remains unclear, the function of the complex is to target the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene.

The specific requirements and modifications of dsRNA are described in PCT Publication No. WO01/75164 (incorporated herein by reference). While dsRNA molecules can vary in length, it is most preferable to use siRNA molecules which are 21- to 23-nucleotide dsRNAs with characteristic 2- to 3-nucleotide 3' overhanging ends typically either (2'-deoxy)thymidine or uracil. The siRNAs typically comprise a 3' hydroxyl group. Single stranded siRNA as well as blunt ended forms of dsRNA can also be used. In order to further enhance the stability of the RNA, the 3' overhangs can be stabilized against degradation. In one such embodiment, the RNA is stabilized by including purine nucleotides, such as adenosine or guanosine. Alternatively, substitution of pyrimidine nucleotides by modified analogs, e.g., substitution of uridine 2-nucleotide overhangs by (2'-deoxy)thymide is tolerated and does not affect the efficiency of RNAi. The absence of a 2' hydroxyl group significantly enhances the nuclease resistance of the overhang in tissue culture medium.

Alternatively siRNA can be prepared using any of the methods set forth in PCT Publication No. WO01/75164 (incorporated herein by reference) or using standard procedures for in vitro transcription of RNA and dsRNA annealing procedures as described in Elbashir et al. (*Genes & Dev.*, 15:188-200, 2001). siRNAs are also obtained as described in Elbashir et al. by incubation of dsRNA that corresponds to a sequence of the target gene in a cell-free Drosophila lysate from syncytial blastoderm Drosophila embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g., size exclusion chromatography), glycerol gradient centrifugation, and affinity purification with antibody can be used to isolate the 21 to 23 nt RNAs.

In the present invention, the dsRNA, or siRNA, is complementary to the mRNA sequence of an sFlt-1 mRNA and can reduce or inhibit expression of sFlt-1. Preferably, the decrease in sFlt-1 protein expression is at least 10% relative to cells treated with a control dsRNA or siRNA, more preferably 25%, and most preferably at least 50%. Methods for assaying levels of protein expression are also well known in the art and include western blotting, immunoprecipitation, and ELISA.

In the present invention, the nucleic acids used include any modification that enhances the stability or function of the nucleic acid in any way. Examples include modifications to the phosphate backbone, the internucleotide linkage, or to the sugar moiety.

To simplify the manipulation and handling of the nucleic acid encoding the sFlt-1 binding protein, the nucleic acid is preferably inserted into a cassette where it is operably linked to a promoter. The promoter must be capable of driving expression of the sFlt-1 binding protein in the desired target host cell. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum. Gene Ther.* 4:151-159, 1993) and mouse mammary tumor virus (MMTV) promoters may also be used. Certain proteins can be expressed using their native promoter. Other elements that can enhance expression can also be included (e.g., enhancers or a system that results in high levels of expression such as a tat gene and tar element). The recombinant vector can be a plasmid vector such as pUC 118, pBR322, or other known plasmid vectors, that includes, for example, an *E. coli* origin of replication (see, Sambrook, et al., Molecular Cloning: A Laboratory Manual, Cold Spring Harbor Laboratory press, 1989). The plasmid vector may also include a selectable marker such as the β lactamase gene for ampicillin resistance, provided that the marker polypeptide does not adversely affect the metabolism of the organism being treated. The cassette can also be bound to a nucleic acid binding moiety in a synthetic delivery system, such as the system disclosed in PCT Publication No. WO95/22618.

The nucleic acid can be introduced into the cells by any means appropriate for the vector employed. Many such methods are well known in the art (Sambrook et al., supra, and Watson et al., "Recombinant DNA", Chapter 12, 2d edition, Scientific American Books, 1992). Recombinant vectors can be transferred by methods such as calcium phosphate precipitation, electroporation, liposome-mediated transfection, gene gun, microinjection, viral capsid-mediated transfer, polybrene-mediated transfer, or protoplast fusion. For a review of the procedures for liposome preparation, targeting and delivery of contents, see Mannino and Gould-Fogerite, (*Bio Techniques,* 6:682-690, 1988), Feigner and Holm, (*Bethesda Res. Lab. Focus,* 11:21, 1989) and Maurer (*Bethesda Res. Lab. Focus,* 11:25, 1989).

Transfer of the recombinant vector (either plasmid vector or viral vectors) can be accomplished through direct injection into the amniotic fluid or intravenous delivery.

Gene delivery using adenoviral vectors or adeno-associated vectors (AAV) can also be used. Adenoviruses are present in a large number of animal species, are not very pathogenic, and can replicate equally well in dividing and quiescent cells. As a general rule, adenoviruses used for gene delivery are lacking one or more genes required for viral replication. Replication-defective recombinant adenoviral vectors used for the delivery of VEGF, PlGF or any sFlt-1 binding protein, can be produced in accordance with art-known techniques (see Quantin et al., *Proc. Natl. Acad. Sci. USA,* 89:2581-2584, 1992; Stratford-Perricadet et al., *J. Clin. Invest.,* 90:626-630, 1992; and Rosenfeld et al., *Cell,* 68:143-155, 1992). For an example of the use of gene therapy in utero see U.S. Pat. No. 6,399,585.

A variety of methods are available for transfection, or introduction, of dsRNA or oligonucleotides into mammalian cells. For example, there are several commercially available transfection reagents including but not limited to: TransIT-TKO™ (Mirus, Cat. #MIR 2150), Transmessenger™ (Qiagen, Cat. #301525), and Oligofectamine™ (Invitrogen, Cat. #MIR 12252-011). Protocols for each transfection reagent are available from the manufacturer.

Once transferred, the nucleic acid is expressed by the cells at the site of injury for a period of time sufficient to increase blood serum levels of VEGF, PlGF, or any other sFlt-1 binding protein. Because the vectors containing the nucleic acid are not normally incorporated into the genome of the cells, expression of the protein of interest takes place for only a limited time. Typically, the protein is expressed at therapeutic levels for about two days to several weeks, preferably for about one to two weeks. Re-application of the DNA can be utilized to provide additional periods of expression of the therapeutic protein. Recent examples of gene therapy using VEGF for the treatment of vascular disease in mammals can be found in Deodato et al. (*Gene Ther.,* 9:777-785, 2002); Isner et al. (*Human Gene Ther.,* 12:1593-1594, 2001); Lai et al. (*Gene Ther.,* 9:804-813, 2002); and reviewed in Freedman and Isner (*Ann. Intern. Med.,* 136: 54-71, 2002) and Isner J M (*Nature,* 415:234-239, 2002).

Assays for Gene and Protein Expression

The following methods can be used to evaluate protein or gene expression and determine efficacy for any of the above-mentioned methods for increasing VEGF, PlGF or any other sFlt-1 binding protein levels, or for decreasing sFlt-1 protein levels.

Blood serum from the subject is measured for levels of VEGF, PlGF, or any protein ligand known to bind to sFlt-1. Methods used to measure serum levels of proteins include ELISA, western blotting, or immunoassays using specific antibodies. In addition, in vitro angiogenesis assays can be performed to determine if the subject's blood has converted from an anti-angiogenic state to a pro-angiogenic state. Such assays are described above in Example 2. A positive result is considered an increase of at least 20%, preferably 30%, more preferably at least 50%, and most preferably at least 60% in the serum levels of VEGF, PlGF, or any protein ligand known to bind to sFlt-1. A positive result can also be considered conversion from an anti-angiogenic state to a pro-angiogenic state using the in vitro angiogenesis assay.

Blood serum samples from the subject can also be measured for levels of VEGF, PlGF or sFlt-1 nucleic acid levels. There are several art-known methods to assay for gene expression. Some examples include the preparation of RNA from the blood samples of the subject and the use of the RNA for northern blotting, PCR based amplification, or RNAse protection assays.

Use of Antibodies for Therapeutic Treatment

The elevated levels of sFlt-1 found in the serum samples taken from pregnant women suffering from pre-eclampsia suggests that sFlt-1 is acting as a "physiologic sink" to bind to and deplete the trophoblast cells and maternal endothelial cells of functional VEGF and PlGF. The use of compounds, such as antibodies, to bind to sFlt-1 and block VEGF or PlGF binding, may help prevent or treat pre-eclampsia or eclampsia, by producing an increase in free VEGF or PlGF. Such an increase would allow for an increase in trophoblast proliferation, migration and angiogenesis required for placental development and fetal nourishment, and for systemic maternal endothelial cell health.

The present invention provides antibodies that bind specifically to the ligand-binding domain of sFlt-1. The antibodies are used to inhibit sFlt-1 and the most effective mechanism is believed to be through direct blocking of the binding sites for VEGF or PlGF, however, other mechanisms cannot be ruled out. Methods for the preparation and use of antibodies for therapeutic purposes are described in several patents including U.S. Pat. Nos. 6,054,297; 5,821,337; 6,365,157; and 6,165,464 and are incorporated herein by reference. Antibodies can be polyclonal or monoclonal; monoclonal antibodies are preferred.

Monoclonal antibodies, particularly those derived from rodents including mice, have been used for the treatment of various diseases; however, there are limitations to their use including the induction of a human anti-mouse immunoglobulin response that causes rapid clearance and a reduction in the efficacy of the treatment. For example, a major limitation in the clinical use of rodent monoclonal antibodies is an anti-globulin response during therapy (Miller et al., *Blood,* 62:988-995 1983; Schroff et al., *Cancer Res.,* 45:879-885, 1985).

The art has attempted to overcome this problem by constructing "chimeric" antibodies in which an animal antigen-binding variable domain is coupled to a human constant domain (U.S. Pat. No. 4,816,567; Morrison et al., *Proc. Natl. Acad. Sci. USA,* 81:6851-6855, 1984; Boulianne et al., *Nature,* 312:643-646, 1984; Neuberger et al., *Nature,* 314: 268-270, 1985). The production and use of such chimeric antibodies are described below.

Competitive inhibition of ligand binding to sFlt-1 is useful for the prevention or treatment of pre-eclampsia or eclampsia. Antibodies directed to sFlt-1 can block binding of VEGF or PlGF to sFlt-1 resulting in increased levels of VEGF or PlGF. Such an increase can result in a rescue of endothelial dysfunction and a shift in the balance of pro-angiogenic/anti-angiogenic factors towards angiogenesis.

A cocktail of the monoclonal antibodies of the present invention can be used as an effective treatment for pre-eclampsia or eclampsia. The cocktail may include as few as two, three, or four different antibodies or as many as six, eight, or ten different antibodies. In addition, the antibodies of the present invention can be combined with an anti-hypertensive drug (e.g., methyldopa, hydralazine hydrochloride, or labetalol) or any other medication used to treat pre-eclampsia, eclampsia, or the symptoms associated with pre-eclampsia or eclampsia.

Preparation of Antibodies

Monoclonal antibodies that specifically bind to the sFlt-1 receptor may be produced by methods known in the art. These methods include the immunological method described by Kohler and Milstein (*Nature,* 256: 495-497, 1975) and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam, 1985), as well as by the recombinant DNA method described by Huse et al. (*Science,* 246, 1275-1281, 1989).

Monoclonal antibodies may be prepared from supernatants of cultured hybridoma cells or from ascites induced by intra-peritoneal inoculation of hybridoma cells into mice. The hybridoma technique described originally by Kohler and Milstein (*Eur. J. Immunol,* 6, 511-519, 1976) has been widely applied to produce hybrid cell lines that secrete high levels of monoclonal antibodies against many specific antigens.

The route and schedule of immunization of the host animal or cultured antibody-producing cells therefrom are generally in keeping with established and conventional techniques for antibody stimulation and production. Typically, mice are used as the test model, however, any mammalian subject including human subjects or antibody producing cells therefrom can be manipulated according to the processes of this invention to serve as the basis for production of mammalian, including human, hybrid cell lines.

After immunization, immune lymphoid cells are fused with myeloma cells to generate a hybrid cell line that can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleen tissue from immunized animals. The use of spleen cells is preferred, since they offer a more concentrated and convenient source of antibody producing cells with respect to the mouse system. The myeloma cells provide the basis for continuous propagation of the fused hybrid. Myeloma cells are tumor cells derived from plasma cells. Murine myeloma cell lines can be obtained, for example, from the American Type Culture Collection (ATCC; Manassas, Va.). Human myeloma and mouse-human heteromyeloma cell lines have also been described (Kozbor et al., *J. Immunol.,* 133:3001-3005, 1984; Brodeur et al., Monoclonal Antibody Production Techniques and Applications, Marcel Dekker, Inc., New York, pp. 51-63, 1987).

The hybrid cell lines can be maintained in vitro in cell culture media. Once the hybridoma cell line is established, it can be maintained on a variety of nutritionally adequate media such as hypoxanthine-aminopterin-thymidine (HAT) medium. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange chromatography, affinity chromatography, or the like.

The antibody may be prepared in any mammal, including mice, rats, rabbits, goats, and humans. The antibody may be a member of one of the following immunoglobulin classes: IgG, IgM, IgA, IgD, or IgE, and the subclasses thereof, and preferably is an IgG antibody.

While the preferred animal for producing monoclonal antibodies is mouse, the invention is not so limited; in fact, human antibodies may be used and may prove to be preferable. Such antibodies can be obtained by using human hybridomas (Cole et al., "Monoclonal Antibodies and Cancer Therapy", Alan R. Liss Inc., p. 77-96, 1985). In the present invention, techniques developed for the production of chimeric antibodies by splicing the genes from a mouse antibody molecule of appropriate antigen specificity together with genes from a human antibody molecule can be used (Morrison et al., *Proc. Natl. Acad. Sci.* 81, 6851-6855, 1984; Neuberger et al., *Nature* 312, 604-608, 1984; Takeda et al., *Nature* 314, 452-454, 1985); such antibodies are within the scope of this invention and are described below.

As another alternative to the cell fusion technique, Epstien-Barr virus (EBV) immortalized B cells are used to produce the monoclonal antibodies of the present invention (Crawford D. et al., *J. of Gen. Virol.,* 64:697-700, 1983; Kozbor and Roder, *J. Immunol.,* 4:1275-1280, 1981; Kozbor et al., *Methods in Enzymology,* 121:120-140, 1986). In general, the procedure consists of isolating Epstein-Barr virus from a suitable source, generally an infected cell line, and exposing the target antibody secreting cells to supernatants containing the virus. The cells are washed, and cultured in an appropriate cell culture medium. Subsequently, virally transformed cells present in the cell culture can be identified by the presence of the Epstein-Barr viral nuclear antigen, and transformed antibody secreting cells can be identified using standard methods known in the art. Other methods for producing monoclonal antibodies, such as recombinant DNA, are also included within the scope of the invention.

Preparation of sFlt-1 Immunogens sFlt-1 may be used by itself as an immunogen, or may be attached to a carrier protein or to other objects, such as sepharose beads. sFlt-1 may be purified from cells known to express the endogenous protein such as human umbilical vein endothelial cells (HUVEC; Kendall et al., *Biochem.*

*Biophys. Res. Comm.,* 226:324-328, 1996). Additionally, nucleic acid molecules that encode sFlt-1, or portions thereof, can be inserted into known vectors for expression in host cells using standard recombinant DNA techniques. Suitable host cells for sFlt-1 expression include baculovirus cells (e.g., Sf9 cells), bacterial cells (e.g., *E. coli*), and mammalian cells (e.g., NIH3T3 cells).

In addition, peptides can be synthesized and used as immunogens. The methods for making antibody to peptides are well known in the art and generally require coupling the peptide to a suitable carrier molecule, such as serum albumin. Peptides include any amino acid sequence that is substantially identical to any part of the sFlt-1 amino acid sequence corresponding to GenBank accession number U01134. Peptides can be any length, preferably 10 amino acids or greater, more preferably 25 amino acids or greater, and most preferably 40, 50, 60, 70, 80, or 100 amino acids or greater. Preferably, the amino acid sequences are at least 60%, more preferably 85%, and, most preferably 95% identical to the sequence of U01134. The peptides can be commercially obtained or made using techniques well known in the art, such as, for example, the Merrifield solid-phase method (*Science,* 232:341-347, 1985). The procedure may use commercially available synthesizers such as a Biosearth 9500 automated peptide machine, with cleavage of the blocked amino acids being achieved with hydrogen fluoride, and the peptides purified by preparative HPLC using a Waters Delta Prep 3000 instrument, on a 15-20 μm Vydac C4 PrepPAK column.

Functional Equivalents of Antibodies

The invention also includes functional equivalents of the antibodies described in this specification. Functional equivalents include polypeptides with amino acid sequences substantially identical to the amino acid sequence of the variable or hypervariable regions of the antibodies of the invention. Functional equivalents have binding characteristics comparable to those of the antibodies, and include, for example, chimerized, humanized and single chain antibodies as well as fragments thereof. Methods of producing such functional equivalents are disclosed, for example, in PCT Publication No. WO93/21319; European Patent Application No. 239,400; PCT Publication No. WO89/09622; European Patent Application No. 338,745; European Patent Application No. 332424; and U.S. Pat. No. 4,816,567; each of which is herein incorporated by reference.

Chimerized antibodies preferably have constant regions derived substantially or exclusively from human antibody constant regions and variable regions derived substantially or exclusively from the sequence of the variable region from a mammal other than a human. Such humanized antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Methods for humanizing non-human antibodies are well known in the art (for reviews see Vaswani and Hamilton, *Ann Allergy Asthma Immunol.,* 81:105-119, 1998 and Carter, *Nature Reviews Cancer,* 1:118-129, 2001). Generally, a humanized antibody has one or more amino acid residues introduced into it from a source that is non-human. These non-human amino acid residues are often referred to as import residues, which are typically taken from an import variable domain. Humanization can be essentially performed following the methods known in the art (Jones et al., *Nature,* 321:522-525, 1986; Riechmann et al., *Nature,* 332: 323-329, 1988; and Verhoeyen et al., *Science,* 239:1534-1536 1988), by substituting rodent CDRs or other CDR sequences for the corresponding sequences of a human antibody. Accordingly, such humanized antibodies are chimeric antibodies wherein substantially less than an intact human variable domain has been substituted by the corresponding sequence from a non-human species (see for example, U.S. Pat. No. 4,816,567). In practice, humanized antibodies are typically human antibodies in which some CDR residues and possibly some FR residues are substituted by residues from analogous sites in rodent antibodies (Presta, *Curr. Op. Struct. Biol.,* 2:593-596, 1992).

Additional methods for the preparation of humanized antibodies can be found in U.S. Pat. Nos. 5,821,337, and 6,054,297, and Carter, (supra) which are all incorporated herein by reference. The humanized antibody is selected from any class of immunoglobulins, including IgM, IgG, IgD, IgA and IgE, and any isotype, including $IgG_1$, $IgG_2$, $IgG_3$, and $IgG_4$. Where cytotoxic activity is not needed, such as in the present invention, the constant domain is preferably of the $IgG_2$ class. The humanized antibody may comprise sequences from more than one class or isotype, and selecting particular constant domains to optimize desired effector functions is within the ordinary skill in the art.

Human antibodies can also be produced using various techniques known in the art, including phage display libraries (Marks et al., *J. Mol. Biol.,* 222:581-597, 1991 and Winter et al. *Annu. Rev. Immunol.,* 12:433-455, 1994). The techniques of Cole et al. and Boerner et al. are also useful for the preparation of human monoclonal antibodies (Cole et al., supra; Boerner et al., *J. Immunol.,* 147: 86-95, 1991).

Suitable mammals other than a human include any mammal from which monoclonal antibodies may be made. Examples of mammals other than a human include, for example a rabbit, rat, mouse, horse, goat, or primate; a mouse is preferred.

Functional equivalents of antibodies also include single-chain antibody fragments, also known as single-chain antibodies (scFvs). Single-chain antibody fragments are recombinant polypeptides which typically bind antigens or receptors; these fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the $V_L$ and $V_H$ domains occurs once they are linked so as to maintain the target molecule binding-specificity of the whole antibody from which the single-chain antibody fragment is derived. Generally, the carboxyl terminus of the $V_L$ or $V_H$ sequence is covalently linked by such a peptide linker to the amino acid terminus of a complementary $V_L$ and $V_H$ sequence. Single-chain antibody fragments can be generated by molecular cloning, antibody phage display library or similar techniques. These proteins can be produced either in eukaryotic cells or prokaryotic cells, including bacteria.

Single-chain antibody fragments contain amino acid sequences having at least one of the variable regions or CDRs of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient.

Functional equivalents further include fragments of antibodies that have the same or comparable binding characteristics to those of the whole antibody. Such fragments may contain one or both Fab fragments or the F(ab')$_2$ fragment. Preferably the antibody fragments contain all six CDRs of the whole antibody, although fragments containing fewer than all of such regions, such as three, four or five CDRs, are also functional.

Further, the functional equivalents may be or may combine members of any one of the following immunoglobulin classes: IgG, IgM, IgA, IgD, or IgE, and the subclasses thereof.

Preparation of Functional Equivalents of Antibodies

Equivalents of antibodies are prepared by methods known in the art. For example, fragments of antibodies may be prepared enzymatically from whole antibodies. Preferably, equivalents of antibodies are prepared from DNA encoding such equivalents. DNA encoding fragments of antibodies may be prepared by deleting all but the desired portion of the DNA that encodes the full-length antibody.

DNA encoding chimerized antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the CDRs derived substantially or exclusively from the corresponding human antibody regions and DNA encoding CDRs derived substantially or exclusively from a mammal other than a human.

Suitable sources of DNA molecules that encode fragments of antibodies include cells, such as hybridomas, that express the full-length antibody. The fragments may be used by themselves as antibody equivalents, or may be recombined into equivalents, as described above.

The DNA deletions and recombinations described in this section may be carried out by known methods, such as those described in the published patent applications listed above.

Antibody Screening and Selection

Monoclonal antibodies are isolated and purified using standard art-known methods. For example, antibodies can be screened using standard art-known methods such as ELISA against the sFlt-1 peptide antigen or western blot analysis. Non-limiting examples of such techniques are described in Examples II and III of U.S. Pat. No. 6,365,157, herein incorporated by reference.

Therapeutic Uses of Antibodies

When used in vivo for the treatment or prevention of pre-eclampsia or eclampsia, the antibodies of the subject invention are administered to the subject in therapeutically effective amounts. Preferably, the antibodies are administered parenterally or intravenously by continuous infusion. The dose and dosage regimen depends upon the severity of the disease, and the overall health of the subject. The amount of antibody administered is typically in the range of about 0.001 to about 10 mg/kg of subject weight, preferably 0.01 to about 5 mg/kg of subject weight.

For parenteral administration, the antibodies are formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibodies typically are formulated in such vehicles at concentrations of about 1 mg/ml to 10 mg/ml.

Therapeutic Compounds that Inhibit sFlt-1

Given that levels of sFlt-1 are increased in subjects having pre-eclampsia, eclampsia, or having a propensity to develop such conditions, any agent that decreases the expression of an sFlt-1 polypeptide or nucleic acid molecule is useful in the methods of the invention. Such agents include small molecules that can disrupt sFlt-1 binding to VEGF or PlGF, antisense nucleobase oligomers, and dsRNAs used to mediate RNA interference.

Combination Therapies

Optionally, a pre-eclampsia or eclampsia therapeutic may be administered in combination with any other standard pre-eclampsia or eclampsia therapy; such methods are known to the skilled artisan and described herein. A pre-eclampsia or eclampsia therapeutic of the invention may be administered in combination with any compound that increases the activity of a VEGF pathway. Non-limiting examples of agents which also induce endogenous VEGF production include nicotine, minoxidil, nifidepine, adenosine, magnesium sulfate, and theophylline. In one embodiment, PlGF protein can be used in combination with any of the agents which induce endogenous VEGF production listed above.

Subject Monitoring

The disease state or treatment of a subject having pre-eclampsia, eclampsia, or a propensity to develop such a condition can be monitored using the methods and compositions of the invention. In one embodiment, the expression of an sFlt-1, VEGF, or PlGF polypeptide present in a bodily fluid, such as urine, plasma, amniotic fluid, or CSF, is monitored. Such monitoring may be useful, for example, in assessing the efficacy of a particular drug in a subject or in assessing disease progression. Therapeutics that decrease the expression of an sFlt-1 nucleic acid molecule or polypeptide or that increase the expression of a VEGF or PlGF nucleic acid molecule or polypeptide are taken as particularly useful in the invention.

Other Embodiments

From the foregoing description, it is apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference. In addition, U.S. Provisional Application Nos. 60/451,796, filed Mar. 3, 2003, 60/397,481, filed Jul. 19, 2002, and 60/467,390 filed May 2, 2003, are hereby incorporated by reference in their entirety.

What is claimed is:

1. A method for inhibiting the binding of VEGF or PlGF to an sFlt-1 polypeptide in a subject having pre-eclampsia or eclampsia or a propensity to develop pre-eclampsia or eclampsia, said method comprising contacting the sFlt-1 polypeptide with a polypeptide that binds sFlt-1, wherein said polypeptide is an anti-sFlt-1 antibody, or an antigen binding fragment thereof.

2. The method of claim 1, wherein said polypeptide that binds sFlt-1 competitively inhibits the binding of VEGF or PlGF to sFlt-1.

3. The method of claim 1, wherein said anti-sFlt-1 antibody, or antigen binding fragment thereof, specifically binds sFlt-1.

4. The method of claim 3, wherein said anti-sFlt-1 antibody, or antigen binding fragment thereof, binds sFlt-1 and does not bind Flt-I.

5. The method of claim 1, wherein said antibody, or antigen binding fragment thereof, reduces the levels of sFlt-1 in said subject.

6. The method of claim 1, wherein said antibody is a monoclonal antibody, a chimeric antibody, a human antibody, or a humanized antibody.

7. The method of claim 1, wherein said antibody, or antigen-binding fragment thereof, is an Fv, Fab, Fab', F(ab')2 fragment, or scFv.

8. The method of claim 1, wherein said antibody, or antigen-binding fragment thereof, is an IgG.

9. The method of claim 8, wherein said antibody, or antigen-binding fragment thereof, is an IgG1, IgG2, IgG3, or IgG4.

10. The method of claim 1, further comprising administering an anti-hypertensive drug to said subject.

11. The method of claim 10, wherein said anti-hypertensive drug is selected from the group consisting of methyl-dopa, hydralazine, hydrochloride, or labetalol.

12. The method of claim 1, wherein said sFlt-1 is an isoform of sFlt-1 or an sFlt-1 polypeptide resulting from degradation or enzymatic cleavage.

13. The method of claim 1, wherein said subject is a pregnant human or a post-partum human.

14. The method of claim 1, wherein said method further comprises monitoring said pre-eclampsia or eclampsia in said subject, wherein said monitoring comprises measuring the level of sFlt-1, free VEGF, or free PlGF polypeptide in a sample from said subject, wherein a decrease in the level of sFlt-1 or an increase in the level of free VEGF or free PlGF relative to a reference that is indicative of pre-eclampsia or eclampsia indicates an improvement in said pre-eclampsia or eclampsia in said subject.

15. The method of claim 14, wherein the level of sFlt-1 is measured and a decrease in the level of sFlt-1 relative to said reference indicates an improvement in said pre-eclampsia or eclampsia in said subject.

16. The method of claim 14, wherein the level of sFlt-1 is the level of free or bound sFlt-1.

17. The method of claim 14, wherein the level of sFlt-1 is the level of total sFlt-1.

18. The method of claim 14, wherein the level of sFlt-1 is the level of an isoform of sFlt-1 or an sFlt-1 polypeptide resulting from degradation or enzymatic cleavage.

19. The method of claim 14, wherein the level of free VEGF or free PlGF is measured and an increase in the level of free VEGF or free PlGF relative to a reference indicates an improvement in said pre-eclampsia or eclampsia in said subject.

20. The method of claim 14, wherein said measuring of levels is done on two or more occasions and a change in said levels between measurements indicates an improvement in said pre-eclampsia or eclampsia.

21. The method of claim 1, wherein said pre-eclampsia or eclampsia is characterized by increased sFlt-1 polypeptide or nucleic acid expression levels relative to a normal reference sample of level.

22. The method of claim 21, wherein said normal reference sample or level is a prior sample or level from said subject.

23. A method for reducing the level or biological activity of sFlt-1 polypeptide in a subject having pre-eclampsia or eclampsia or a propensity to develop pre-eclampsia or eclampsia, said method comprising contacting the sFlt-1 polypeptide with an anti-sFlt-1 antibody or an antigen-binding fragment thereof.

24. The method of claim 23, wherein the anti-sFlt-1 antibody specifically binds sFlt-1.

25. The method of claim 24, wherein the anti-sFlt-1 antibody binds sFlt-1 and does not bind to Flt-I.

26. The method of claim 23, wherein said antibody is a monoclonal antibody, a chimeric antibody, a human antibody, or a humanized antibody.

27. The method of claim 23, wherein said antibody or antigen-binding fragment is an Fv, Fab, Fab', F(ab')2 fragment, or scFv.

28. The method of claim 23, wherein said subject is a pregnant human or a post-partum human.

29. The method of claim 23, wherein said sFlt-1 is an isoform of sFlt-1 or an sFlt-1 polypeptide resulting from degradation or enzymatic cleavage.

30. The method of claim 23, wherein said method further comprises monitoring said pre-eclampsia or eclampsia in said subject, wherein said monitoring comprises measuring the level of sFlt-1, free VEGF, or free PlGF polypeptide in a sample from said subject, wherein a decrease in the level of sFlt-1 or an increase in the level of free VEGF or free PlGF relative to a reference that is indicative of pre-eclampsia or eclampsia indicates an improvement in said pre-eclampsia or eclampsia in said subject.

31. The method of claim 30, wherein the level of sFlt-1 is measured and a decrease in the level of sFlt-1 relative to said reference indicates an improvement in said pre-eclampsia or eclampsia in said subject.

32. The method of claim 30, wherein the level of sFlt-1 is the level of free or bound sFlt-1.

33. The method of claim 30, wherein the level of sFlt-1 is the level of total sFlt-1.

34. The method of claim 30, wherein said sFlt-1 is an isoform of sFlt-1 or an sFlt-1 polypeptide resulting from degradation or enzymatic cleavage.

* * * * *